US008283142B2

(12) United States Patent
Dicosimo et al.

(10) Patent No.: US 8,283,142 B2
(45) Date of Patent: Oct. 9, 2012

(54) STABILIZATION OF PERHYDROLASES

(75) Inventors: Robert Dicosimo, Chadds Ford, PA (US); Arie Ben-Bassat, Wilmington, DE (US); Mark S. Payne, Wilmington, DE (US); Raymond Richard Zolandz, Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 13/213,602

(22) Filed: Aug. 19, 2011

(65) Prior Publication Data
US 2011/0306103 A1 Dec. 15, 2011

Related U.S. Application Data

(62) Division of application No. 12/572,086, filed on Oct. 1, 2009, now Pat. No. 8,030,038.

(60) Provisional application No. 61/102,505, filed on Oct. 3, 2008, provisional application No. 61/102,512, filed on Oct. 3, 2008, provisional application No. 61/102,514, filed on Oct. 3, 2008, provisional application No. 61/102,520, filed on Oct. 3, 2008, provisional application No. 61/102,531, filed on Oct. 3, 2008, provisional application No. 61/102,539, filed on Oct. 3, 2008.

(51) Int. Cl.
*C12P 7/40* (2006.01)
*C12N 9/00* (2006.01)
*D06L 1/02* (2006.01)
*C11D 3/386* (2006.01)
*C07H 21/04* (2006.01)

(52) U.S. Cl. ........ 435/136; 435/183; 510/281; 510/305; 536/23.2

(58) Field of Classification Search ................ None
See application file for complete search history.

(56) References Cited

U.S. PATENT DOCUMENTS

| | | |
|---|---|---|
| 3,974,082 A | 8/1976 | Weyn |
| 4,444,886 A | 4/1984 | Esders et al. |
| 4,585,150 A | 4/1986 | Beacham et al. |
| 4,678,103 A | 7/1987 | Dirksing |
| 5,116,575 A | 5/1992 | Badertscher et al. |
| 5,152,461 A | 10/1992 | Proctor |
| 5,281,525 A | 1/1994 | Mitsushima et al. |
| 5,296,161 A | 3/1994 | Wiersema et al. |
| 5,338,676 A | 8/1994 | Mitsushima et al. |
| 5,364,554 A | 11/1994 | Stanislowski et al. |
| 5,398,846 A | 3/1995 | Corba et al. |
| 5,528,152 A | 6/1996 | Hinoshita et al. |
| 5,532,157 A | 7/1996 | Fink |
| 5,605,793 A | 2/1997 | Stemmer |
| 5,624,634 A | 4/1997 | Brougham et al. |
| 5,683,724 A | 11/1997 | Hei et al. |
| 5,811,238 A | 9/1998 | Stemmer et al. |
| 5,830,721 A | 11/1998 | Stemmer et al. |
| 5,837,458 A | 11/1998 | Minshull et al. |
| 5,862,949 A | 1/1999 | Markey et al. |
| 5,932,532 A | 8/1999 | Ghosh et al. |
| 5,954,213 A | 9/1999 | Gerhart et al. |
| 6,183,807 B1 | 2/2001 | Gutzmann et al. |
| 6,210,639 B1 | 4/2001 | Vlass et al. |
| 6,223,942 B1 | 5/2001 | Markey et al. |
| 6,319,888 B2 | 11/2001 | Wei et al. |
| 6,391,840 B1 | 5/2002 | Thompson et al. |
| 6,465,233 B1 | 10/2002 | Knauseder et al. |
| 6,518,307 B2 | 2/2003 | McKenzie et al. |
| 6,545,047 B2 | 4/2003 | Gutzmann et al. |
| 6,635,286 B2 | 10/2003 | Hei et al. |
| 6,645,233 B1 | 11/2003 | Ayers et al. |
| 6,758,411 B2 | 7/2004 | Conway et al. |
| 6,995,125 B2 | 2/2006 | Dasque et al. |
| 7,448,556 B2 | 11/2008 | Muehlhausen et al. |
| 7,723,083 B2 | 5/2010 | DiCosimo et al. |
| 7,964,378 B2 | 6/2011 | Dicosimo et al. |
| 2002/0030063 A1 | 3/2002 | Leray et al. |
| 2004/0127381 A1 | 7/2004 | Scialla et al. |
| 2005/0008526 A1 | 1/2005 | Bianchetti et al. |
| 2008/0176299 A1 | 7/2008 | Dicosimo et al. |
| 2008/0176783 A1 | 7/2008 | DiCosimo et al. |
| 2009/0005590 A1 | 1/2009 | DiCosimo et al. |
| 2010/0048448 A1 | 2/2010 | Dicosimo et al. |
| 2010/0086510 A1 | 4/2010 | Dicosimo et al. |
| 2010/0086534 A1 | 4/2010 | Dicosimo et al. |
| 2010/0086621 A1 | 4/2010 | Dicosimo et al. |
| 2010/0087528 A1 | 4/2010 | Dicosimo et al. |
| 2010/0087529 A1 | 4/2010 | Dicosimo et al. |
| 2011/0081693 A1 | 4/2011 | Dicosimo et al. |

FOREIGN PATENT DOCUMENTS

| | | |
|---|---|---|
| EP | 0807156 B1 | 11/1997 |
| WO | WO96/32149 | 10/1996 |
| WO | WO97/41833 | 11/1997 |
| WO | WO99/03984 | 1/1999 |
| WO | WO00/61713 | 10/2000 |
| WO | WO02/22467 | 3/2002 |
| WO | WO2005/035705 A2 | 4/2005 |
| WO | WO2007/070609 A2 | 6/2007 |
| WO | WO2007/106293 A1 | 9/2007 |

(Continued)

OTHER PUBLICATIONS

Abbott et al., Physical Properties and Kinetic Behavior of a Cephalosporin . . . , Appl. Microbial. 30(3):413-419 (1975).
Belghith, Stabilization of Penicillium Occitanis Cellulases by Sray Drying in Presence .., Enzyme and Microbial Tech., 28 (2001) 253-258, XP-002558791.
Berman, H.M. et al., The Protein Data Bank. Nucleic Acids Research, 28 pp. 235-242 (2000).
H.M. Berman, Announcing the Worldwide Protein Data Bank, Nature Structural Biology 10 (12), p. 980 (2003).

(Continued)

*Primary Examiner* — Christian Fronda

(57) ABSTRACT

Disclosed herein is a method for stabilization of the perhydrolase activity of the CE-7 esterase in a formulation with a carboxylic acid ester that employs the addition of a buffering agent, substantially undissolved, to the mixture of the CE-7 esterase and the carboxylic acid ester. Further, disinfectant and laundry care formulations comprising the peracids produced by the processes described herein are provided.

17 Claims, No Drawings

FOREIGN PATENT DOCUMENTS

WO  WO2008/073139 A1  6/2008

OTHER PUBLICATIONS

Braeken, L. et al., Modeling of the Adsorption of Organic Compounds on Polymeric Nanofiltration Membranes in Solutions Containing . . . , Chem Phys Chem, 6:1606-1612 (2005).

Cardoza et al., A Cephalosporin C Acetylhydrolase is Present in the Cultures of Nocardia Lactamdurans, Appl. Microbiol. Biotechnol., 54(3):406-412 (2000).

Castillo et al., On the Activity Loss of Hydrolases in Organic Solvents . . . , J. Mol. Catalysis Elsevier, vol. 35, No. 4-6, pp. 147-153, Sep. 1, 2005.

Cowan et al., Biocatalysis in Organic Phase Media., Ch. 7 in Biocataiysis at Extreme Temperatures . . . , Amer. Chem. Soc. Symposium Series 498, pp. 86-107 (1992).

Degrassi et al., The Acetyl Xyland Esterase of *Bacillus pumilus* Belongs to a Family . . . , Microbiology., 146:1585-1591 (2000).

DiCosimo, Thermophilic Perhydrolases for Peracetic Acid Production, Sim Annual Meeting and Exhibition, XP0002557717, Jul. 30, 2009.

Fromant et al., Direct Random Mutagenesis of Gene-Sized DNA Fragments Using Polymerase Chain Reaction, Analytical Biochemistry 224, 347-353 (1995).

Funasaki, N. et al., Intramolecular Hydrophobic Association of Two Alkyl Chains of Ollgoethylene Glycol Diethers and Diesters in Water, J. Phys. Chem. 88:5786-5790 (198, (1984).

Gilbert et al., , Recent Advances in Carbohydrate Bioengineering, The Royal Society of Chemistry, Cambridge, pp. 3-12. (1999).

Gunning, Y. M. et al., Phase Behavior and Component Partitioning in Low Water Content Amorphous Carbohydrates . . . , J. Agric. Food Chem. 48:395-399 (2000).

Ikeda et al., Complete Genome Sequence and Comparative Analysis of the Industrial Microorganism *Streptomyces avermitilis*, Nat. Biotechnol. 21 (5), 526-531 (2003).

Justus Liebigs Annalen der Chemie; 105:206 (1858).

Kobayashi et al., Purification and Properties of an Alkaline Protease from Alkalophilic *Bacillus* sp. KSM-K16, Appl. Microbiol. Biotechnol. 43 (3), 473-481 (1995).

Krastanova et al., Heterologous Expression, Purificaiton, Crystallization, X-Ray Analysis and . . . , Biochimica ET Biophysica Acta, vol. 1748, No. 2, May 2005, pp. 222-230.

Kunst et al., The Complete Genome Sequence of the Gram-Positive Bacterium *Bacillus subtilis*, Nature 390:249-256 (1997).

Kuo, S-J. et al., Solvent Polarity Influences Product Selectivity of Lipase-Mediated Esterification Reactions in Microaqueous Media, J. Am. Oil Chem. Soc. 73:1427-1433 (1996).

C. Laane et al., Rules for Optimization of Biocatalysis in Organic Solvents, Biotechnol. Bioeng. 30:81-87 (1987).

Lee, Y.E. et al., Genetic Organization, Sequence and Biochemical Characterization of Recombinant . . . , J Gen Microbiol. (1993), 139:1235-1243.

Lin-Goerke et al., PCR-based Random Mutagenesis Using Manganese and Reduced dNTP Concentration, Biotechniques, 23(3):409-12 (1997).

Lorenz et al., Isolation, Analysis and Expresion of Two Genes from Thermoanaerobacterium . . . , J. Bacteriol 179:5436-5441 (1997).

Melnikov et al., Random Mutagenesis by Recombinational Capture of PCR Products in *Bacillus subtilis* and *Acinetobacter calcoaceticus*, Nucleic Acids Res. 27(4):1056-62 (1999).

Mitsushima et al Gene Cloning, Nucleotide Sequence, and Expression .., Appl. Env. Microbiol. 61(6):2224-2229, (1995).

Nelson et al., Evidence for Lateral Gene Transfer Between Archaea and Bacteria From Genome Sequence of *Thermotoga* Maritime, Nature, 399:323-329 (1999).

Nixon et al., Assembly of an Active Enzyme by the Linkage of Two Protein Modules, PNAS, 94:1069-1073 (1997).

Pinkernell, U. et al., Simultaneous HPLC Determination of Peroxyacetic Acid and Hydrogen Peroxide, Anal. Chem., 69(17):3623-3627 (1997).

Politino et al., Purification and Characterization of a Cephalosporin Esterase . . . , Appl. Environ. Microbiol., 63(12):4807-4811 (1997).

Rey et al., Complete Genome Sequence of the Industrial Bacterium *Bacillus* Licheniformis and . . . , Genome Biol., 5(10): article 77, R77.1—R77-12, (2004).

Ru et al, On the Salt-Induced Activation of Lyophilized Enzyme in Organic Solvents, J. Am. Chem. Soc. vol. 122, No. 8, pp. 1465-1571, Feb. 9, 2000.

Sakai et al., Purification and Properties of Cephalosporing-C Deacetylase from the Yeast . . . , J. Ferment. Bioeng. 85:53-57 (1998).

Seelig, Univ. Of Berlin Laboratory; 24: 3466 (1891).

Siezen et al., Genome-Scale Genotype-Phenotype Matching of Two *Lactococcus lactis* Isolates from Plants Identifies . . . , Appl. Environ. Microbiol. (2008) 74(2): 424-436).

Serdakowski et al., Enzyme Activation for Organic Solvents Made Easy, Treads in Biotechnology, Trends in Biotechnology, Review, vol . 26, No. 1, pp. 48-54, Nov. 26, 2007.

Stöchiometrie and Verwandtschaftslehre vol. 183, [K. Loskit, On the Knowledge of Triglycerides, p. 135-155], vol. 134, Nos. 1 and 2, May 1928.

Takami et al., Complete Genome Sequences of the Alkaliphilic Bacterium *Bacillus halodurans* and . . . , NAR, 28(21):4317-4331 (2000).

Vincent et al., Multifunctional Xylooligosaccharide/Cephalosporin C Deacetylase . . . , J. Mol. Biol., 330:593-606 (2003).

Wurtz, Annales de Chimie; 55:443 (1859).

Yoshii et al., Effects of protein on Retention of ADH enzyme Activity Encapsulated . . . , Journal of Food Engr., vol. 87, No. 1, pp. 34-39, Feb. 23, 2008.

Corresponding International Search Report and Written Opinion (PCT/ US2009/059232) dated Dec. 22, 2009.

U.S. Appl. No. 12/572,086, Restriction Requirement mailed Nov. 8, 2010.

U.S. Appl. No. 12/572,086, Non-Final Office Action mailed Dec. 9, 2010.

U.S. Appl. No. 12/572,086, Non-Final Office Action mailed Feb. 2, 2011.

U.S. Appl. No. 12/572,086, Notice of Allowance mailed Jul. 21, 2011.

SEQUENCE LISTING

<160> NUMBER OF SEQ ID NOS: 51

<210> SEQ ID NO 1
<211> LENGTH: 318
<212> TYPE: PRT
<213> ORGANISM: Bacillus subtilis

<400> SEQUENCE: 1

```
Met Gln Leu Phe Asp Leu Pro Leu Asp Gln Leu Gln Thr Tyr Lys Pro
1               5                   10                  15

Glu Lys Thr Ala Pro Lys Asp Phe Ser Glu Phe Trp Lys Leu Ser Leu
            20                  25                  30

Glu Glu Leu Ala Lys Val Gln Ala Glu Pro Asp Leu Gln Pro Val Asp
        35                  40                  45
```

Tyr Pro Ala Asp Gly Val Lys Val Tyr Arg Leu Thr Tyr Lys Ser Phe
            50                  55                  60

Gly Asn Ala Arg Ile Thr Gly Trp Tyr Ala Val Pro Asp Lys Gln Gly
 65                  70                  75                  80

Pro His Pro Ala Ile Val Lys Tyr His Gly Tyr Asn Ala Ser Tyr Asp
                    85                  90                  95

Gly Glu Ile His Glu Met Val Asn Trp Ala Leu His Gly Tyr Ala Ala
                100                 105                 110

Phe Gly Met Leu Val Arg Gly Gln Gln Ser Ser Glu Asp Thr Ser Ile
            115                 120                 125

Ser Leu His Gly His Ala Leu Gly Trp Met Thr Lys Gly Ile Leu Asp
    130                 135                 140

Lys Asp Thr Tyr Tyr Arg Gly Val Tyr Leu Asp Ala Val Arg Ala
145                 150                 155                 160

Leu Glu Val Ile Ser Ser Phe Asp Glu Val Asp Glu Thr Arg Ile Gly
                165                 170                 175

Val Thr Gly Gly Ser Gln Gly Gly Gly Leu Thr Ile Ala Ala Ala Ala
                180                 185                 190

Leu Ser Asp Ile Pro Lys Ala Ala Val Ala Asp Tyr Pro Tyr Leu Ser
            195                 200                 205

Asn Phe Glu Arg Ala Ile Asp Val Ala Leu Glu Gln Pro Tyr Leu Glu
210                 215                 220

Ile Asn Ser Phe Phe Arg Arg Asn Gly Ser Pro Glu Thr Glu Val Gln
225                 230                 235                 240

Ala Met Lys Thr Leu Ser Tyr Phe Asp Ile Met Asn Leu Ala Asp Arg
                245                 250                 255

Val Lys Val Pro Val Leu Met Ser Ile Gly Leu Ile Asp Lys Val Thr
                260                 265                 270

Pro Pro Ser Thr Val Phe Ala Ala Tyr Asn His Leu Glu Thr Glu Lys
            275                 280                 285

Glu Leu Lys Val Tyr Arg Tyr Phe Gly His Glu Tyr Ile Pro Ala Phe
    290                 295                 300

Gln Thr Glu Lys Leu Ala Phe Phe Lys Gln His Leu Lys Gly
305                 310                 315

<210> SEQ ID NO 2
<211> LENGTH: 318
<212> TYPE: PRT
<213> ORGANISM: Bacillus subtilis

<400> SEQUENCE: 2

Met Gln Leu Phe Asp Leu Pro Leu Asp Gln Leu Gln Thr Tyr Lys Pro
 1               5                  10                  15

Glu Lys Thr Thr Pro Asn Asp Phe Ser Glu Phe Trp Lys Ser Ser Leu
                20                  25                  30

Asp Glu Leu Ala Lys Val Lys Ala Ala Pro Asp Leu Gln Leu Val Asp
            35                  40                  45

Tyr Pro Ala Asp Gly Val Lys Val Tyr Arg Leu Thr Tyr Lys Ser Phe
            50                  55                  60

Gly Asn Ala Arg Ile Thr Gly Trp Tyr Ala Val Pro Asp Lys Glu Gly
 65                  70                  75                  80

Pro His Pro Ala Ile Val Lys Tyr His Gly Tyr Asn Ala Ser Tyr Asp
                    85                  90                  95

Gly Glu Ile His Glu Met Val Asn Trp Ala Leu His Gly Tyr Ala Ala
                100                 105                 110

```
Phe Gly Met Leu Val Arg Gly Gln Gln Ser Ser Glu Asp Thr Ser Ile
            115                 120                 125

Ser Pro His Gly His Ala Leu Gly Trp Met Thr Lys Gly Ile Leu Asp
        130                 135                 140

Lys Asp Thr Tyr Tyr Tyr Arg Gly Val Tyr Leu Asp Ala Val Arg Ala
145                 150                 155                 160

Leu Glu Val Ile Ser Ser Phe Asp Val Asp Glu Thr Arg Ile Gly
            165                 170                 175

Val Thr Gly Gly Ser Gln Gly Gly Gly Leu Thr Ile Ala Ala Ala Ala
            180                 185                 190

Leu Ser Asp Ile Pro Lys Ala Ala Val Ala Asp Tyr Pro Tyr Leu Ser
            195                 200                 205

Asn Phe Glu Arg Ala Ile Asp Val Ala Leu Glu Gln Pro Tyr Leu Glu
            210                 215                 220

Ile Asn Ser Phe Phe Arg Arg Asn Gly Ser Pro Glu Thr Glu Glu Lys
225                 230                 235                 240

Ala Met Lys Thr Leu Ser Tyr Phe Asp Ile Met Asn Leu Ala Asp Arg
                245                 250                 255

Val Lys Val Pro Val Leu Met Ser Ile Gly Leu Ile Asp Lys Val Thr
                260                 265                 270

Pro Pro Ser Thr Val Phe Ala Ala Tyr Asn His Leu Glu Thr Glu Lys
            275                 280                 285

Glu Leu Lys Val Tyr Arg Tyr Phe Gly His Glu Tyr Ile Pro Ala Phe
        290                 295                 300

Gln Thr Glu Lys Leu Ala Phe Phe Lys Gln His Leu Lys Gly
305                 310                 315

<210> SEQ ID NO 3
<211> LENGTH: 318
<212> TYPE: PRT
<213> ORGANISM: Bacillus licheniformis

<400> SEQUENCE: 3

Met Gln Gln Pro Tyr Asp Met Pro Leu Glu Gln Leu Tyr Gln Tyr Lys
1               5                   10                  15

Pro Glu Arg Thr Ala Pro Ala Asp Phe Lys Glu Phe Trp Lys Gly Ser
            20                  25                  30

Leu Glu Glu Leu Ala Asn Glu Lys Ala Gly Pro Gln Leu Glu Pro His
        35                  40                  45

Glu Tyr Pro Ala Asp Gly Val Lys Val Tyr Trp Leu Thr Tyr Arg Ser
    50                  55                  60

Ile Gly Gly Ala Arg Ile Lys Gly Trp Tyr Ala Val Pro Asp Arg Gln
65                  70                  75                  80

Gly Pro His Pro Ala Ile Val Lys Tyr His Gly Tyr Asn Ala Ser Tyr
                85                  90                  95

Asp Gly Asp Ile His Asp Ile Val Asn Trp Ala Leu His Gly Tyr Ala
            100                 105                 110

Ala Phe Gly Met Leu Val Arg Gly Gln Asn Ser Ser Glu Asp Thr Glu
        115                 120                 125

Ile Ser His His Gly His Val Pro Gly Trp Met Thr Lys Gly Ile Leu
    130                 135                 140

Asp Pro Lys Thr Tyr Tyr Tyr Arg Gly Val Tyr Leu Asp Ala Val Arg
145                 150                 155                 160

Ala Val Glu Val Val Ser Gly Phe Ala Glu Val Asp Glu Lys Arg Ile
                165                 170                 175
```

```
Gly Val Ile Gly Ala Ser Gln Gly Gly Leu Ala Val Ala Val Ser
                180                 185                 190

Ala Leu Ser Asp Ile Pro Lys Ala Ala Val Ser Glu Tyr Pro Tyr Leu
        195                 200                 205

Ser Asn Phe Gln Arg Ala Ile Asp Thr Ala Ile Asp Gln Pro Tyr Leu
210                 215                 220

Glu Ile Asn Ser Phe Phe Arg Arg Asn Thr Ser Pro Asp Ile Glu Gln
225                 230                 235                 240

Ala Ala Met His Thr Leu Ser Tyr Phe Asp Val Met Asn Leu Ala Gln
                245                 250                 255

Leu Val Lys Ala Thr Val Leu Met Ser Ile Gly Leu Val Asp Thr Ile
            260                 265                 270

Thr Pro Pro Ser Thr Val Phe Ala Ala Tyr Asn His Leu Glu Thr Asp
                275                 280                 285

Lys Glu Ile Lys Val Tyr Arg Tyr Phe Gly His Glu Tyr Ile Pro Pro
        290                 295                 300

Phe Gln Thr Glu Lys Leu Ala Phe Leu Arg Lys His Leu Lys
305                 310                 315

<210> SEQ ID NO 4
<211> LENGTH: 320
<212> TYPE: PRT
<213> ORGANISM: Bacillus pumilus

<400> SEQUENCE: 4

Met Gln Leu Phe Asp Leu Ser Leu Glu Glu Leu Lys Lys Tyr Lys Pro
1               5                   10                  15

Lys Lys Thr Ala Arg Pro Asp Phe Ser Asp Phe Trp Lys Lys Ser Leu
            20                  25                  30

Glu Glu Leu Arg Gln Val Glu Ala Glu Pro Thr Leu Glu Ser Tyr Asp
        35                  40                  45

Tyr Pro Val Lys Gly Val Lys Val Tyr Arg Leu Thr Tyr Gln Ser Phe
    50                  55                  60

Gly His Ser Lys Ile Glu Gly Phe Tyr Ala Val Pro Asp Gln Thr Gly
65                  70                  75                  80

Pro His Pro Ala Leu Val Arg Phe His Gly Tyr Asn Ala Ser Tyr Asp
                85                  90                  95

Gly Gly Ile His Asp Ile Val Asn Trp Ala Leu His Gly Tyr Ala Thr
            100                 105                 110

Phe Gly Met Leu Val Arg Gly Gln Gly Gly Ser Glu Asp Thr Ser Val
        115                 120                 125

Thr Pro Gly Gly His Ala Leu Gly Trp Met Thr Lys Gly Ile Leu Ser
    130                 135                 140

Lys Asp Thr Tyr Tyr Tyr Arg Gly Val Tyr Leu Asp Ala Val Arg Ala
145                 150                 155                 160

Leu Glu Val Ile Gln Ser Phe Pro Glu Val Asp Glu His Arg Ile Gly
                165                 170                 175

Val Ile Gly Gly Ser Gln Gly Gly Ala Leu Ala Ile Ala Ala Ala Ala
            180                 185                 190

Leu Ser Asp Ile Pro Lys Val Val Ala Asp Tyr Pro Tyr Leu Ser
        195                 200                 205

Asn Phe Glu Arg Ala Val Asp Val Ala Leu Glu Gln Pro Tyr Leu Glu
    210                 215                 220

Ile Asn Ser Tyr Phe Arg Arg Asn Ser Asp Pro Lys Val Glu Glu Lys
225                 230                 235                 240
```

```
Ala Phe Glu Thr Leu Ser Tyr Phe Asp Leu Ile Asn Leu Ala Gly Trp
                245                 250                 255

Val Lys Gln Pro Thr Leu Met Ala Ile Gly Leu Ile Asp Lys Ile Thr
            260                 265                 270

Pro Pro Ser Thr Val Phe Ala Ala Tyr Asn His Leu Glu Thr Asp Lys
            275                 280                 285

Asp Leu Lys Val Tyr Arg Tyr Phe Gly His Glu Phe Ile Pro Ala Phe
290                 295                 300

Gln Thr Glu Lys Leu Ser Phe Leu Gln Lys His Leu Leu Leu Ser Thr
305                 310                 315                 320

<210> SEQ ID NO 5
<211> LENGTH: 320
<212> TYPE: PRT
<213> ORGANISM: Clostridium thermocellum

<400> SEQUENCE: 5

Met Ala Gln Leu Tyr Asp Met Pro Leu Glu Glu Leu Lys Lys Tyr Lys
1               5                   10                  15

Pro Ala Leu Thr Lys Gln Lys Asp Phe Asp Glu Phe Trp Glu Lys Ser
            20                  25                  30

Leu Lys Glu Leu Ala Glu Ile Pro Leu Lys Tyr Gln Leu Ile Pro Tyr
        35                  40                  45

Asp Phe Pro Ala Arg Arg Val Lys Val Phe Arg Val Glu Tyr Leu Gly
    50                  55                  60

Phe Lys Gly Ala Asn Ile Glu Gly Trp Leu Ala Val Pro Glu Gly Glu
65                  70                  75                  80

Gly Leu Tyr Pro Gly Leu Val Gln Phe His Gly Tyr Asn Trp Ala Met
                85                  90                  95

Asp Gly Cys Val Pro Asp Val Val Asn Trp Ala Leu Asn Gly Tyr Ala
            100                 105                 110

Ala Phe Leu Met Leu Val Arg Gly Gln Gln Gly Arg Ser Val Asp Asn
        115                 120                 125

Ile Val Pro Gly Ser Gly His Ala Leu Gly Trp Met Ser Lys Gly Ile
    130                 135                 140

Leu Ser Pro Glu Glu Tyr Tyr Tyr Arg Gly Val Tyr Met Asp Ala Val
145                 150                 155                 160

Arg Ala Val Glu Ile Leu Ala Ser Leu Pro Cys Val Asp Glu Ser Arg
                165                 170                 175

Ile Gly Val Thr Gly Gly Ser Gln Gly Gly Gly Leu Ala Leu Ala Val
            180                 185                 190

Ala Ala Leu Ser Gly Ile Pro Lys Val Ala Ala Val His Tyr Pro Phe
        195                 200                 205

Leu Ala His Phe Glu Arg Ala Ile Asp Val Ala Pro Asp Gly Pro Tyr
    210                 215                 220

Leu Glu Ile Asn Glu Tyr Leu Arg Arg Asn Ser Gly Glu Glu Ile Glu
225                 230                 235                 240

Arg Gln Val Lys Lys Thr Leu Ser Tyr Phe Asp Ile Met Asn Leu Ala
                245                 250                 255

Pro Arg Ile Lys Cys Arg Thr Trp Ile Cys Thr Gly Leu Val Asp Glu
            260                 265                 270

Ile Thr Pro Pro Ser Thr Val Phe Ala Val Tyr Asn His Leu Lys Cys
        275                 280                 285

Pro Lys Glu Ile Ser Val Phe Arg Tyr Phe Gly His Glu His Met Pro
    290                 295                 300
```

```
Gly Ser Val Glu Ile Lys Leu Arg Ile Leu Met Asp Glu Leu Asn Pro
305                 310                 315                 320

<210> SEQ ID NO 6
<211> LENGTH: 325
<212> TYPE: PRT
<213> ORGANISM: Thermotoga neapolitana

<400> SEQUENCE: 6

Met Ala Phe Phe Asp Met Pro Leu Glu Glu Leu Lys Lys Tyr Arg Pro
1               5                   10                  15

Glu Arg Tyr Glu Glu Lys Asp Phe Asp Glu Phe Trp Arg Glu Thr Leu
            20                  25                  30

Lys Glu Ser Glu Gly Phe Pro Leu Asp Pro Val Phe Glu Lys Val Asp
35                  40                  45

Phe His Leu Lys Thr Val Glu Thr Tyr Asp Val Thr Phe Ser Gly Tyr
    50                  55                  60

Arg Gly Gln Arg Ile Lys Gly Trp Leu Leu Val Pro Lys Leu Ala Glu
65                  70                  75                  80

Glu Lys Leu Pro Cys Val Val Gln Tyr Ile Gly Tyr Asn Gly Gly Arg
                85                  90                  95

Gly Phe Pro His Asp Trp Leu Phe Trp Pro Ser Met Gly Tyr Ile Cys
            100                 105                 110

Phe Val Met Asp Thr Arg Gly Gln Gly Ser Gly Trp Met Lys Gly Asp
        115                 120                 125

Thr Pro Asp Tyr Pro Glu Gly Pro Val Asp Pro Gln Tyr Pro Gly Phe
130                 135                 140

Met Thr Arg Gly Ile Leu Asp Pro Gly Thr Tyr Tyr Tyr Arg Arg Val
145                 150                 155                 160

Phe Val Asp Ala Val Arg Ala Val Glu Ala Ala Ile Ser Phe Pro Arg
                165                 170                 175

Val Asp Ser Arg Lys Val Val Val Ala Gly Ser Gln Gly Gly Gly
            180                 185                 190

Ile Ala Leu Ala Val Ser Ala Leu Ser Asn Arg Val Lys Ala Leu Leu
        195                 200                 205

Cys Asp Val Pro Phe Leu Cys His Phe Arg Arg Ala Val Gln Leu Val
210                 215                 220

Asp Thr His Pro Tyr Val Glu Ile Thr Asn Phe Leu Lys Thr His Arg
225                 230                 235                 240

Asp Lys Glu Glu Ile Val Phe Arg Thr Leu Ser Tyr Phe Asp Gly Val
                245                 250                 255

Asn Phe Ala Ala Arg Ala Lys Val Pro Ala Leu Phe Ser Val Gly Leu
            260                 265                 270

Met Asp Thr Ile Cys Pro Pro Ser Thr Val Phe Ala Ala Tyr Asn His
        275                 280                 285

Tyr Ala Gly Pro Lys Glu Ile Arg Ile Tyr Pro Tyr Asn Asn His Glu
290                 295                 300

Gly Gly Gly Ser Phe Gln Ala Ile Glu Gln Val Lys Phe Leu Lys Arg
305                 310                 315                 320

Leu Phe Glu Glu Gly
                325

<210> SEQ ID NO 7
<211> LENGTH: 325
<212> TYPE: PRT
<213> ORGANISM: Thermotoga maritima
```

<400> SEQUENCE: 7

```
Met Ala Phe Phe Asp Leu Pro Leu Glu Glu Leu Lys Lys Tyr Arg Pro
1               5                   10                  15

Glu Arg Tyr Glu Glu Lys Asp Phe Asp Glu Phe Trp Glu Glu Thr Leu
            20                  25                  30

Ala Glu Ser Glu Lys Phe Pro Leu Asp Pro Val Phe Glu Arg Met Glu
        35                  40                  45

Ser His Leu Lys Thr Val Glu Ala Tyr Asp Val Thr Phe Ser Gly Tyr
    50                  55                  60

Arg Gly Gln Arg Ile Lys Gly Trp Leu Leu Val Pro Lys Leu Glu Glu
65                  70                  75                  80

Glu Lys Leu Pro Cys Val Val Gln Tyr Ile Gly Tyr Asn Gly Gly Arg
                85                  90                  95

Gly Phe Pro His Asp Trp Leu Phe Trp Pro Ser Met Gly Tyr Ile Cys
            100                 105                 110

Phe Val Met Asp Thr Arg Gly Gln Gly Ser Gly Trp Leu Lys Gly Asp
        115                 120                 125

Thr Pro Asp Tyr Pro Glu Gly Pro Val Asp Pro Gln Tyr Pro Gly Phe
    130                 135                 140

Met Thr Arg Gly Ile Leu Asp Pro Arg Thr Tyr Tyr Arg Arg Val
145                 150                 155                 160

Phe Thr Asp Ala Val Arg Ala Val Glu Ala Ala Ser Phe Pro Gln
                165                 170                 175

Val Asp Gln Glu Arg Ile Val Ile Ala Gly Ser Gly Gly Gly
            180                 185                 190

Ile Ala Leu Ala Val Ser Ala Leu Ser Lys Lys Ala Lys Ala Leu Leu
        195                 200                 205

Cys Asp Val Pro Phe Leu Cys His Phe Arg Arg Ala Val Gln Leu Val
210                 215                 220

Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Phe Asp Gly Val
                245                 250                 255

Asn Phe Ala Ala Arg Ala Lys Ile Pro Ala Leu Phe Ser Val Gly Leu
            260                 265                 270

Met Asp Asn Ile Cys Pro Pro Ser Thr Val Phe Ala Ala Tyr Asn Tyr
        275                 280                 285

Tyr Ala Gly Pro Lys Glu Ile Arg Ile Tyr Pro Tyr Asn Asn His Glu
    290                 295                 300

Gly Gly Gly Ser Phe Gln Ala Val Glu Gln Val Lys Phe Leu Lys Lys
305                 310                 315                 320

Leu Phe Glu Lys Gly
            325
```

<210> SEQ ID NO 8
<211> LENGTH: 320
<212> TYPE: PRT
<213> ORGANISM: Thermoanaerobacterium sp.

<400> SEQUENCE: 8

```
Met Gly Leu Phe Asp Met Pro Leu Gln Lys Leu Arg Glu Tyr Thr Gly
1               5                   10                  15

Thr Asn Pro Cys Pro Glu Asp Phe Asp Glu Tyr Trp Asn Arg Ala Leu
            20                  25                  30
```

```
Asp Glu Met Arg Ser Val Asp Pro Lys Ile Glu Leu Lys Glu Ser Ser
         35                  40                  45

Phe Gln Val Ser Phe Ala Glu Cys Tyr Asp Leu Tyr Phe Thr Gly Val
 50                  55                  60

Arg Gly Ala Arg Ile His Ala Lys Tyr Ile Lys Pro Lys Thr Glu Gly
 65                  70                  75                  80

Lys His Pro Ala Leu Ile Arg Phe His Gly Tyr Ser Ser Asn Ser Gly
                 85                  90                  95

Asp Trp Asn Asp Lys Leu Asn Tyr Val Ala Ala Gly Phe Thr Val Val
                100                 105                 110

Ala Met Asp Val Arg Gly Gln Gly Gln Ser Gln Val Gly Gly
            115                 120                 125

Val Thr Gly Asn Thr Leu Asn Gly His Ile Ile Arg Gly Leu Asp Asp
            130                 135                 140

Asp Ala Asp Asn Met Leu Phe Arg His Ile Phe Leu Asp Thr Ala Gln
145                 150                 155                 160

Leu Ala Gly Ile Val Met Asn Met Pro Glu Val Asp Glu Asp Arg Val
                165                 170                 175

Gly Val Met Gly Pro Ser Gln Gly Gly Gly Leu Ser Leu Ala Cys Ala
                180                 185                 190

Ala Leu Glu Pro Arg Val Arg Lys Val Val Ser Glu Tyr Pro Phe Leu
                195                 200                 205

Ser Asp Tyr Lys Arg Val Trp Asp Leu Asp Leu Ala Lys Asn Ala Tyr
210                 215                 220

Gln Glu Ile Thr Asp Tyr Phe Arg Leu Phe Asp Pro Arg His Glu Arg
225                 230                 235                 240

Glu Asn Glu Val Phe Thr Lys Leu Gly Tyr Ile Asp Val Lys Asn Leu
                245                 250                 255

Ala Lys Arg Ile Lys Gly Asp Val Leu Met Cys Val Gly Leu Met Asp
                260                 265                 270

Gln Val Cys Pro Pro Ser Thr Val Phe Ala Ala Tyr Asn Asn Ile Gln
                275                 280                 285

Ser Lys Lys Asp Ile Lys Val Tyr Pro Asp Tyr Gly His Glu Pro Met
290                 295                 300

Arg Gly Phe Gly Asp Leu Ala Met Gln Phe Met Leu Glu Leu Tyr Ser
305                 310                 315                 320

<210> SEQ ID NO 9
<211> LENGTH: 325
<212> TYPE: PRT
<213> ORGANISM: Bacillus sp.

<400> SEQUENCE: 9

Met Asn Leu Phe Asp Met Pro Leu Glu Glu Leu Gln His Tyr Lys Pro
 1               5                  10                  15

Ala Gln Thr Arg Gln Asp Asp Phe Glu Ser Phe Trp Lys Lys Arg Ile
                 20                  25                  30

Glu Glu Asn Ser Gln Tyr Pro Leu Asn Ile Glu Val Met Glu Arg Val
             35                  40                  45

Tyr Pro Val Pro Gly Val Arg Val Tyr Asp Ile Tyr Phe Asp Gly Phe
 50                  55                  60

Arg Asn Ser Arg Ile His Gly Val Tyr Val Thr Pro Glu Thr Pro Gly
 65                  70                  75                  80

Ala Asp Thr Pro Ala Ala Val Ile Phe His Gly Tyr Asn Trp Asn Thr
                 85                  90                  95
```

```
Leu Gln Pro His Tyr Ser Phe Lys His Val Ile Gln Gly Ile Pro Val
                100                 105                 110
Leu Met Val Glu Val Arg Gly Gln Asn Leu Leu Ser Pro Asp Arg Asn
            115                 120                 125
His Tyr Gly Asn Gly Gly Pro Gly Gly Trp Met Thr Leu Gly Val Met
130                 135                 140
Asp Pro Asp Gln Tyr Tyr Tyr Ser Leu Val Tyr Met Asp Cys Phe Arg
145                 150                 155                 160
Ser Ile Asp Ala Val Arg Glu Leu Ser Arg Lys Arg Ser Val Phe Val
                165                 170                 175
Glu Gly Gly Ser Gln Gly Gly Ala Leu Ala Ile Ala Ala Ala Ala Leu
            180                 185                 190
Gln Asp Asp Ile Leu Leu Ala Leu Ala Asp Ile Pro Phe Leu Thr His
        195                 200                 205
Phe Lys Arg Ser Val Glu Leu Ser Ser Asp Gly Pro Tyr Gln Glu Ile
210                 215                 220
Ser His Tyr Phe Lys Val His Asp Pro Leu His Gln Thr Glu Glu Gln
225                 230                 235                 240
Val Tyr Gln Thr Leu Ser Tyr Val Asp Cys Met Asn Met Ala Ser Met
                245                 250                 255
Val Glu Cys Pro Val Leu Leu Ser Ala Gly Leu Glu Asp Ile Val Cys
            260                 265                 270
Pro Pro Ser Ser Ala Phe Ala Leu Phe Asn His Leu Gly Gly Pro Lys
        275                 280                 285
Glu Ile Arg Ala Tyr Pro Glu Tyr Ala His Glu Val Pro Ala Val His
290                 295                 300
Glu Glu Glu Lys Leu Lys Phe Ile Ser Ser Arg Leu Lys Asn Arg Glu
305                 310                 315                 320
Lys Arg Cys Arg Pro
            325

<210> SEQ ID NO 10
<211> LENGTH: 319
<212> TYPE: PRT
<213> ORGANISM: Bacillus halodurans

<400> SEQUENCE: 10

Met Pro Leu Ile Asp Met Pro Leu Thr Glu Leu Lys Glu Tyr Met Gly
1               5                   10                  15
Arg Asn Pro Lys Pro Asp Asp Phe Thr Glu Tyr Trp Asp Arg Ala Leu
            20                  25                  30
Gln Glu Met Arg Lys Val Asn Pro Asn Val Glu Leu Ile Pro Ser Asp
        35                  40                  45
Phe Gln Thr Thr Tyr Ala Glu Cys Phe His Leu Tyr Phe Thr Gly Val
50                  55                  60
Arg Gly Ala Arg Ile His Ala Lys Tyr Val Arg Pro Arg His Thr Ser
65                  70                  75                  80
Gly Thr His Pro Ala Val Ile His Phe His Gly Tyr Thr Met Asn Ala
                85                  90                  95
Gly Glu Trp Thr Gly Leu Leu His Tyr Ala Ala Leu Gly Tyr Ser Val
            100                 105                 110
Leu Ala Met Asp Val Arg Gly Gln Gly Gly Leu Ser Glu Asp Thr Gly
        115                 120                 125
Gly Val Lys Gly Asn Thr His Ser Gly His Ile Ile Arg Gly Leu Asp
130                 135                 140
```

```
Asp Asn Ala Asp Gln Leu Leu Phe Arg His Val Phe Leu Asp Thr Ala
145                 150                 155                 160

Gln Leu Ala Asn Ile Val Met Asn Leu Pro Glu Val Asp Glu Glu Arg
                165                 170                 175

Val Ala Val Thr Gly Trp Ser Gln Gly Gly Ala Leu Ala Ile Ala Cys
            180                 185                 190

Ala Ala Leu Glu Pro Lys Ile Lys Lys Val Ala Pro Val Tyr Pro Phe
        195                 200                 205

Leu Ser Asp Tyr Gln Arg Val Trp Glu Met Asp Leu Ala Glu Lys Ala
    210                 215                 220

Tyr Asp Glu Leu Gln Thr Tyr Phe Arg Arg Phe Asp Pro Gln His Arg
225                 230                 235                 240

Arg Glu Ala Glu Ile Phe Thr Lys Leu Gly Tyr Ile Asp Ile Gln His
                245                 250                 255

Leu Ala Pro Leu Val Lys Gly Glu Val Leu Leu Ala Val Gly Leu Met
            260                 265                 270

Asp Thr Val Cys Pro Pro Ser Thr Gln Phe Ala Met Tyr Asn Lys Leu
        275                 280                 285

Thr Thr Thr Lys Ser Ile Glu Leu Tyr Pro Asp Phe Ala His Glu Asp
    290                 295                 300

Leu Pro Gly His Arg Asp Arg Ile Phe Gln Phe Leu Ser Asp Leu
305                 310                 315

<210> SEQ ID NO 11
<211> LENGTH: 317
<212> TYPE: PRT
<213> ORGANISM: Bacillus clausii

<400> SEQUENCE: 11

Met Pro Leu Val Asp Met Pro Leu Arg Glu Leu Leu Ala Tyr Glu Gly
1               5                   10                  15

Ile Asn Pro Lys Pro Ala Asp Phe Asp Gln Tyr Trp Asn Arg Ala Lys
            20                  25                  30

Thr Glu Ile Glu Ala Ile Asp Pro Glu Val Thr Leu Val Glu Ser Ser
        35                  40                  45

Phe Gln Cys Ser Phe Ala Asn Cys Tyr His Tyr Tyr Arg Ser Ala
    50                  55                  60

Gly Asn Ala Lys Ile His Ala Lys Tyr Val Gln Pro Lys Ala Gly Glu
65              70                  75                  80

Lys Thr Pro Ala Val Phe Met Phe His Gly Tyr Gly Gly Arg Ser Ala
            85                  90                  95

Glu Trp Ser Ser Leu Leu Asn Tyr Val Ala Ala Gly Phe Ser Val Phe
        100                 105                 110

Tyr Met Asp Val Arg Gly Gln Gly Gly Thr Ser Glu Asp Pro Gly Gly
    115                 120                 125

Val Arg Gly Asn Thr Tyr Arg Gly His Ile Ile Arg Gly Leu Asp Ala
130                 135                 140

Gly Pro Asp Ala Leu Phe Tyr Arg Ser Val Phe Leu Asp Thr Val Gln
145                 150                 155                 160

Leu Val Arg Ala Ala Lys Thr Leu Pro His Ile Asp Lys Thr Arg Leu
                165                 170                 175

Met Ala Thr Gly Trp Ser Gln Gly Gly Ala Leu Thr Leu Ala Cys Ala
            180                 185                 190

Ala Leu Val Pro Glu Ile Lys Arg Leu Ala Pro Val Tyr Pro Phe Leu
        195                 200                 205
```

```
Ser Asp Tyr Lys Arg Val Trp Gln Met Asp Leu Ala Val Arg Ser Tyr
        210                 215                 220
Lys Glu Leu Ala Asp Tyr Phe Arg Ser Tyr Asp Pro Gln His Lys Arg
225                 230                 235                 240
His Gly Glu Ile Phe Glu Arg Leu Gly Tyr Ile Asp Val Gln His Leu
                245                 250                 255
Ala Asp Arg Ile Gln Gly Asp Val Leu Met Gly Val Gly Leu Met Asp
            260                 265                 270
Thr Glu Cys Pro Pro Ser Thr Gln Phe Ala Ala Tyr Asn Lys Ile Lys
        275                 280                 285
Ala Lys Lys Ser Tyr Glu Leu Tyr Pro Asp Phe Gly His Glu His Leu
    290                 295                 300
Pro Gly Met Asn Asp His Ile Phe Arg Phe Phe Thr Ser
305                 310                 315

<210> SEQ ID NO 12
<211> LENGTH: 318
<212> TYPE: PRT
<213> ORGANISM: Bacillus subtilis

<400> SEQUENCE: 12

Met Gln Leu Phe Asp Leu Pro Leu Asp Gln Leu Gln Thr Tyr Lys Pro
1               5                   10                  15
Glu Lys Thr Ala Pro Lys Asp Phe Ser Glu Phe Trp Lys Leu Ser Leu
                20                  25                  30
Glu Glu Leu Ala Lys Val Gln Ala Glu Pro Asp Leu Gln Pro Val Asp
            35                  40                  45
Tyr Pro Ala Asp Gly Val Lys Val Tyr Arg Leu Thr Tyr Lys Ser Phe
50                  55                  60
Gly Asn Ala Arg Ile Thr Gly Trp Tyr Ala Val Pro Asp Lys Gln Gly
65                  70                  75                  80
Pro His Pro Ala Ile Val Lys Tyr His Gly Tyr Asn Ala Ser Tyr Asp
                85                  90                  95
Gly Glu Ile His Glu Met Val Asn Trp Ala Leu His Gly Tyr Ala Ala
            100                 105                 110
Phe Gly Met Leu Val Arg Gly Gln Gln Ser Ser Glu Asp Thr Ser Ile
        115                 120                 125
Ser Pro His Gly His Ala Leu Gly Trp Met Thr Lys Gly Ile Leu Asp
    130                 135                 140
Lys Asp Thr Tyr Tyr Tyr Arg Gly Val Tyr Leu Asp Ala Val Arg Ala
145                 150                 155                 160
Leu Glu Val Ile Ser Ser Phe Asp Glu Val Asp Glu Thr Arg Ile Gly
                165                 170                 175
Val Thr Gly Gly Ser Gln Gly Gly Gly Leu Thr Ile Ala Ala Ala Ala
            180                 185                 190
Leu Ser Asp Ile Pro Lys Ala Ala Val Ala Asp Tyr Pro Tyr Leu Ser
        195                 200                 205
Asn Phe Glu Arg Ala Ile Asp Val Ala Leu Glu Gln Pro Tyr Leu Glu
    210                 215                 220
Ile Asn Ser Phe Phe Arg Arg Asn Gly Ser Pro Glu Thr Glu Val Gln
225                 230                 235                 240
Ala Met Lys Thr Leu Ser Tyr Phe Asp Ile Met Asn Leu Ala Asp Arg
                245                 250                 255
Val Lys Val Pro Val Leu Met Ser Ile Gly Leu Ile Asp Lys Val Thr
            260                 265                 270
```

Pro Pro Ser Thr Val Phe Ala Ala Tyr Asn His Leu Glu Thr Glu Lys
        275                 280                 285

Glu Leu Lys Val Tyr Arg Tyr Phe Gly His Glu Tyr Ile Pro Ala Phe
290                 295                 300

Gln Thr Glu Lys Leu Ala Phe Phe Lys Gln His Leu Lys Gly
305                 310                 315

<210> SEQ ID NO 13
<211> LENGTH: 320
<212> TYPE: PRT
<213> ORGANISM: Thermoanearobacerium saccharolyticum

<400> SEQUENCE: 13

Met Gly Leu Phe Asp Met Pro Leu Gln Lys Leu Arg Glu Tyr Thr Gly
1               5                   10                  15

Thr Asn Pro Cys Pro Glu Asp Phe Asp Glu Tyr Trp Asp Arg Ala Leu
            20                  25                  30

Asp Glu Met Arg Ser Val Asp Pro Lys Ile Lys Met Lys Lys Ser Ser
        35                  40                  45

Phe Gln Val Pro Phe Ala Glu Cys Tyr Asp Leu Tyr Phe Thr Gly Val
    50                  55                  60

Arg Gly Ala Arg Ile His Ala Lys Tyr Ile Arg Pro Lys Thr Glu Gly
65                  70                  75                  80

Lys His Pro Ala Leu Ile Arg Phe His Gly Tyr Ser Ser Asn Ser Gly
                85                  90                  95

Asp Trp Asn Asp Lys Leu Asn Tyr Val Ala Ala Gly Phe Thr Val Val
            100                 105                 110

Ala Met Asp Ala Arg Gly Gln Gly Gly Gln Ser Gln Asp Val Gly Gly
        115                 120                 125

Val Asn Gly Asn Thr Leu Asn Gly His Ile Ile Arg Gly Leu Asp Asp
    130                 135                 140

Asp Ala Asp Asn Met Leu Phe Arg His Ile Phe Leu Asp Thr Ala Gln
145                 150                 155                 160

Leu Ala Gly Ile Val Met Asn Met Pro Glu Ile Asp Glu Asp Arg Val
                165                 170                 175

Ala Val Met Gly Pro Ser Gln Gly Gly Gly Leu Ser Leu Ala Cys Ala
            180                 185                 190

Ala Leu Glu Pro Lys Ile Arg Lys Val Val Ser Glu Tyr Pro Phe Leu
        195                 200                 205

Ser Asp Tyr Lys Arg Val Trp Asp Leu Asp Leu Ala Lys Asn Ala Tyr
    210                 215                 220

Gln Glu Ile Thr Asp Tyr Phe Arg Leu Phe Asp Pro Arg His Glu Arg
225                 230                 235                 240

Glu Asn Glu Val Phe Thr Lys Leu Gly Tyr Ile Asp Val Lys Asn Leu
                245                 250                 255

Ala Lys Arg Ile Lys Gly Asp Val Leu Met Cys Val Gly Leu Met Asp
            260                 265                 270

Gln Val Cys Pro Pro Ser Thr Val Phe Ala Ala Tyr Asn Asn Ile Gln
        275                 280                 285

Ser Lys Lys Asp Ile Lys Val Tyr Pro Asp Tyr Gly His Glu Pro Met
    290                 295                 300

Arg Gly Phe Gly Asp Leu Ala Met Gln Phe Met Leu Glu Leu Tyr Ser
305                 310                 315                 320

<210> SEQ ID NO 14
<211> LENGTH: 326

<212> TYPE: PRT
<213> ORGANISM: Thermotoga lettingae

<400> SEQUENCE: 14

Met Val Tyr Phe Asp Met Pro Leu Glu Asp Leu Arg Lys Tyr Leu Pro
1               5                   10                  15

Gln Arg Tyr Glu Glu Lys Asp Phe Asp Asp Phe Trp Lys Gln Thr Ile
            20                  25                  30

His Glu Thr Arg Gly Tyr Phe Gln Glu Pro Ile Leu Lys Lys Val Asp
        35                  40                  45

Phe Tyr Leu Gln Asn Val Glu Thr Phe Asp Val Thr Phe Ser Gly Tyr
    50                  55                  60

Arg Gly Gln Lys Ile Lys Gly Trp Leu Ile Leu Pro Lys Phe Arg Asn
65                  70                  75                  80

Gly Lys Leu Pro Cys Val Val Glu Phe Val Gly Tyr Gly Gly Gly Arg
                85                  90                  95

Gly Phe Pro Tyr Asp Trp Leu Leu Trp Ser Ala Ala Gly Tyr Ala His
            100                 105                 110

Phe Ile Met Asp Thr Arg Gly Gln Gly Ser Asn Trp Met Lys Gly Asp
        115                 120                 125

Thr Pro Asp Tyr Glu Asp Asn Pro Ser Asp Pro Gln Tyr Pro Gly Phe
    130                 135                 140

Leu Thr Lys Gly Val Leu Asn Pro Glu Thr Tyr Tyr Tyr Arg Arg Val
145                 150                 155                 160

Phe Met Asp Ala Phe Met Ala Val Glu Thr Ile Ser Gln Leu Glu Gln
                165                 170                 175

Ile Asp Ser Gln Thr Ile Ile Leu Ser Gly Ala Ser Gln Gly Gly Gly
            180                 185                 190

Ile Ala Leu Ala Val Ser Ala Leu Ser Ser Lys Val Met Ala Leu Leu
        195                 200                 205

Cys Asp Val Pro Phe Leu Cys His Tyr Lys Arg Ala Val Gln Ile Thr
    210                 215                 220

Asp Ser Met Pro Tyr Ala Glu Ile Thr Arg Tyr Cys Lys Thr His Ile
225                 230                 235                 240

Asp Lys Ile Gln Thr Val Phe Arg Thr Leu Ser Tyr Phe Asp Gly Val
                245                 250                 255

Asn Phe Ala Ala Arg Ala Lys Cys Pro Ala Leu Phe Ser Val Gly Leu
            260                 265                 270

Met Asp Asp Ile Cys Pro Pro Ser Thr Val Phe Ala Ala Tyr Asn Tyr
        275                 280                 285

Tyr Ala Gly Glu Lys Asp Ile Arg Ile Tyr Pro Tyr Asn Asn His Glu
    290                 295                 300

Gly Gly Gly Ser Phe His Thr Leu Glu Lys Leu Lys Phe Val Lys Lys
305                 310                 315                 320

Thr Ile Ser Met Arg Glu
            325

<210> SEQ ID NO 15
<211> LENGTH: 325
<212> TYPE: PRT
<213> ORGANISM: Thermotoga petrophila

<400> SEQUENCE: 15

Met Ala Phe Phe Asp Leu Pro Leu Glu Glu Leu Lys Lys Tyr Arg Pro
1               5                   10                  15

Glu Arg Tyr Glu Glu Lys Asp Phe Asp Glu Phe Trp Glu Gly Thr Leu

```
                      20                  25                  30
Ala Glu Asn Glu Lys Phe Pro Leu Asp Pro Val Phe Glu Arg Met Glu
                35                  40                  45

Ser His Leu Lys Thr Val Glu Ala Tyr Asp Val Thr Phe Ser Gly Tyr
            50                  55                  60

Met Gly Gln Arg Ile Lys Gly Trp Leu Leu Val Pro Lys Leu Glu Glu
65                  70                  75                  80

Glu Lys Leu Pro Cys Val Val Gln Tyr Ile Gly Tyr Asn Gly Gly Arg
                85                  90                  95

Gly Phe Pro His Asp Trp Leu Phe Trp Pro Ser Met Gly Tyr Ile Cys
                100                 105                 110

Phe Val Met Asp Thr Arg Gly Gln Gly Ser Gly Trp Met Lys Gly Asp
                115                 120                 125

Thr Pro Asp Tyr Pro Glu Asp Pro Val Asp Pro Gln Tyr Pro Gly Phe
                130                 135                 140

Met Thr Arg Gly Ile Leu Asp Pro Arg Thr Tyr Tyr Arg Arg Val
145                 150                 155                 160

Phe Thr Asp Ala Val Arg Ala Val Glu Ala Ala Ser Phe Pro Arg
                165                 170                 175

Val Asp His Glu Arg Ile Val Ile Ala Gly Ser Gln Gly Gly Gly
                180                 185                 190

Ile Ala Leu Ala Val Ser Ala Leu Ser Lys Ala Lys Ala Leu Leu
                195                 200                 205

Cys Asp Val Pro Phe Leu Cys His Phe Arg Arg Ala Val Gln Leu Val
                210                 215                 220

Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Phe Asp Gly Val
                245                 250                 255

Asn Phe Ala Val Arg Ala Lys Ile Pro Ala Leu Phe Ser Val Gly Leu
                260                 265                 270

Met Asp Asn Ile Cys Pro Pro Ser Thr Val Phe Ala Ala Tyr Asn His
                275                 280                 285

Tyr Ala Gly Pro Lys Glu Ile Arg Ile Tyr Pro Tyr Asn Asn His Glu
                290                 295                 300

Gly Gly Gly Ser Phe Gln Ala Ile Glu Gln Val Lys Phe Leu Lys Arg
305                 310                 315                 320

Leu Phe Glu Lys Gly
                325

<210> SEQ ID NO 16
<211> LENGTH: 325
<212> TYPE: PRT
<213> ORGANISM: Thermotoga sp.

<400> SEQUENCE: 16

Met Ala Phe Phe Asp Leu Pro Leu Glu Glu Leu Lys Lys Tyr Arg Pro
1               5                   10                  15

Glu Arg Tyr Glu Glu Lys Asp Phe Asp Glu Phe Trp Lys Glu Thr Leu
                20                  25                  30

Ala Glu Ser Glu Lys Phe Pro Leu Asp Pro Val Phe Glu Arg Met Glu
                35                  40                  45

Ser His Leu Lys Thr Val Glu Val Tyr Asp Val Thr Phe Ser Gly Tyr
            50                  55                  60

Arg Gly Gln Arg Ile Lys Gly Trp Leu Leu Val Pro Lys Leu Glu Glu
```

```
                65                  70                  75                  80
Glu Lys Leu Pro Cys Val Val Gln Tyr Ile Gly Tyr Asn Gly Gly Arg
                85                  90                  95

Gly Phe Pro His Asp Trp Leu Phe Trp Pro Ser Met Gly Tyr Ile Cys
            100                 105                 110

Phe Val Met Asp Thr Arg Gly Gln Gly Ser Gly Trp Leu Lys Gly Asp
        115                 120                 125

Thr Pro Asp Tyr Pro Glu Asp Pro Val Asp Pro Gln Tyr Pro Gly Phe
    130                 135                 140

Met Thr Arg Gly Ile Leu Asp Pro Arg Thr Tyr Tyr Arg Arg Val
145                 150                 155                 160

Phe Thr Asp Ala Val Arg Ala Val Glu Ala Ala Ser Phe Pro Arg
                165                 170                 175

Val Asp His Glu Arg Ile Val Ile Ala Gly Ser Gln Gly Gly
                180                 185                 190

Ile Ala Leu Ala Val Ser Ala Leu Ser Lys Lys Ala Lys Ala Leu Leu
                195                 200                 205

Cys Asp Val Pro Phe Leu Cys His Phe Arg Arg Ala Val Gln Leu Val
    210                 215                 220

Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Phe Asp Gly Val
                245                 250                 255

Asn Phe Ala Val Arg Ala Lys Ile Pro Ala Leu Phe Ser Val Gly Leu
                260                 265                 270

Met Asp Asn Ile Cys Pro Pro Ser Thr Val Phe Ala Ala Tyr Asn His
            275                 280                 285

Tyr Ala Gly Pro Lys Glu Ile Arg Ile Tyr Pro Tyr Asn Asn His Glu
        290                 295                 300

Gly Gly Gly Ser Phe Gln Ala Ile Glu Gln Val Lys Phe Leu Lys Arg
305                 310                 315                 320

Leu Phe Glu Lys Gly
            325

<210> SEQ ID NO 17
<211> LENGTH: 279
<212> TYPE: PRT
<213> ORGANISM: Thermotoga sp.

<400> SEQUENCE: 17

Met Ala Leu Phe Asp Met Pro Leu Glu Lys Leu Arg Ser Tyr Leu Pro
1               5                  10                  15

Asp Arg Tyr Glu Glu Asp Phe Asp Leu Phe Trp Lys Glu Thr Leu
                20                  25                  30

Glu Glu Ser Arg Lys Phe Pro Leu Asp Pro Ile Phe Glu Arg Val Asp
            35                  40                  45

Tyr Leu Leu Glu Asn Val Glu Val Tyr Asp Val Thr Phe Ser Gly Tyr
        50                  55                  60

Arg Gly Gln Arg Ile Lys Ala Trp Leu Ile Leu Pro Val Val Lys Lys
65                  70                  75                  80

Glu Glu Arg Leu Pro Cys Ile Val Glu Phe Ile Gly Tyr Arg Gly Gly
                85                  90                  95

Arg Gly Phe Pro Phe Asp Trp Leu Phe Trp Ser Ser Ala Gly Tyr Ala
            100                 105                 110

His Phe Val Met Asp Thr Arg Gly Gln Gly Thr Ser Arg Val Lys Gly
```

```
              115                 120                 125
Asp Thr Pro Asp Tyr Cys Asp Glu Pro Ile Asn Pro Gln Phe Pro Gly
        130                 135                 140

Phe Met Thr Arg Gly Ile Leu Asp Pro Arg Thr Tyr Tyr Arg Arg
145                 150                 155                 160

Val Phe Thr Asp Ala Val Arg Ala Val Glu Thr Ala Ser Ser Phe Pro
                165                 170                 175

Gly Ile Asp Pro Glu Arg Ile Ala Val Val Gly Thr Ser Gln Gly Gly
            180                 185                 190

Gly Ile Ala Leu Ala Val Ala Ala Leu Ser Glu Ile Pro Lys Ala Leu
        195                 200                 205

Val Ser Asn Val Pro Phe Leu Cys His Phe Arg Arg Ala Val Gln Ile
    210                 215                 220

Thr Asp Asn Ala Pro Tyr Ser Glu Ile Val Asn Tyr Leu Lys Val His
225                 230                 235                 240

Arg Asp Lys Glu Glu Ile Val Phe Arg Thr Leu Ser Tyr Phe Asp Gly
                245                 250                 255

Val Asn Phe Ala Ala Arg Ala Lys Ile Pro Ala Leu Phe Ser Val Ala
            260                 265                 270

Leu Met Asp Lys Thr Cys Pro
        275

<210> SEQ ID NO 18
<211> LENGTH: 182
<212> TYPE: PRT
<213> ORGANISM: Bacillus subtilis

<400> SEQUENCE: 18

Arg Gly Gln Gln Ser Ser Glu Asp Thr Ser Ile Ser Leu His Gly His
1               5                   10                  15

Ala Leu Gly Trp Met Thr Lys Gly Ile Leu Asp Lys Asp Thr Tyr Tyr
            20                  25                  30

Tyr Arg Gly Val Tyr Leu Asp Ala Val Arg Ala Leu Glu Val Ile Ser
        35                  40                  45

Ser Phe Asp Glu Val Asp Glu Thr Arg Ile Gly Val Thr Gly Gly Ser
    50                  55                  60

Gln Gly Gly Gly Leu Thr Ile Ala Ala Ala Ala Leu Ser Asp Ile Pro
65                  70                  75                  80

Lys Ala Ala Val Ala Asp Tyr Pro Tyr Leu Ser Asn Phe Glu Arg Ala
                85                  90                  95

Ile Asp Val Ala Leu Glu Gln Pro Tyr Leu Glu Ile Asn Ser Phe Phe
            100                 105                 110

Arg Arg Asn Gly Ser Pro Glu Thr Glu Val Gln Ala Met Lys Thr Leu
        115                 120                 125

Ser Tyr Phe Asp Ile Met Asn Leu Ala Asp Arg Val Lys Val Pro Val
    130                 135                 140

Leu Met Ser Ile Gly Leu Ile Asp Lys Val Thr Pro Pro Ser Thr Val
145                 150                 155                 160

Phe Ala Ala Tyr Asn His Leu Glu Thr Glu Lys Glu Leu Lys Val Tyr
                165                 170                 175

Arg Tyr Phe Gly His Glu
            180

<210> SEQ ID NO 19
<211> LENGTH: 325
<212> TYPE: PRT
```

<213> ORGANISM: Thermotoga neapolitana
<220> FEATURE:
<221> NAME/KEY: MISC_FEATURE
<222> LOCATION: (277)..(277)
<223> OTHER INFORMATION: Xaa is Ala, Val, Ser, or Thr.

<400> SEQUENCE: 19

Met Ala Phe Phe Asp Met Pro Leu Glu Glu Leu Lys Lys Tyr Arg Pro
1               5                   10                  15

Glu Arg Tyr Glu Glu Lys Asp Phe Asp Glu Phe Trp Arg Glu Thr Leu
            20                  25                  30

Lys Glu Ser Glu Gly Phe Pro Leu Asp Pro Val Phe Glu Lys Val Asp
        35                  40                  45

Phe His Leu Lys Thr Val Glu Thr Tyr Asp Val Thr Phe Ser Gly Tyr
    50                  55                  60

Arg Gly Gln Arg Ile Lys Gly Trp Leu Leu Val Pro Lys Leu Ala Glu
65                  70                  75                  80

Glu Lys Leu Pro Cys Val Val Gln Tyr Ile Gly Tyr Asn Gly Gly Arg
                85                  90                  95

Gly Phe Pro His Asp Trp Leu Phe Trp Pro Ser Met Gly Tyr Ile Cys
            100                 105                 110

Phe Val Met Asp Thr Arg Gly Gln Gly Ser Gly Trp Met Lys Gly Asp
        115                 120                 125

Thr Pro Asp Tyr Pro Glu Gly Pro Val Asp Pro Gln Tyr Pro Gly Phe
    130                 135                 140

Met Thr Arg Gly Ile Leu Asp Pro Gly Thr Tyr Tyr Tyr Arg Arg Val
145                 150                 155                 160

Phe Val Asp Ala Val Arg Ala Val Glu Ala Ala Ile Ser Phe Pro Arg
                165                 170                 175

Val Asp Ser Arg Lys Val Val Ala Gly Ser Gln Gly Gly Gly
            180                 185                 190

Ile Ala Leu Ala Val Ser Ala Leu Ser Asn Arg Val Lys Ala Leu Leu
    195                 200                 205

Cys Asp Val Pro Phe Leu Cys His Phe Arg Arg Ala Val Gln Leu Val
210                 215                 220

Asp Thr His Pro Tyr Val Glu Ile Thr Asn Phe Leu Lys Thr His Arg
225                 230                 235                 240

Asp Lys Glu Glu Ile Val Phe Arg Thr Leu Ser Tyr Phe Asp Gly Val
                245                 250                 255

Asn Phe Ala Ala Arg Ala Lys Val Pro Ala Leu Phe Ser Val Gly Leu
            260                 265                 270

Met Asp Thr Ile Xaa Pro Pro Ser Thr Val Phe Ala Ala Tyr Asn His
        275                 280                 285

Tyr Ala Gly Pro Lys Glu Ile Arg Ile Tyr Pro Tyr Asn Asn His Glu
    290                 295                 300

Gly Gly Gly Ser Phe Gln Ala Ile Glu Gln Val Lys Phe Leu Lys Arg
305                 310                 315                 320

Leu Phe Glu Glu Gly
                325

<210> SEQ ID NO 20
<211> LENGTH: 325
<212> TYPE: PRT
<213> ORGANISM: Thermotoga maritima
<220> FEATURE:
<221> NAME/KEY: MISC_FEATURE
<222> LOCATION: (277)..(277)
<223> OTHER INFORMATION: Xaa is Ala, Val, Ser, or Thr.

<400> SEQUENCE: 20

```
Met Ala Phe Phe Asp Leu Pro Leu Glu Glu Leu Lys Lys Tyr Arg Pro
1               5                   10                  15

Glu Arg Tyr Glu Glu Lys Asp Phe Asp Glu Phe Trp Glu Glu Thr Leu
            20                  25                  30

Ala Glu Ser Glu Lys Phe Pro Leu Asp Pro Val Phe Glu Arg Met Glu
        35                  40                  45

Ser His Leu Lys Thr Val Glu Ala Tyr Asp Val Thr Phe Ser Gly Tyr
    50                  55                  60

Arg Gly Gln Arg Ile Lys Gly Trp Leu Leu Val Pro Lys Leu Glu Glu
65                  70                  75                  80

Glu Lys Leu Pro Cys Val Val Gln Tyr Ile Gly Tyr Asn Gly Gly Arg
                85                  90                  95

Gly Phe Pro His Asp Trp Leu Phe Trp Pro Ser Met Gly Tyr Ile Cys
            100                 105                 110

Phe Val Met Asp Thr Arg Gly Gln Gly Ser Gly Trp Leu Lys Gly Asp
        115                 120                 125

Thr Pro Asp Tyr Pro Glu Gly Pro Val Asp Pro Gln Tyr Pro Gly Phe
    130                 135                 140

Met Thr Arg Gly Ile Leu Asp Pro Arg Thr Tyr Tyr Arg Arg Val
145                 150                 155                 160

Phe Thr Asp Ala Val Arg Ala Val Glu Ala Ala Ser Phe Pro Gln
                165                 170                 175

Val Asp Gln Glu Arg Ile Val Ile Ala Gly Gly Ser Gln Gly Gly Gly
            180                 185                 190

Ile Ala Leu Ala Val Ser Ala Leu Ser Lys Lys Ala Lys Ala Leu Leu
        195                 200                 205

Cys Asp Val Pro Phe Leu Cys His Phe Arg Arg Ala Val Gln Leu Val
    210                 215                 220

Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Phe Asp Gly Val
                245                 250                 255

Asn Phe Ala Ala Arg Ala Lys Ile Pro Ala Leu Phe Ser Val Gly Leu
            260                 265                 270

Met Asp Asn Ile Xaa Pro Pro Ser Thr Val Phe Ala Ala Tyr Asn Tyr
        275                 280                 285

Tyr Ala Gly Pro Lys Glu Ile Arg Ile Tyr Pro Tyr Asn Asn His Glu
    290                 295                 300

Gly Gly Gly Ser Phe Gln Ala Val Glu Gln Val Lys Phe Leu Lys Lys
305                 310                 315                 320

Leu Phe Glu Lys Gly
                325
```

<210> SEQ ID NO 21
<211> LENGTH: 326
<212> TYPE: PRT
<213> ORGANISM: Thermotoga lettingae
<220> FEATURE:
<221> NAME/KEY: MISC_FEATURE
<222> LOCATION: (277)..(277)
<223> OTHER INFORMATION: Xaa is Ala, Val, Ser, or Thr.

<400> SEQUENCE: 21

```
Met Val Tyr Phe Asp Met Pro Leu Glu Asp Leu Arg Lys Tyr Leu Pro
1               5                   10                  15
```

```
Gln Arg Tyr Glu Glu Lys Asp Phe Asp Asp Phe Trp Lys Gln Thr Ile
            20                  25                  30
His Glu Thr Arg Gly Tyr Phe Gln Glu Pro Ile Leu Lys Lys Val Asp
        35                  40                  45
Phe Tyr Leu Gln Asn Val Glu Thr Phe Asp Val Thr Phe Ser Gly Tyr
 50                  55                  60
Arg Gly Gln Lys Ile Lys Gly Trp Leu Ile Leu Pro Lys Phe Arg Asn
 65                  70                  75                  80
Gly Lys Leu Pro Cys Val Val Glu Phe Val Gly Tyr Gly Gly Arg
            85                  90                  95
Gly Phe Pro Tyr Asp Trp Leu Leu Trp Ser Ala Ala Gly Tyr Ala His
            100                 105                 110
Phe Ile Met Asp Thr Arg Gly Gln Gly Ser Asn Trp Met Lys Gly Asp
            115                 120                 125
Thr Pro Asp Tyr Glu Asp Asn Pro Ser Asp Pro Gln Tyr Pro Gly Phe
130                 135                 140
Leu Thr Lys Gly Val Leu Asn Pro Glu Thr Tyr Tyr Arg Arg Val
145                 150                 155                 160
Phe Met Asp Ala Phe Met Ala Val Glu Thr Ile Ser Gln Leu Glu Gln
            165                 170                 175
Ile Asp Ser Gln Thr Ile Ile Leu Ser Gly Ala Ser Gln Gly Gly Gly
            180                 185                 190
Ile Ala Leu Ala Val Ser Ala Leu Ser Ser Lys Val Met Ala Leu Leu
            195                 200                 205
Cys Asp Val Pro Phe Leu Cys His Tyr Lys Arg Ala Val Gln Ile Thr
            210                 215                 220
Asp Ser Met Pro Tyr Ala Glu Ile Thr Arg Tyr Cys Lys Thr His Ile
225                 230                 235                 240
Asp Lys Ile Gln Thr Val Phe Arg Thr Leu Ser Tyr Phe Asp Gly Val
            245                 250                 255
Asn Phe Ala Ala Arg Ala Lys Cys Pro Ala Leu Phe Ser Val Gly Leu
            260                 265                 270
Met Asp Asp Ile Xaa Pro Pro Ser Thr Val Phe Ala Ala Tyr Asn Tyr
            275                 280                 285
Tyr Ala Gly Glu Lys Asp Ile Arg Ile Tyr Pro Tyr Asn Asn His Glu
            290                 295                 300
Gly Gly Gly Ser Phe His Thr Leu Glu Lys Leu Lys Phe Val Lys Lys
305                 310                 315                 320
Thr Ile Ser Met Arg Glu
            325

<210> SEQ ID NO 22
<211> LENGTH: 325
<212> TYPE: PRT
<213> ORGANISM: Thermotoga petrophila
<220> FEATURE:
<221> NAME/KEY: MISC_FEATURE
<222> LOCATION: (277)..(277)
<223> OTHER INFORMATION: Xaa is Ala, Val, Ser, or Thr.

<400> SEQUENCE: 22

Met Ala Phe Phe Asp Leu Pro Leu Glu Glu Leu Lys Lys Tyr Arg Pro
 1                5                  10                  15
Glu Arg Tyr Glu Glu Lys Asp Phe Asp Glu Phe Trp Glu Gly Thr Leu
            20                  25                  30
Ala Glu Asn Glu Lys Phe Pro Leu Asp Pro Val Phe Glu Arg Met Glu
```

```
                35                  40                  45
Ser His Leu Lys Thr Val Glu Ala Tyr Asp Val Thr Phe Ser Gly Tyr
 50                  55                  60

Met Gly Gln Arg Ile Lys Gly Trp Leu Leu Val Pro Lys Leu Glu Glu
 65                  70                  75                  80

Glu Lys Leu Pro Cys Val Val Gln Tyr Ile Gly Tyr Asn Gly Gly Arg
                 85                  90                  95

Gly Phe Pro His Asp Trp Leu Phe Trp Pro Ser Met Gly Tyr Ile Cys
            100                 105                 110

Phe Val Met Asp Thr Arg Gly Gln Gly Ser Gly Trp Met Lys Gly Asp
            115                 120                 125

Thr Pro Asp Tyr Pro Glu Asp Pro Val Asp Pro Gln Tyr Pro Gly Phe
130                 135                 140

Met Thr Arg Gly Ile Leu Asp Pro Arg Thr Tyr Tyr Arg Arg Val
145                 150                 155                 160

Phe Thr Asp Ala Val Arg Ala Val Glu Ala Ala Ser Phe Pro Arg
                165                 170                 175

Val Asp His Glu Arg Ile Val Ile Ala Gly Gly Ser Gln Gly Gly
            180                 185                 190

Ile Ala Leu Ala Val Ser Ala Leu Ser Lys Lys Ala Lys Ala Leu Leu
            195                 200                 205

Cys Asp Val Pro Phe Leu Cys His Phe Arg Arg Ala Val Gln Leu Val
    210                 215                 220

Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Phe Asp Gly Val
                245                 250                 255

Asn Phe Ala Val Arg Ala Lys Ile Pro Ala Leu Phe Ser Val Gly Leu
            260                 265                 270

Met Asp Asn Ile Xaa Pro Pro Ser Thr Val Phe Ala Ala Tyr Asn His
            275                 280                 285

Tyr Ala Gly Pro Lys Glu Ile Arg Ile Tyr Pro Tyr Asn Asn His Glu
290                 295                 300

Gly Gly Gly Ser Phe Gln Ala Ile Glu Gln Val Lys Phe Leu Lys Arg
305                 310                 315                 320

Leu Phe Glu Lys Gly
                325

<210> SEQ ID NO 23
<211> LENGTH: 325
<212> TYPE: PRT
<213> ORGANISM: Thermotoga sp.
<220> FEATURE:
<221> NAME/KEY: MISC_FEATURE
<222> LOCATION: (277)..(277)
<223> OTHER INFORMATION: Xaa is Ala, Val, Ser, or Thr.

<400> SEQUENCE: 23

Met Ala Phe Phe Asp Leu Pro Leu Glu Glu Leu Lys Lys Tyr Arg Pro
 1               5                  10                  15

Glu Arg Tyr Glu Glu Lys Asp Phe Asp Glu Phe Trp Lys Glu Thr Leu
             20                  25                  30

Ala Glu Ser Glu Lys Phe Pro Leu Asp Pro Val Phe Glu Arg Met Glu
            35                  40                  45

Ser His Leu Lys Thr Val Glu Val Tyr Asp Val Thr Phe Ser Gly Tyr
 50                  55                  60
```

```
Arg Gly Gln Arg Ile Lys Gly Trp Leu Leu Val Pro Lys Leu Glu Glu
 65                  70                  75                  80

Glu Lys Leu Pro Cys Val Val Gln Tyr Ile Gly Tyr Asn Gly Gly Arg
                 85                  90                  95

Gly Phe Pro His Asp Trp Leu Phe Trp Pro Ser Met Gly Tyr Ile Cys
            100                 105                 110

Phe Val Met Asp Thr Arg Gly Gln Gly Ser Gly Trp Leu Lys Gly Asp
        115                 120                 125

Thr Pro Asp Tyr Pro Glu Asp Pro Val Asp Pro Gln Tyr Pro Gly Phe
    130                 135                 140

Met Thr Arg Gly Ile Leu Asp Pro Arg Thr Tyr Tyr Tyr Arg Arg Val
145                 150                 155                 160

Phe Thr Asp Ala Val Arg Ala Val Glu Ala Ala Ser Phe Pro Arg
                165                 170                 175

Val Asp His Glu Arg Ile Val Ile Ala Gly Ser Gln Gly Gly Gly
                180                 185                 190

Ile Ala Leu Ala Val Ser Ala Leu Ser Lys Ala Lys Ala Leu Leu
                195                 200                 205

Cys Asp Val Pro Phe Leu Cys His Phe Arg Arg Ala Val Gln Leu Val
210                 215                 220

Asp Thr His Pro Tyr Ala Glu Ile Thr Asn Phe Leu Lys Thr His Arg
225                 230                 235                 240

Asp Lys Glu Glu Ile Val Phe Arg Thr Leu Ser Tyr Phe Asp Gly Val
                245                 250                 255

Asn Phe Ala Val Arg Ala Lys Ile Pro Ala Leu Phe Ser Val Gly Leu
                260                 265                 270

Met Asp Asn Ile Xaa Pro Pro Ser Thr Val Phe Ala Ala Tyr Asn His
                275                 280                 285

Tyr Ala Gly Pro Lys Glu Ile Arg Ile Tyr Pro Tyr Asn Asn His Glu
                290                 295                 300

Gly Gly Gly Ser Phe Gln Ala Ile Glu Gln Val Lys Phe Leu Lys Arg
305                 310                 315                 320

Leu Phe Glu Lys Gly
                325

<210> SEQ ID NO 24
<211> LENGTH: 329
<212> TYPE: PRT
<213> ORGANISM: Thermotoga sp.
<220> FEATURE:
<221> NAME/KEY: MISC_FEATURE
<222> LOCATION: (278)..(278)
<223> OTHER INFORMATION: Xaa is Ala, Val, Ser, or Thr

<400> SEQUENCE: 24

Met Ala Leu Phe Asp Met Pro Leu Glu Lys Leu Arg Ser Tyr Leu Pro
1               5                  10                  15

Asp Arg Tyr Glu Glu Asp Phe Asp Leu Phe Trp Lys Glu Thr Leu
                20                  25                  30

Glu Glu Ser Arg Lys Phe Pro Leu Asp Pro Ile Phe Glu Arg Val Asp
                35                  40                  45

Tyr Leu Leu Glu Asn Val Glu Val Tyr Asp Val Thr Phe Ser Gly Tyr
    50                  55                  60

Arg Gly Gln Arg Ile Lys Ala Trp Leu Ile Leu Pro Val Val Lys Lys
65                  70                  75                  80

Glu Glu Arg Leu Pro Cys Ile Val Glu Phe Ile Gly Tyr Arg Gly Gly
                85                  90                  95
```

-continued

```
Arg Gly Phe Pro Phe Asp Trp Leu Phe Trp Ser Ser Ala Gly Tyr Ala
            100                 105                 110

His Phe Val Met Asp Thr Arg Gly Gln Gly Thr Ser Arg Val Lys Gly
        115                 120                 125

Asp Thr Pro Asp Tyr Cys Asp Glu Pro Ile Asn Pro Gln Phe Pro Gly
    130                 135                 140

Phe Met Thr Arg Gly Ile Leu Asp Pro Arg Thr Tyr Tyr Arg Arg
145                 150                 155                 160

Val Phe Thr Asp Ala Val Arg Ala Val Glu Thr Ala Ser Ser Phe Pro
                165                 170                 175

Gly Ile Asp Pro Glu Arg Ile Ala Val Val Gly Thr Ser Gln Gly Gly
            180                 185                 190

Gly Ile Ala Leu Ala Val Ala Ala Leu Ser Glu Ile Pro Lys Ala Leu
        195                 200                 205

Val Ser Asn Val Pro Phe Leu Cys His Phe Arg Arg Ala Val Gln Ile
    210                 215                 220

Thr Asp Asn Ala Pro Tyr Ser Glu Ile Val Asn Tyr Leu Lys Val His
225                 230                 235                 240

Arg Asp Lys Glu Glu Ile Val Phe Arg Thr Leu Ser Tyr Phe Asp Gly
                245                 250                 255

Val Asn Phe Ala Ala Arg Ala Lys Ile Pro Ala Leu Phe Ser Val Ala
            260                 265                 270

Leu Met Asp Lys Thr Xaa Pro Pro Ser Thr Val Phe Ala Ala Tyr Asn
        275                 280                 285

His Tyr Ala Gly Pro Lys Glu Ile Lys Val Tyr Pro Phe Asn Glu His
    290                 295                 300

Glu Gly Gly Glu Ser Phe Gln Arg Met Glu Glu Leu Arg Phe Met Lys
305                 310                 315                 320

Arg Ile Leu Lys Gly Glu Phe Lys Ala
                325

<210> SEQ ID NO 25
<211> LENGTH: 320
<212> TYPE: PRT
<213> ORGANISM: Thermoanaerobacter sp.
<220> FEATURE:
<221> NAME/KEY: MISC_FEATURE
<222> LOCATION: (275)..(275)
<223> OTHER INFORMATION: Xaa is Ala, Val, Ser, or Thr.

<400> SEQUENCE: 25

Met Gly Leu Phe Asp Met Pro Leu Gln Lys Leu Arg Glu Tyr Thr Gly
1               5                   10                  15

Thr Asn Pro Cys Pro Glu Asp Phe Asp Glu Tyr Trp Asn Arg Ala Leu
            20                  25                  30

Asp Glu Met Arg Ser Val Asp Pro Lys Ile Glu Leu Lys Glu Ser Ser
        35                  40                  45

Phe Gln Val Ser Phe Ala Glu Cys Tyr Asp Leu Tyr Phe Thr Gly Val
    50                  55                  60

Arg Gly Ala Arg Ile His Ala Lys Tyr Ile Lys Pro Lys Thr Glu Gly
65                  70                  75                  80

Lys His Pro Ala Leu Ile Arg Phe His Gly Tyr Ser Ser Asn Ser Gly
                85                  90                  95

Asp Trp Asn Asp Lys Leu Asn Tyr Val Ala Ala Gly Phe Thr Val Val
            100                 105                 110

Ala Met Asp Val Arg Gly Gln Gly Gly Gln Ser Gln Asp Val Gly Gly
```

```
                115                 120                 125
Val Thr Gly Asn Thr Leu Asn Gly His Ile Ile Arg Gly Leu Asp Asp
130                 135                 140

Asp Ala Asp Asn Met Leu Phe Arg His Ile Phe Leu Asp Thr Ala Gln
145                 150                 155                 160

Leu Ala Gly Ile Val Met Asn Met Pro Glu Val Asp Glu Asp Arg Val
                165                 170                 175

Gly Val Met Gly Pro Ser Gln Gly Gly Leu Ser Leu Ala Cys Ala
                180                 185                 190

Ala Leu Glu Pro Arg Val Arg Lys Val Val Ser Glu Tyr Pro Phe Leu
                195                 200                 205

Ser Asp Tyr Lys Arg Val Trp Asp Leu Asp Leu Ala Lys Asn Ala Tyr
210                 215                 220

Gln Glu Ile Thr Asp Tyr Phe Arg Leu Phe Asp Pro Arg His Glu Arg
225                 230                 235                 240

Glu Asn Glu Val Phe Thr Lys Leu Gly Tyr Ile Asp Val Lys Asn Leu
                245                 250                 255

Ala Lys Arg Ile Lys Gly Asp Val Leu Met Cys Val Gly Leu Met Asp
                260                 265                 270

Gln Val Xaa Pro Pro Ser Thr Val Phe Ala Ala Tyr Asn Asn Ile Gln
                275                 280                 285

Ser Lys Lys Asp Ile Lys Val Tyr Pro Asp Tyr Gly His Glu Pro Met
290                 295                 300

Arg Gly Phe Gly Asp Leu Ala Met Gln Phe Met Leu Glu Leu Tyr Ser
305                 310                 315                 320

<210> SEQ ID NO 26
<211> LENGTH: 795
<212> TYPE: DNA
<213> ORGANISM: Streptomyces kanamyceticus

<400> SEQUENCE: 26
atgattgaac aagatggatt gcacgcaggt tctccggccg cttgggtgga gaggctattc      60
ggctatgact gggcacaaca gacaatcggc tgctctgatg ccgccgtgtt ccggctgtca     120
gcgcaggggc gcccggttct ttttgtcaag accgacctgt ccggtgccct gaatgaactg     180
caggacgagg cagcgcggct atcgtggctg gccacgacgg gcgttccttg cgcagctgtg     240
ctcgacgttg tcactgaagc gggaagggac tggctgctat tgggcgaagt gccggggcag     300
gatctcctgt catctcacct tgctcctgcc gagaaagtat ccatcatggc tgatgcaatg     360
cggcggctgc atacgcttga tccggctacc tgcccattcg accaccaagc gaaacatcgc     420
atcgagcgag cacgtactcg gatggaagcc ggtcttgtcg atcaggatga tctggacgaa     480
gagcatcagg ggctcgcgcc agccgaactg ttcgccaggc tcaaggcgcg catgcccgac     540
ggcgaggatc tcgtcgtgac ccatggcgat gcctgcttgc cgaatatcat ggtgaaaat     600 ggccgctttt ctggattcat cgactgtggc cggctgggtg tggcggaccg ctatcaggac     660
atagcgttgg ctacccgtga tattgctgaa gagcttggcg gcgaatgggc tgaccgcttc     720
ctcgtgcttt acggtatcgc cgctcccgat tcgcagcgca tcgccttcta tcgccttctt     780
gacgagttct tctaa                                                      795

<210> SEQ ID NO 27
<211> LENGTH: 3434
<212> TYPE: DNA
<213> ORGANISM: Artificial sequence
<220> FEATURE:
```

<223> OTHER INFORMATION: Plasmid pKD13

<400> SEQUENCE: 27

```
agattgcagc attacacgtc ttgagcgatt gtgtaggctg gagctgcttc gaagttccta      60
tactttctag agaataggaa cttcggaata ggaacttcaa gatcccctta ttagaagaac     120
tcgtcaagaa ggcgatagaa ggcgatgcgc tgcgaatcgg gagcggcgat accgtaaagc     180
acgaggaagc ggtcagccca ttcgccgcca agctcttcag caatatcacg ggtagccaac     240
gctatgtcct gatagcggtc cgccacaccc agccggccac agtcgatgaa tccagaaaag     300
cggccatttt ccaccatgat attcggcaag caggcatcgc catgggtcac gacgagatcc     360
tcgccgtcgg gcatgcgcgc cttgagcctg gcgaacagtt cggctggcgc gagcccctga     420
tgctcttcgt ccagatcatc ctgatcgaca gaccggcttc catccgagt acgtgctcgc      480
tcgatgcgat gtttcgcttg gtggtcgaat gggcaggtag ccggatcaag cgtatgcagc     540
cgccgcattg catcagccat gatggatact ttctcggcag gagcaaggtg agatgacagg     600
agatcctgcc ccggcacttc gcccaatagc agccagtccc ttcccgcttc agtgacaacg     660
tcgagcacag ctgcgcaagg aacgcccgtc gtggccagcc acgatagccg cgctgcctcg     720
tcctgcagtt cattcagggc accggacagg tcggtcttga caaaaagaac cgggcgcccc     780
tgcgctgaca gccggaacac ggcggcatca gagcagccga ttgtctgttg tgcccagtca     840
tagccgaata gcctctccac ccaagcggcc ggagaacctg cgtgcaatcc atcttgttca     900
atcatgcgaa acgatcctca tcctgtctct tgatcagatc ttgatcccct gcgccatcag     960
atccttggcg gcaagaaagc catccagttt actttgcagg gcttcccaac cttaccagag    1020
ggcgccccag ctggcaattc cggttcgctt gctgtccata aaaccgccca gtctagctat    1080
cgccatgtaa gcccactgca agctacctgc tttctctttg cgcttgcgtt ttcccttgtc    1140
cagatagccc agtagctgac attcatccgg ggtcagcacc gtttctgcgg actggctttc    1200
tacgtgttcc gcttccttta gcagcccttg cgccctgagt gcttgcggca gcgtgagctt    1260
caaaagcgct ctgaagttcc tatactttct agagaatagg aacttcgaac tgcaggtcga    1320
cggatccccg gaattaattc tcatgtttga cagcttatca ctgatcagtg aattaatggc    1380
gatgacgcat cctcacgata atatccgggt aggcgcaatc actttcgtct ctactccgtt    1440
acaaagcgag gctgggtatt tcccggcctt tctgttatcc gaaatccact gaaagcacag    1500
cggctggctg aggagataaa taataaacga ggggctgtat gcacaaagca tcttctgttg    1560
agttaagaac gagtatcgag atggcacata gccttgctca aattggaatc aggtttgtgc    1620
caataccagt agaaacagac gaagaagcta gctttgcact ggattgcgag gctttgccat    1680
ggctaattcc catgtcagcc gttaagtgtt cctgtgtcac tgaaaattgc tttgagaggc    1740
tctaagggct tctcagtgcg ttacatccct ggcttgttgt ccacaaccgt aaaccttaa     1800
aagctttaaa agccttatat attcttttt ttcttataaa acttaaaacc ttagaggcta     1860
tttaagttgc tgatttatat taattttatt gttcaaacat gagagcttag tacgtgaaac    1920
atgagagctt agtacgttag ccatgagagc ttagtacgtt agccatgagg tttagttcg     1980
ttaaacatga gagcttagta cgttaaacat gagagcttag tacgtgaaac atgagagctt    2040
agtacgtact atcaacaggt tgaactgcgg atcttgcggc cgcaaaaatt aaaaatgaag    2100
ttttaaatca atctaaagta tatatgagta aacttggtct gacagttacc aatgcttaat    2160
cagtgaggca cctatctcag cgatctgtct atttcgttca tccatagttg cctgactccc    2220
cgtcgtgtag ataactacga tacgggaggg cttaccatct ggccccagtg ctgcaatgat    2280
```

```
accgcgagac ccacgctcac cggctccaga tttatcagca ataaaccagc cagccggaag    2340
ggccgagcgc agaagtggtc ctgcaacttt atccgcctcc atccagtcta ttaattgttg    2400
ccgggaagct agagtaagta gttcgccagt taatagtttg cgcaacgttg ttgccattgc    2460
tacaggcatc gtggtgtcac gctcgtcgtt tggtatggct tcattcagct ccggttccca    2520
acgatcaagg cgagttacat gatcccccat gttgtgcaaa aaagcggtta gctccttcgg    2580
tcctccgatc gttgtcagaa gtaagttggc cgcagtgtta tcactcatgg ttatggcagc    2640
actgcataat tctcttactg tcatgccatc cgtaagatgc ttttctgtga ctggtgagta    2700
ctcaaccaag tcattctgag aatagtgtat gcggcgaccg agttgctctt gcccggcgtc    2760
aatacgggat aataccgcgc cacatagcag aactttaaaa gtgctcatca ttggaaaacg    2820
ttcttcgggg cgaaaactct caaggatctt accgctgttg agatccagtt cgatgtaacc    2880
cactcgtgca cccaactgat cttcagcatc ttttactttc accagcgttt ctgggtgagc    2940
aaaaacagga aggcaaaatg ccgcaaaaaa gggaataagg gcgacacgga aatgttgaat    3000
actcatactc ttcctttttc aatattattg aagcatttat cagggttatt gtctcatgag    3060
cggatacata tttgaatgta tttagaaaaa taaacaaata ggggttccgc gcacatttcc    3120
ccgaaaagtg ccacctgcat cgatggcccc ccgatggtag tgtggggtct ccccatgcga    3180
gagtagggaa ctgccaggca tcaaataaaa cgaaaggctc agtcgaaaga ctgggccttt    3240
cgttttatct gttgtttgtc ggtgaacgct ctcctgagta ggacaaatcc gccggagcg    3300 gatttgaacg ttgcgaagca acggcccgga gggtggcggg caggacgccc gccataaact    3360
gccaggcatc aaattaagca gaaggccatc ctgacggatg ccttttttgc gtggccagtg    3420
ccaagcttgc atgc                                                     3434

<210> SEQ ID NO 28
<211> LENGTH: 80
<212> TYPE: DNA
<213> ORGANISM: Artificial sequence
<220> FEATURE:
<223> OTHER INFORMATION: Primer

<400> SEQUENCE: 28
atgagcacgt cagacgatat ccataacacc acagccactg gcaaatgccc gttccatcag    60
gtgtaggctg gagctgcttc                                                80

<210> SEQ ID NO 29
<211> LENGTH: 82
<212> TYPE: DNA
<213> ORGANISM: Artificial sequence
<220> FEATURE:
<223> OTHER INFORMATION: Primer

<400> SEQUENCE: 29
taacagcagg tcgaaacggt cgaggttcat cactttcacc catgccgcca cgaagtcttt    60
attccgggga tccgtcgacc tg                                              82

<210> SEQ ID NO 30
<211> LENGTH: 1424
<212> TYPE: DNA
<213> ORGANISM: Artificial sequence
<220> FEATURE:
<223> OTHER INFORMATION: Synthetic construct

<400> SEQUENCE: 30
taacagcagg tcgaaacggt cgaggttcat cactttcacc catgccgcca cgaagtcttt    60
```

-continued

| | |
|---|---|
| attccgggga tccgtcgacc tgcagttcga agttcctatt ctctagaaag tataggaact | 120 |
| tcagagcgct tttgaagctc acgctgccgc aagcactcag ggcgcaaggg ctgctaaagg | 180 |
| aagcggaaca cgtagaaagc cagtccgcag aaacggtgct gaccccggat gaatgtcagc | 240 |
| tactgggcta tctggacaag ggaaaacgca agcgcaaaga gaaagcaggt agcttgcagt | 300 |
| gggcttacat ggcgatagct agactgggcg gttttatgga cagcaagcga accggaattg | 360 |
| ccagctgggg cgccctctgg taaggttggg aagccctgca agtaaactg gatggctttc | 420 |
| ttgccgccaa ggatctgatg gcgcagggga tcaagatctg atcaagagac aggatgagga | 480 |
| tcgtttcgca tgattgaaca agatggattg cacgcaggtt ctccggccgc ttgggtggag | 540 |
| aggctattcg gctatgactg ggcacaacag acaatcggct gctctgatgc cgccgtgttc | 600 |
| cggctgtcag cgcaggggcg cccgttcttt tttgtcaaga ccgacctgtc cggtgccctg | 660 |
| aatgaactgc aggacgaggc agcgcggcta tcgtggctgg ccacgacggg cgttccttgc | 720 |
| gcagctgtgc tcgacgttgt cactgaagcg ggaagggact ggctgctatt gggcgaagtg | 780 |
| ccggggcagg atctcctgtc atctcacctt gctcctgccg agaaagtatc catcatggct | 840 |
| gatgcaatgc ggcggctgca tacgcttgat ccggctacct gcccattcga ccaccaagcg | 900 |
| aaacatcgca tcgagcgagc acgtactcgg atggaagccg gtcttgtcga tcaggatgat | 960 |
| ctggacgaag agcatcaggg gctcgcgcca gccgaactgt tcgccaggct caaggcgcgc | 1020 |
| atgcccgacg gcgaggatct cgtcgtgacc catggcgatg cctgcttgcc gaatatcatg | 1080 |
| gtggaaaatg gccgcttttc tggattcatc gactgtggcc ggctgggtgt ggcggaccgc | 1140 |
| tatcaggaca tagcgttggc tacccgtgat attgctgaag agcttggcgg cgaatgggct | 1200 |
| gaccgcttcc tcgtgcttta cggtatcgcc gctcccgatt cgcagcgcat cgccttctat | 1260 |
| cgccttcttg acgagttctt ctaataaggg gatcttgaag ttcctattcc gaagttccta | 1320 |
| ttctctagaa agtataggaa cttcgaagca gctccagcct acacctgatg gaacgggcat | 1380 |
| ttgccagtgg ctgtggtgtt atggatatcg tctgacgtgc tcat | 1424 |

<210> SEQ ID NO 31
<211> LENGTH: 2181
<212> TYPE: DNA
<213> ORGANISM: Escherichia coli

<400> SEQUENCE: 31

| | |
|---|---|
| atgagcacgt cagacgatat ccataacacc acagccactg gcaaatgccc gttccatcag | 60 |
| ggcggtcacg accagagtgc gggggcgggc acaaccactc gcgactggtg gccaaatcaa | 120 |
| cttcgtgttg acctgttaaa ccaacattct aatcgttcta acccactggg tgaggacttt | 180 |
| gactaccgca agaattcag caaattagat tactacggcc tgaaaaaaga tctgaaagcc | 240 |
| ctgttgacag aatctcaacc gtggtggcca gccgactggg gcagttacgc cggtctgttt | 300 |
| attcgtatgg cctggcacgg cgcggggact taccgttcaa tcgatggacg cggtggcgcg | 360 |
| ggtcgtggtc agcaacgttt tgcaccgctg aactcctggc cggataacgt aagcctcgat | 420 |
| aaagcgcgtc gcctgttgtg gccaatcaaa cagaaatatg gtcagaaaat ctcctgggcc | 480 |
| gacctgttta tcctcgcggg taacgtggcg ctagaaaact ccggcttccg taccttcggt | 540 |
| tttggtgccg tcgtgaaga cgtctgggaa ccggatctgg atgttaactg gggtgatgaa | 600 |
| aaagcctggc tgactcaccg tcatccggaa gcgctggcga agcaccgct gggtgcaacc | 660 |
| gagatgggtc tgatttacgt taacccggaa ggcccggatc acagcggcga accgctttct | 720 |
| gcggcagcag ctatccgcgc gaccttcggc aacatgggca tgaacgacga agaaaccgtg | 780 |

```
gcgctgattg cgggtggtca tacgctgggt aaaacccacg gtgccggtcc gacatcaaat      840
gtaggtcctg atccagaagc tgcaccgatt gaagaacaag gtttaggttg ggcgagcact      900
tacggcagcg gcgttggcgc agatgccatt acctctggtc tggaagtagt ctggacccag      960
acgccgaccc agtggagcaa ctatttcttc gagaacctgt tcaagtatga gtgggtacag     1020
acccgcagcc cggctggcgc aatccagttc gaagcggtag acgcaccgga aattatcccg     1080
gatccgtttg atccgtcgaa gaaacgtaaa ccgacaatgc tggtgaccga cctgacgctg     1140
cgttttgatc ctgagttcga gaagatctct cgtcgtttcc tcaacgatcc gcaggcgttc     1200
aacgaagcct ttgcccgtgc ctggttcaaa ctgacgcaca gggatatggg gccgaaatct     1260
cgctacatcg ggccggaagt gccgaaagaa gatctgatct ggcaagatcc gctgccgcag     1320
ccgatctaca cccgaccgga gcaggacatt atcgatctga aattcgcgat tgcggattct     1380
ggtctgtctg ttagtgagct ggtatcggtg gcctgggcat ctgcttctac cttccgtggt     1440
ggcgacaaac gcggtggtgc caacggtgcg cgtctggcat taatgccgca gcgcgactgg     1500
gatgtgaacg ccgcagccgt tcgtgctctg cctgttctgg agaaaatcca gaaagagtct     1560
ggtaaagcct cgctggcgga tatcatagtg ctggctggtg tggttggtgt tgagaaagcc     1620
gcaagcgccg caggtttgag cattcatgta ccgtttgcgc cgggtcgcgt tgatgcgcgt     1680
caggatcaga ctgacattga gatgtttgag ctgctggagc caattgctga cggtttccgt     1740
aactatcgcg ctcgtctgga cgtttccacc accgagtcac tgctgatcga caaagcacag     1800
caactgacgc tgaccgcgcc ggaaatgact gcgctggtgg gcggcatgcg tgtactgggt     1860
gccaacttcg atggcagcaa aaacggcgtc ttcactgacc gcgttggcgt attgagcaat     1920
gacttcttcg tgaacttgct ggatatgcgt tacgagtgga agcgaccga cgaatcgaaa     1980 gagctgttcg aaggccgtga ccgtgaaacc ggcgaagtga aatttacggc cagccgtgcg     2040
gatctggtgt ttggttctaa ctccgtcctg cgtgcggtgg cggaagttta cgccagtagc     2100
gatgcccacg agaagtttgt taaagacttc gtggcggcat gggtgaaagt gatgaacctc     2160
gaccgtttcg acctgctgta a                                               2181
```

<210> SEQ ID NO 32
<211> LENGTH: 726
<212> TYPE: PRT
<213> ORGANISM: Escherichia coli

<400> SEQUENCE: 32

Met Ser Thr Ser Asp Asp Ile His Asn Thr Thr Ala Thr Gly Lys Cys
1               5                   10                  15

Pro Phe His Gln Gly Gly His Asp Gln Ser Ala Gly Ala Gly Thr Thr
            20                  25                  30

Thr Arg Asp Trp Trp Pro Asn Gln Leu Arg Val Asp Leu Leu Asn Gln
        35                  40                  45

His Ser Asn Arg Ser Asn Pro Leu Gly Glu Asp Phe Asp Tyr Arg Lys
    50                  55                  60

Glu Phe Ser Lys Leu Asp Tyr Tyr Gly Leu Lys Lys Asp Leu Lys Ala
65                  70                  75                  80

Leu Leu Thr Glu Ser Gln Pro Trp Trp Pro Ala Asp Trp Gly Ser Tyr
                85                  90                  95

Ala Gly Leu Phe Ile Arg Met Ala Trp His Gly Ala Gly Thr Tyr Arg
            100                 105                 110

Ser Ile Asp Gly Arg Gly Gly Ala Gly Arg Gly Gln Gln Arg Phe Ala
        115                 120                 125

-continued

```
Pro Leu Asn Ser Trp Pro Asp Asn Val Ser Leu Asp Lys Ala Arg Arg
    130                 135                 140

Leu Leu Trp Pro Ile Lys Gln Lys Tyr Gly Gln Lys Ile Ser Trp Ala
145                 150                 155                 160

Asp Leu Phe Ile Leu Ala Gly Asn Val Ala Leu Glu Asn Ser Gly Phe
                165                 170                 175

Arg Thr Phe Gly Phe Gly Ala Gly Arg Glu Asp Val Trp Glu Pro Asp
            180                 185                 190

Leu Asp Val Asn Trp Gly Asp Glu Lys Ala Trp Leu Thr His Arg His
        195                 200                 205

Pro Glu Ala Leu Ala Lys Ala Pro Leu Gly Ala Thr Glu Met Gly Leu
    210                 215                 220

Ile Tyr Val Asn Pro Glu Gly Pro Asp His Ser Gly Glu Pro Leu Ser
225                 230                 235                 240

Ala Ala Ala Ala Ile Arg Ala Thr Phe Gly Asn Met Gly Met Asn Asp
                245                 250                 255

Glu Glu Thr Val Ala Leu Ile Ala Gly His Thr Leu Gly Lys Thr
            260                 265                 270

His Gly Ala Gly Pro Thr Ser Asn Val Gly Pro Asp Pro Glu Ala Ala
        275                 280                 285

Pro Ile Glu Glu Gln Gly Leu Gly Trp Ala Ser Thr Tyr Gly Ser Gly
    290                 295                 300

Val Gly Ala Asp Ala Ile Thr Ser Gly Leu Glu Val Val Trp Thr Gln
305                 310                 315                 320

Thr Pro Thr Gln Trp Ser Asn Tyr Phe Phe Glu Asn Leu Phe Lys Tyr
                325                 330                 335

Glu Trp Val Gln Thr Arg Ser Pro Ala Gly Ala Ile Gln Phe Glu Ala
            340                 345                 350

Val Asp Ala Pro Glu Ile Ile Pro Asp Pro Phe Asp Pro Ser Lys Lys
        355                 360                 365

Arg Lys Pro Thr Met Leu Val Thr Asp Leu Thr Leu Arg Phe Asp Pro
    370                 375                 380

Glu Phe Glu Lys Ile Ser Arg Arg Phe Leu Asn Asp Pro Gln Ala Phe
385                 390                 395                 400

Asn Glu Ala Phe Ala Arg Ala Trp Phe Lys Leu Thr His Arg Asp Met
                405                 410                 415

Gly Pro Lys Ser Arg Tyr Ile Gly Pro Glu Val Pro Lys Glu Asp Leu
            420                 425                 430

Ile Trp Gln Asp Pro Leu Pro Gln Pro Ile Tyr Asn Pro Thr Glu Gln
        435                 440                 445

Asp Ile Ile Asp Leu Lys Phe Ala Ile Ala Asp Ser Gly Leu Ser Val
    450                 455                 460

Ser Glu Leu Val Ser Val Ala Trp Ala Ser Ala Ser Thr Phe Arg Gly
465                 470                 475                 480

Gly Asp Lys Arg Gly Gly Ala Asn Gly Ala Arg Leu Ala Leu Met Pro
                485                 490                 495

Gln Arg Asp Trp Asp Val Asn Ala Ala Ala Val Arg Ala Leu Pro Val
            500                 505                 510

Leu Glu Lys Ile Gln Lys Glu Ser Gly Lys Ala Ser Leu Ala Asp Ile
        515                 520                 525

Ile Val Leu Ala Gly Val Val Gly Val Glu Lys Ala Ala Ser Ala Ala
    530                 535                 540

Gly Leu Ser Ile His Val Pro Phe Ala Pro Gly Arg Val Asp Ala Arg
545                 550                 555                 560
```

Gln Asp Gln Thr Asp Ile Glu Met Phe Glu Leu Leu Glu Pro Ile Ala
            565                 570                 575

Asp Gly Phe Arg Asn Tyr Arg Ala Arg Leu Asp Val Ser Thr Thr Glu
        580                 585                 590

Ser Leu Leu Ile Asp Lys Ala Gln Gln Leu Thr Leu Thr Ala Pro Glu
            595                 600                 605

Met Thr Ala Leu Val Gly Gly Met Arg Val Leu Gly Ala Asn Phe Asp
        610                 615                 620

Gly Ser Lys Asn Gly Val Phe Thr Asp Arg Val Gly Val Leu Ser Asn
625                 630                 635                 640

Asp Phe Phe Val Asn Leu Leu Asp Met Arg Tyr Glu Trp Lys Ala Thr
                645                 650                 655

Asp Glu Ser Lys Glu Leu Phe Glu Gly Arg Asp Arg Glu Thr Gly Glu
            660                 665                 670

Val Lys Phe Thr Ala Ser Arg Ala Asp Leu Val Phe Gly Ser Asn Ser
        675                 680                 685

Val Leu Arg Ala Val Ala Glu Val Tyr Ala Ser Ser Asp Ala His Glu
690                 695                 700

Lys Phe Val Lys Asp Phe Val Ala Ala Trp Val Lys Val Met Asn Leu
705                 710                 715                 720

Asp Arg Phe Asp Leu Leu
            725

<210> SEQ ID NO 33
<211> LENGTH: 6329
<212> TYPE: DNA
<213> ORGANISM: Artificial sequence
<220> FEATURE:
<223> OTHER INFORMATION: Plasmid pKD46

<400> SEQUENCE: 33

```
catcgattta ttatgacaac ttgacggcta catcattcac ttttcttca caaccggcac      60
ggaactcgct cgggctggcc ccggtgcatt ttttaaatac ccgcgagaaa tagagttgat    120
cgtcaaaacc aacattgcga ccgacggtgg cgataggcat ccgggtggtg ctcaaaagca    180
gcttcgcctg gctgatacgt tggtcctcgc gccagcttaa gacgctaatc cctaactgct    240
ggcggaaaag atgtgacaga cgcgacggcg acaagcaaac atgctgtgcg acgctggcga    300
tatcaaaatt gctgtctgcc aggtgatcgc tgatgtactg acaagcctcg cgtacccgat    360
tatccatcgg tggatggagc gactcgttaa tcgcttccat cgccgcagt aacaattgct    420
caagcagatt tatcgccagc agctccgaat agcgcccttc ccttgcccg gcgttaatga    480
tttgcccaaa caggtcgctg aaatgcggct ggtgcgcttc atccgggcga agaaccccg    540
tattggcaaa tattgacggc cagttaagcc attcatgcca gtaggcgcgc ggacgaaagt    600
aaacccactg gtgataccat tcgcgagcct ccggatgacg accgtagtga tgaatctctc    660
ctggcgggaa cagcaaaata tcacccggtc ggcaaacaaa ttctcgtccc tgatttttca    720
ccacccctg accgcgaatg gtgagattga gaatataacc tttcattccc agcggtcggt    780
cgataaaaaa atcgagataa ccgttggcct caatcggcgt taaacccgcc accagatggg    840
cattaaacga gtatcccggc agcaggggat cattttgcgc ttcagccata cttttcatac    900
tcccgccatt cagagaagaa accaattgtc atattgcat cagacattgc cgtcactgcg    960
tcttttactg gctcttctcg ctaaccaaac cggtaacccc gcttattaaa agcattctgt   1020
aacaaagcgg gaccaaagcc atgacaaaaa cgcgtaacaa aagtgtctat aatcacggca   1080
```

```
gaaaagtcca cattgattat ttgcacggcg tcacactttg ctatgccata gcatttttat    1140
ccataagatt agcggatcct acctgacgct ttttatcgca actctctact gtttctccat    1200
acccgttttt ttgggaattc gagctctaag gaggttataa aaatggata ttaatactga     1260 aactgagatc aagcaaaagc attcactaac ccccttttcct gttttcctaa tcagcccggc   1320
atttcgcggg cgatattttc acagctattt caggagttca gccatgaacg cttattacat   1380
tcaggatcgt cttgaggctc agagctgggc gcgtcactac cagcagctcg cccgtgaaga   1440
gaaagaggca gaactggcag acgacatgga aaaaggcctg ccccagcacc tgtttgaatc   1500
gctatgcatc gatcatttgc aacgccacgg ggccagcaaa aaatccatta cccgtgcgtt   1560
tgatgacgat gttgagtttc aggagcgcat ggcagaacac atccggtaca tggttgaaac   1620
cattgctcac caccaggttg atattgattc agaggtataa aacgaatgag tactgcactc   1680
gcaacgctgg ctgggaagct ggctgaacgt gtcggcatgg attctgtcga cccacaggaa   1740
ctgatcacca ctcttcgcca gacgcatttt aaaggtgatg ccagcgatgc gcagttcatc   1800
gcattactga tcgttgccaa ccagtacggc cttaatccgt ggacgaaaga aatttacgcc   1860
tttcctgata agcagaatgg catcgttccg gtggtgggcg ttgatggctg gtcccgcatc   1920
atcaatgaaa accagcagtt tgatggcatg gactttgagc aggacaatga atcctgtaca   1980
tgccggattt accgcaagga ccgtaatcat ccgatctgcg ttaccgaatg gatggatgaa   2040
tgccgccgcg aaccattcaa aactcgcgaa ggcagagaaa tcacggggcc gtggcagtcg   2100
catcccaaac ggatgttacg tcataaagcc atgattcagt gtgcccgtct ggccttcgga   2160
tttgctggta tctatgacaa ggatgaagcc gagcgcattg tcgaaaatac tgcatacact   2220
gcagaacgtc agccggaacg cgacatcact ccggttaacg atgaaaccat gcaggagatt   2280
aacactctgc tgatcgccct ggataaaaca tgggatgacg acttattgcc gctctgttcc   2340
cagatatttc gccgcgacat tcgtgcatcg tcagaactga cacaggccga agcagtaaaa   2400
gctcttggat tcctgaaaca gaaagccgca gagcagaagg tggcagcatg acaccggaca   2460
ttatcctgca gcgtaccggg atcgatgtga gagctgtcga acaggggggat gatgcgtggc   2520 acaaattacg gctcggcgtc atcaccgctt cagaagttca caacgtgata gcaaaacccc   2580
gctccggaaa gaagtggcct gacatgaaaa tgtcctactt ccacaccctg cttgctgagg   2640
tttgcaccgg tgtggctccg gaagttaacg ctaaagcact ggcctgggga aaacagtacg   2700
agaacgacgc cagaaccctg tttgaattca cttccggcgt gaatgttact gaatccccga   2760
tcatctatcg cgacgaaagt atgcgtaccg cctgctctcc cgatggttta tgcagtgacg   2820
gcaacggcct tgaactgaaa tgcccgtttta cctcccggga tttcatgaag ttccggctcg   2880
gtggtttcga ggccataaag tcagcttaca tggcccaggt gcagtacagc atgtgggtga   2940
cgcgaaaaaa tgcctggtac tttgccaact atgacccgcg tatgaagcgt gaaggcctgc   3000
attatgtcgt gattgagcgg gatgaaaagt acatggcgag ttttgacgag atcgtgccgg   3060
agttcatcga aaaaatggac gaggcactgg ctgaaattgg ttttgtattt ggggagcaat   3120
ggcgatgacg catcctcacg ataatatccg ggtaggcgca atcactttcg tctactccgt   3180
tacaaagcga ggctgggtat ttcccggcct ttctgttatc cgaaatccac tgaaagcaca   3240
gcggctggct gaggagataa ataataaacg aggggctgta tgcacaaagc atcttctgtt   3300
gagttaagaa cgagtatcga gatggcacat agccttgctc aaattggaat caggtttgtg   3360
ccaataccag tagaaacaga cgaagaatcc atgggtatgg acagttttcc ctttgatatg   3420
taacggtgaa cagttgttct actttgtgtt gttagtcttg atgcttcact gatagataca   3480
```

```
agagccataa gaacctcaga tccttccgta tttagccagt atgttctcta gtgtggttcg    3540 ttgttttttgc gtgagccatg agaacgaacc attgagatca tacttacttt gcatgtcact    3600
caaaaatttt gcctcaaaac tggtgagctg aattttttgca gttaaagcat cgtgtagtgt    3660
ttttcttagt ccgttacgta ggtaggaatc tgatgtaatg gttgttggta ttttgtcacc    3720
attcattttt atctggttgt tctcaagttc ggttacgaga tccatttgtc tatctagttc    3780
aacttggaaa atcaacgtat cagtcgggcg gcctcgctta tcaaccacca atttcatatt    3840
gctgtaagtg tttaaatctt tacttattgg tttcaaaacc cattggttaa gccttttaaa    3900
ctcatggtag ttattttcaa gcattaacat gaacttaaat tcatcaaggc taatctctat    3960
atttgccttg tgagttttct tttgtgttag ttcttttaat aaccactcat aaatcctcat    4020
agagtatttg ttttcaaaag acttaacatg ttccagatta tattttatga atttttttaa    4080
ctggaaaaga taaggcaata tctcttcact aaaaactaat tctaattttt cgcttgagaa    4140
cttggcatag tttgtccact ggaaaatctc aaagccttta accaaggat tcctgatttc    4200 cacagttctc gtcatcagct ctctggttgc tttagctaat acaccataag cattttccct    4260
actgatgttc atcatctgag cgtattggtt ataagtgaac gataccgtcc gttcttttcct    4320 tgtagggttt tcaatcgtgg ggttgagtag tgccacacag cataaaatta gcttggtttc    4380
atgctccgtt aagtcatagc gactaatcgc tagttcattt gctttgaaaa caactaattc    4440
agacatacat ctcaattggt ctaggtgatt ttaatcacta taccaattga gatgggctag    4500
tcaatgataa ttactagtcc ttttcctttg agttgtgggt atctgtaaat tctgctagac    4560
ctttgctgga aaacttgtaa attctgctag accctctgta aattccgcta gacctttgtg    4620 tgttttttt gttatattc aagtggttat aatttataga ataaagaaag aataaaaaaa    4680
gataaaaaga atagatccca gccctgtgta taactcacta ctttagtcag ttccgcagta    4740
ttacaaaagg atgtcgcaaa cgctgtttgc tcctctacaa aacagacctt aaaaccctaa    4800
aggcttaagt agcaccctcg caagctcggt tgcggccgca atcgggcaaa tcgctgaata    4860
ttccttttgt ctccgaccat caggcacctg agtcgctgtc tttttcgtga cattcagttc    4920
gctgcgctca cggctctggc agtgaatggg ggtaaatggc actacaggcg ccttttatgg    4980
attcatgcaa ggaaactacc cataatacaa gaaaagcccg tcacgggctt ctcagggcgt    5040 tttatgcgg gtctgctatg tggtgctatc tgactttttg ctgttcagca gttcctgccc    5100
tctgattttc cagtctgacc acttcggatt atcccgtgac aggtcattca gactggctaa    5160
tgcacccagt aaggcagcgg tatcatcaac ggggtctgac gctcagtgga acgaaaactc    5220
acgttaaggg attttggtca tgagattatc aaaaaggatc ttcacctaga tccttttaaa    5280
ttaaaaatga agttttaaat caatctaaag tatatatgag taaacttggt ctgacagtta    5340
ccaatgctta atcagtgagg cacctatctc agcgatctgt ctatttcgtt catccatagt    5400
tgcctgactc cccgtcgtgt agataactac gatacgggag ggcttaccat ctggccccag    5460
tgctgcaatg ataccgcgag acccacgctc accggctcca gatttatcag caataaacca    5520
gccagccgga agggccgagc gcagaagtgg tcctgcaact ttatccgcct ccatccagtc    5580
tattaattgt tgccgggaag ctagagtaag tagttcgcca gttaatagtt tgcgcaacgt    5640
tgttgccatt gctacaggca tcgtggtgtc acgctcgtcg tttggtatgg cttcattcag    5700
ctccggttcc caacgatcaa ggcgagttac atgatccccc atgttgtgca aaaaagcggt    5760
tagctccttc ggtcctccga tcgttgtcag aagtaagttg gccgcagtgt tatcactcat    5820
ggttatggca gcactgcata attctcttac tgtcatgcca tccgtaagat gcttttctgt    5880
```

```
gactggtgag tactcaacca agtcattctg agaatagtgt atgcggcgac cgagttgctc    5940
ttgcccggcg tcaatacggg ataataccgc gccacatagc agaactttaa aagtgctcat    6000
cattggaaaa cgttcttcgg ggcgaaaact ctcaaggatc ttaccgctgt tgagatccag    6060
ttcgatgtaa cccactcgtg cacccaactg atcttcagca tcttttactt tcaccagcgt    6120
ttctgggtga gcaaaaacag gaaggcaaaa tgccgcaaaa agggaataag ggcgacacg     6180 gaaatgttga atactcatac tcttccttt tcaatattat tgaagcattt atcagggtta    6240
ttgtctcatg agcggataca tatttgaatg tatttagaaa aataaacaaa tagggggttcc   6300 gcgcacattt ccccgaaaag tgccacctg                                     6329

<210> SEQ ID NO 34
<211> LENGTH: 25
<212> TYPE: DNA
<213> ORGANISM: Artificial sequence
<220> FEATURE:
<223> OTHER INFORMATION: Primer

<400> SEQUENCE: 34
aacaatatgt aagatctcaa ctatc                                          25

<210> SEQ ID NO 35
<211> LENGTH: 25
<212> TYPE: DNA
<213> ORGANISM: Artificial sequence
<220> FEATURE:
<223> OTHER INFORMATION: Primer

<400> SEQUENCE: 35
cagacatgag agatccagtg tgtag                                          25

<210> SEQ ID NO 36
<211> LENGTH: 9332
<212> TYPE: DNA
<213> ORGANISM: Artificial sequence
<220> FEATURE:
<223> OTHER INFORMATION: Plasmid pCP20

<400> SEQUENCE: 36
gagacacaac gtggctttgt tgaataaatc gaacttttgc tgagttgaag gatcagatca     60
cgcatcttcc cgacaacgca gaccgttccg tggcaaagca aaagttcaaa atcaccaact    120
ggtccaccta caacaaagct ctcatcaacc gtggctccct cactttctgg ctggatgatg    180
gggcgattca ggcctggtat gagtcagcaa caccttcttc acgaggcaga cctcagcgcc    240
acaggtgcgg ttgctggcgc taaccgtttt tatcaggctc tgggaggcag aataaatgat    300
catatcgtca attattacct ccacggggag agcctgagca aactggcctc aggcatttga    360
gaagcacacg gtcacactgc ttccggtagt caataaaccg gtaaaccagc aatagacata    420
agcggctatt taacgaccct gccctgaacc gacgaccggg tcgaatttgc tttcgaattt    480
ctgccattca tccgcttatt atcacttatt caggcgtagc aaccaggcgt ttaagggcac    540
caataactgc cttaaaaaaa ttacgccccg ccctgccact catcgcagta ctgttgtaat    600
tcattaagca ttctgccgac atggaagcca tcacaaacgg catgatgaac ctgaatcgcc    660
agcggcatca gcaccttgtc gccttgcgta taatatttgc ccatggtgaa acggggggcg    720
aagaagttgt ccatattggc cacgtttaaa tcaaaactgg tgaaactcac ccagggattg    780
gctgagacga aaaacatatt ctcaataaac cctttaggga ataggccag gttttcaccg    840 taacacgcca catcttgcga atatatgtgt agaaactgcc ggaaatcgtc gtggtattca    900
```

| | |
|---|---|
| ctccagagcg atgaaaacgt tcagtttgc tcatggaaaa cggtgtaaca agggtgaaca | 960 |
| ctatcccata tcaccagctc accgtctttc attgccatac ggaattccgg atgagcattc | 1020 |
| atcaggcggg caagaatgtg aataaaggcc ggataaaact tgtgcttatt tttctttacg | 1080 |
| gtctttaaaa aggccgtaat atccagctga acggtctggt tataggtaca ttgagcaact | 1140 |
| gactgaaatg cctcaaaatg ttctttacga tgccattggg atatatcaac ggtggtatat | 1200 |
| ccagtgattt ttttctccat tttagcttcc ttagctcctg aaaatctcga taactcaaaa | 1260 |
| aatacgcccg gtagtgatct tatttcatta tggtgaaagt tggaacctct tacgtgccga | 1320 |
| tcaacgtctc attttcgcca aaagttggcc caggcttcc cggtatcaac agggacacca | 1380 |
| ggatttattt attctgcgaa gtgatcttcc gtcacaggta tttattcggc gcaaagtgcg | 1440 |
| tcgggtgatg ctgccaactt actgatttag tgtatgatgg tgttttgag gtgctccagt | 1500 |
| ggcttctgtt tctatcagct gtccctcctg ttcagctact gacggggtgg tgcgtaacgg | 1560 |
| caaaagcacc gccggacatc agcgcttgtt tcggcgtggg tatggtggca ggccccgtgg | 1620 |
| ccgggggact gttgggcgcc tgtagtgcca tttacccca ttcactgcca gagccgtgag | 1680 |
| cgcagcgaac tgaatgtcac gaaaaagaca gcgactcagg tgcctgatgg tcggagacaa | 1740 |
| aaggaatatt cagcgatttg cccgagcttg cgagggtgct acttaagcct ttagggtttt | 1800 |
| aaggtctgtt ttgtagagga gcaaacagcg tttgcgacat ccttttgtaa tactgcggaa | 1860 |
| ctgactaaag tagtgagtta tacacagggc tgggatctat tcttttatc ttttttatt | 1920 |
| cttttcttat tctataaatt ataaccactt gaatataaac aaaaaaaca cacaaaggtc | 1980 |
| tagcggaatt tacagagggt ctagcagaat ttacaagttt tccagcaaag gtctagcaga | 2040 |
| atttacagat acccacaact caaggaaaa ggactagtaa ttatcattga ctagcccatc | 2100 |
| tcaattggta tagtgattaa aatcacctag accaattgag atgtatgtct gaattagttg | 2160 |
| ttttcaaagc aaatgaacta gcgattagtc gctatgactt aacggagcat gaaaccaagc | 2220 |
| taattttatg ctgtgtggca ctactcaacc ccacgattga aaaccctaca aggaaagaac | 2280 |
| ggacggtatc gttcacttat aaccaatacg ttcagatgat gaacatcagt agggaaaatg | 2340 |
| cttatggtgt attagctaaa gcaaccagag agctgatgac gagaactgtg gaaatcagga | 2400 |
| atcctttggt taaaggcttt gagattttcc agtggacaaa ctatgccaag ttctcaagcg | 2460 |
| aaaaattaga attagttttt agtgaagaga tattgcctta tcttttccag ttaaaaaaat | 2520 |
| tcataaaata taatctggaa catgttaagt cttttgaaaa caaatactct atgaggattt | 2580 |
| atgagtggtt attaaaagaa ctaacacaaa agaaaactca caggcaaat atagagatta | 2640 |
| gccttgatga atttaagttc atgttaatgc ttgaaaataa ctaccatgag tttaaaggc | 2700 |
| ttaaccaatg ggttttgaaa ccaataagta aagatttaaa cacttacagc aatatgaaat | 2760 |
| tggtggttga taagcgaggc cgcccgactg atacgttgat tttccaagtt gaactagata | 2820 |
| gacaaatgga tctcgtaacc gaacttgaga caaccagat aaaatgaat ggtgacaaaa | 2880 |
| taccaacaac cattacatca gattcctacc tacataacgg actaagaaaa acactacacg | 2940 |
| atgctttaac tgcaaaaatt cagctcacca gttttgaggc aaaattttg agtgacatgc | 3000 |
| aaagtaagta tgatctcaat ggttcgttct catggctcac gcaaaaacaa cgaaccacac | 3060 |
| tagagaacat actggctaaa tacgaagga tctgaggttc ttatggctct tgtatctatc | 3120 |
| agtgaagcat caagactaac aaacaaaagt agaacaactg ttcaccgtta catatcaaag | 3180 |
| ggaaaactgt ccatatgcac agatgaaaac ggtgtaaaaa agatagatac atcagagctt | 3240 |
| ttacgagttt ttggtgcatt taaagctgtt caccatgaac agatcgacaa tgtaacagat | 3300 |

```
gaacagcatg taacacctaa tagaacaggt gaaaccagta aaacaaagca actagaacat    3360
gaaattgaac acctgagaca acttgttaca gctcaacagt cacacataga cagcctgaaa    3420
caggcgatgc tgcttatcga atcaaagctg ccgacaacac gggagccagt gacgcctccc    3480
gtggggaaaa aatcatggca attctggaag aaatagcgcc tgtttcgttt caggcaggtt    3540
atcagggagt gtcagcgtcc tgcggttctc cggggcgttc gggtcatgca gcccgtaatg    3600
gtgatttacc agcgtctgcc aggcatcaat tctaggcctg tctgcgcggt cgtagtacgg    3660
ctggaggcgt tttccggtct gtagctccat gttcggaatg acaaaattca gctcaagccg    3720
tcccttgtcc tggtgctcca cccacaggat gctgtactga ttttttttcga gaccgggcat    3780 cagtacacgc tcaaagctcg ccatcacttt ttcacgtcct cccggcggca gctccttctc    3840
cgcgaacgac agaacaccgg acgtgtattt cttcgcaaat ggcgtggcat cgatgagttc    3900
ccggacttct tccggattac cctgaagcac cgttgcgcct tcgcggttac gctccctccc    3960
cagcaggtaa tcaaccggac cactgccacc acctttccc  ctggcatgaa atttaactat    4020
catcccgcgc ccctgttcc  ctgacagcca gacgcagccg gcgcagctca tccccgatgg    4080
ccatcagtgc ggccaccacc tgaacccggt caccggaaga ccactgcccg ctgttcacct    4140
tacgggctgt ctgattcagg ttatttccga tggcggccag ctgacgcagt aacggcggtg    4200
ccagtgtcgg cagttttccg gaacgggcaa ccggctcccc caggcagacc cgccgcatcc    4260
ataccgccag ttgtttaccc tcacagcgtt caagtaaccg ggcatgttca tcatcagtaa    4320
cccgtattgt gagcatcctc tcgcgtttca tcggtatcat taccccatga acagaaatcc    4380
cccttacacg gaggcatcag tgactaaacg gggtctgacg ctcagtggaa cgaaaactca    4440
cgttaaggga ttttggtcat gagattatca aaaaggatct tcacctagat ccttttaaat    4500
taaaaatgaa gttttaaatc aatctaaagt atatatgagt aaacttggtc tgacagttac    4560
caatgcttaa tcagtgaggc acctatctca gcgatctgtc tatttcgttc atccatagtt    4620
gcctgactcc ccgtcgtgta gataactacg atacgggagg gcttaccatc tggccccagt    4680
gctgcaatga taccgcgaga cccacgctca ccggctccag atttatcagc aataaaccag    4740
ccagccggaa gggccgagcg cagaagtggt cctgcaactt tatccgcctc catccagtct    4800
attaattgtt gccgggaagc tagagtaagt agttcgccag ttaatagttt gcgcaacgtt    4860
gttgccattg ctgcaggcat cgtggtgtca cgctcgtcgt ttggtatggc ttcattcagc    4920
tccggttccc aacgatcaag gcgagttaca tgatccccca tgttgtgcaa aaaagcggtt    4980
agctccttcg gtcctccgat cgttgtcaga agtaagttgg ccgcagtgtt atcactcatg    5040
gttatggcag cactgcataa ttctcttact gtcatgccat ccgtaagatg cttttctgtg    5100
actggtgagt actcaaccaa gtcattctga gaatagtgta tgcggcgacc gagttgctct    5160
tgcccggcgt caacacggga taataccgcg ccacatagca gaactttaaa agtgctcatc    5220
attggaaaac gttcttcggg gcgaaaactc tcaaggatct taccgctgtt gagatccagt    5280
tcgatgtaac ccactcgtgc acccaactga tcttcagcat cttttacttt caccagcgtt    5340
tctgggtgag caaaaacagg aaggcaaaat gccgcaaaaa agggaataag ggcgacacgg    5400
aaatgttgaa tactcatact cttcctttt  caatattatt gaagcattta tcagggttat    5460
tgtctcatga gcggatacat atttgaatgt atttagaaaa ataaacaaat aggggttccg    5520
cgcacatttc cccgaaaagt gccacctgac gtctaagaaa ccattattat catgacatta    5580
acctataaaa ataggcgtat cacgaggccc tttcgtcttc aagaattta  taaaccgtgg    5640 agcgggcaat actgagctga tgagcaattt ccgttgcacc agtgcccttc tgatgaagcg    5700
```

```
tcagcacgac gttcctgtcc acggtacgcc tgcggccaaa tttgattcct ttcagctttg    5760
cttcctgtcg gccctcattc gtgcgctcta ggatcctcta cgccggacgc atcgtggccg    5820
gcatcaccgg cgctgaggtc tgcctcgtga agaaggtgtt gctgactcat accaggcctg    5880
aatcgcccca tcatccagcc agaaagtgag ggagccacgg ttgatgagag ctttgttgta    5940
ggtggaccag ttggtgattt tgaactttg ctttgccacg gaacggtctg cgttgtcggg     6000
aagatgcgtg atctgatcct tcaactcagc aaaagttcga tttattcaac aaagccgccg    6060
tcccgtcaag tcagcgtaat gctctgccag tgttacaacc aattaaccaa ttctgattag    6120
aaaaactcat cgagcatcaa atgaaactgc aatttattca tatcaggatt atcaatacca    6180 tattttgaa aaagccgttt ctgtaatgaa ggagaaaact caccgaggca gttccatagg      6240
atggcaagat cctggtatcg gtctgcgatt ccgactcgtc caacatcaat acaacctatt    6300
aatttcccct cgtcaaaaat aaggttatca agtgagaaat caccatgagt gacgactgaa    6360
tccggtgaga atggcagaat aggaacttcg gaataggaac ttcaaagcgt ttccgaaaac    6420
gagcgcttcc gaaaatgcaa cgcgagctgc gcacatacag ctcactgttc acgtcgcacc    6480
tatatctgcg tgttgcctgt atatatatat acatgagaag aacggcatag tgcgtgttta    6540
tgcttaaatg cgtacttata tgcgtctatt tatgtaggat gaaaggtagt ctagtacctc    6600
ctgtgatatt atcccattcc atgcggggta tcgtatgctt ccttcagcac taccctttag    6660
ctgttctata tgctgccact cctcaattgg attagtctca tccttcaatg ctatcatttc    6720
ctttgatatt ggatcatatg catagtaccg agaaactagt gcgaagtagt gatcaggtat    6780
tgctgttatc tgatgagtat acgttgtcct ggccacggca gaagcacgct tatcgctcca    6840
atttcccaca acattagtca actccgttag gcccttcatt gaaagaaatg aggtcatcaa    6900
atgtcttcca atgtgagatt tgggccatt ttttatagca aagattgaat aaggcgcatt      6960
tttcttcaaa gctttattgt acgatctgac taagtatct tttataatt ggtattcctg        7020 tttattgctt gaagaattgc cggtcctatt tactcgtttt aggactggtt cagaattcct    7080
caaaaattca tccaaatata caagtggatc gatcctaccc cttgcgctaa agaagtatat    7140
gtgcctacta acgcttgtct ttgtctctgt cactaaacac tggattatta ctcccagata    7200
cttattttgg actaatttaa atgatttcgg atcaacgttc ttaatatcgc tgaatcttcc    7260
acaattgatg aaagtagcta ggaagaggaa ttggtataaa gttttgttt ttgtaaatct     7320 cgaagtatac tcaaacgaat ttagtatttt ctcagtgatc tcccagatgc tttcaccctc    7380
acttagaagt gctttaagca tttttttact gtggctattt cccttatctg cttcttccga    7440
tgattcgaac tgtaattgca aactacttac aatatcagtg atatcagatt gatgttttg     7500 tccatagtaa ggataattg taaattccca agcaggaatc aatttcttta atgaggcttc      7560
cagaattgtt gctttttgcg tcttgtattt aaactggagt gatttattga caatatcgaa    7620
actcagcgaa ttgcttatga tagtattata gctcatgaat gtggctctct tgattgctgt    7680
tccgttatgt gtaatcatcc aacataaata ggttagttca gcagcacata atgctatttt    7740
ctcacctgaa ggtctttcaa acctttccac aaactgacga acaagcacct taggtggtgt    7800
tttacataat atatcaaatt gtggcataca acctccttag tacatgcaac cattatcacc    7860
gccagaggta aaatagtcaa cacgcacggt gttagatatt tatccccttgc ggtgatagat  7920 ttaacgtatg agcacaaaaa agaaaccatt aacacaagag cagcttgagg acgcacgtcg    7980
ccttaaagca atttatgaaa aaagaaaaa tgaacttggc ttatcccagg aatctgtcgc      8040
agacaagatg gggatggggc agtcaggcgt tggtgcttta tttaatggca tcaatgcatt    8100
```

```
aaatgcttat aacgccgcat tgcttacaaa aattctcaaa gttagcgttg aagaatttag   8160
cccttcaatc gccagagaaa tctacgagat gtatgaagcg gttagtatgc agccgtcact   8220
tagaagtgag tatgagtacc ctgttttttc tcatgttcag gcagggatgt tctcacctaa   8280
gcttagaacc tttaccaaag gtgatgcgga gagatgggta agcacaacca aaaaagccag   8340
tgattctgca ttctggcttg aggttgaagg taattccatg accgcaccaa caggctccaa   8400
gccaagcttt cctgacggaa tgttaattct cgttgaccct gagcaggctg ttgagccagg   8460
tgatttctgc atagccagac ttggggggtga tgagtttacc ttcaagaaac tgatcaggga   8520
tagcggtcag gtgttttttac aaccactaaa cccacagtac ccatgatcc catgcaatga    8580 gagttgttcc gttgtgggga agttatcgc tagtcagtgg cctgaagaga cgtttggctg     8640
atcggcaagg tgttctggtc ggcgcatagc tgataacaat tgagcaagaa tctgcatttc    8700
tttccagact tgttcaacag gccagccatt acgctcgtca tcaaaatcac tcgcatcaac    8760
caaaccgtta ttcattcgtg attgcgcctg agcgagacga aatacgcgat cgctgttaaa    8820
aggacaatta caaacaggaa tcgaatgcaa ccggcgcagg aacactgcca gcgcatcaac    8880
aatattttca cctgaatcag gatattcttc taatacctgg aatgctgttt tcccggggat    8940
cgcagtggtg agtaaccatg catcatcagg agtacggata aaatgcttga tggtcggaag    9000
aggcataaat tccgtcagcc agtttagtct gaccatctca tctgtaacat cattggcaac    9060
gctacctttg ccatgtttca gaaacaactc tggcgcatcg gcttcccat acaatcgata     9120 gattgtcgca cctgattgcc cgacattatc gcgagcccat ttatacccat ataaatcagc    9180
atccatgttg gaatttaatc gcggcctcga gcaagacgtt tcccgttgaa tatggctcat    9240
aacacccctt gtattactgt ttatgtaagc agacagtttt attgttcatg atgatatatt    9300
tttatcttgt gcaatgtaac atcagagatt tt                                  9332
```

<210> SEQ ID NO 37
<211> LENGTH: 80
<212> TYPE: DNA
<213> ORGANISM: Artificial sequence
<220> FEATURE:
<223> OTHER INFORMATION: Primer

<400> SEQUENCE: 37

```
atgtcgcaac ataacgaaaa gaacccacat cagcaccagt caccactaca cgattccagc   60
gtgtaggctg gagctgcttc                                                80
```

<210> SEQ ID NO 38
<211> LENGTH: 82
<212> TYPE: DNA
<213> ORGANISM: Artificial sequence
<220> FEATURE:
<223> OTHER INFORMATION: Primer

<400> SEQUENCE: 38

```
ttacgccggg attttgtcaa tcttaggaat gcgtgaccac acgcggtgtg ctgtcatcag   60
attccgggga tccgtcgacc tg                                            82
```

<210> SEQ ID NO 39
<211> LENGTH: 1424
<212> TYPE: DNA
<213> ORGANISM: Artificial sequence
<220> FEATURE:
<223> OTHER INFORMATION: Synthetic construct

<400> SEQUENCE: 39

-continued

```
ttacgccggg attttgtcaa tcttaggaat gcgtgaccac acgcggtgtg ctgtcatcag      60
attccgggga tccgtcgacc tgcagttcga agttcctatt ctctagaaag tataggaact     120
tcagagcgct tttgaagctc acgctgccgc aagcactcag ggcgcaaggg ctgctaaagg     180
aagcggaaca cgtagaaagc cagtccgcag aaacggtgct gaccccggat gaatgtcagc     240
tactgggcta tctggacaag gaaaacgca agcgcaaaga gaaagcaggt agcttgcagt     300
gggcttacat ggcgatagct agactgggcg gttttatgga cagcaagcga accggaattg     360
ccagctgggg cgccctctgg taaggttggg aagccctgca agtaaactg gatggctttc      420 ttgccgccaa ggatctgatg cgcagggga tcaagatctg atcaagagac aggatgagga     480
tcgtttcgca tgattgaaca agatggattg cacgcaggtt ctccggccgc ttgggtggag     540
aggctattcg ctatgactg gcacaacag acaatcggct gctctgatgc cgccgtgttc      600
cggctgtcag cgcaggggcg cccggttctt tttgtcaaga ccgacctgtc cggtgccctg     660
aatgaactgc aggacgaggc agcgcggcta tcgtggctgg ccacgacggg cgttccttgc     720
gcagctgtgc tcgacgttgt cactgaagcg ggaagggact ggctgctatt gggcgaagtg     780
ccggggcagg atctcctgtc atctcacctt gctcctgccg agaaagtatc catcatggct     840
gatgcaatgc ggcggctgca tacgcttgat ccggctacct gcccattcga ccaccaagcg     900
aaacatcgca tcgagcgagc acgtactcgg atggaagccg gtcttgtcga tcaggatgat     960
ctggacgaag agcatcaggg gctcgcgcca gccgaactgt tcgccaggct caaggcgcgc    1020
atgcccgacg gcgaggatct cgtcgtgacc catggcgatg cctgcttgcc gaatatcatg    1080
gtggaaaatg gccgcttttc tggattcatc gactgtggcc ggctgggtgt ggcggaccgc    1140
tatcaggaca tagcgttggc tacccgtgat attgctgaag agcttggcgg cgaatgggct    1200
gaccgcttcc tcgtgcttta cggtatcgcc gctcccgatt cgcagcgcat cgccttctat    1260
cgccttcttg acgagttctt ctaataaggg gatcttgaag ttcctattcc gaagttccta    1320
ttctctagaa agtataggaa cttcgaagca gctccagcct acacgctgga atcgtgtagt    1380
ggtgactggt gctgatgtgg gttcttttcg ttatgttgcg acat                     1424
```

<210> SEQ ID NO 40
<211> LENGTH: 2262
<212> TYPE: DNA
<213> ORGANISM: Escherichia coli

<400> SEQUENCE: 40

```
atgtcgcaac ataacgaaaa gaacccacat cagcaccagt caccactaca cgattccagc      60
gaagcgaaac cggggatgga ctcactggca cctgaggacg gctctcatcg tccagcggct     120
gaaccaacac cgccaggtgc acaacctacc gccccaggga gcctgaaagc ccctgatacg     180
cgtaacgaaa aacttaattc tctggaagac gtacgcaaag cagtgaaaa ttatgcgctg     240 accactaatc agggcgtgcg catcgccgac gatcaaaact cactgcgtgc cggtagccgt     300
ggtccaacgc tgctggaaga ttttattctg cgcgagaaaa tcacccactt tgaccatgag     360
cgcattccgg aacgtattgt tcatgcacgc ggatcagccg ctcacggtta tttccagcca     420
tataaaagct aagcgatat taccaaagcg gatttcctct cagatccgaa caaaatcacc     480
ccagtatttg tacgtttctc taccgttcag ggtggtgctg gctctgctga taccgtgcgt     540
gatatccgtg gctttgccac caagttctat accgaagagg gtattttga cctcgttggc     600 aataacacgc caatcttctt tatccaggat gcgcataaat tccccgattt tgttcatgcg     660
gtaaaaccag aaccgcactg ggcaattcca caagggcaaa gtgcccacga tacttttctgg     720
```

```
gattatgttt ctctgcaacc tgaaactctg cacaacgtga gtgggcgat gtcggatcgc    780
ggcatccccc gcagttaccg caccatggaa ggcttcggta ttcacacctt ccgcctgatt    840
aatgccgaag ggaaggcaac gtttgtacgt ttccactgga aaccactggc aggtaaagcc    900
tcactcgttt gggatgaagc acaaaaactc accggacgtg acccggactt ccaccgccgc    960
gagttgtggg aagccattga agcaggcgat tttccggaat acgaactggg cttccagttg   1020
attcctgaag aagatgaatt caagttcgac ttcgatcttc tcgatccaac caaacttatc   1080
ccggaagaac tggtgcccgt tcagcgtgtc ggcaaaatgg tgctcaatcg caacccggat   1140
aacttctttg ctgaaaacga acaggcggct ttccatcctg gcatatcgt gccgggactg   1200
gacttcacca acgatccgct gttgcaggga cgtttgttct cctataccga tacacaaatc   1260
agtcgtcttg gtgggccgaa tttccatgag attccgatta accgtccgac ctgcccttac   1320
cataatttcc agcgtgacgg catgcatcgc atggggatcg acactaaccc ggcgaattac   1380
gaaccgaact cgattaacga taactggccg cgcgaaacac cgccggggcc gaaacgcggc   1440
ggttttgaat cataccagga gcgcgtggaa ggcaataaag ttcgcgagcg cagcccatcg   1500
tttggcgaat attattccca tccgcgtctg ttctggctaa gtcagacgcc atttgagcag   1560
cgccatattg tcgatggttt cagttttgag ttaagcaaag tcgttcgtcc gtatattcgt   1620
gagcgcgttg ttgaccagct ggcgcatatt gatctcactc tggcccaggc ggtggcgaaa   1680
aatctcggta tcgaactgac tgacgaccag ctgaatatca ccccacctcc ggacgtcaac   1740
ggtctgaaaa aggatccatc cttaagtttg tacgccattc ctgacggtga tgtgaaaggt   1800
cgcgtggtag cgattttact taatgatgaa gtgagatcgg cagaccttct ggccattctc   1860
aaggcgctga aggccaaagg cgttcatgcc aaactgctct actcccgaat gggtgaagtg   1920
actgcggatg acggtacggt gttgcctata gccgctacct tgccggtgc accttcgctg   1980
acggtcgatg cggtcattgt cccttgcggc aatatcgcgg atatcgctga caacggcgat   2040
gccaactact acctgatgga agcctacaaa caccttaaac cgattgcgct ggcgggtgac   2100
gcgcgcaagt ttaaagcaac aatcaagatc gctgaccagg gtgaagaagg gattgtggaa   2160
gctgacagcg ctgacggtag ttttatggat gaactgctaa cgctgatggc agcacaccgc   2220
gtgtggtcac gcattcctaa gattgacaaa attcctgcct ga                     2262
```

<210> SEQ ID NO 41
<211> LENGTH: 753
<212> TYPE: PRT
<213> ORGANISM: Escherichia coli

<400> SEQUENCE: 41

Met Ser Gln His Asn Glu Lys Asn Pro His Gln His Gln Ser Pro Leu
1               5                   10                  15

His Asp Ser Ser Glu Ala Lys Pro Gly Met Asp Ser Leu Ala Pro Glu
            20                  25                  30

Asp Gly Ser His Arg Pro Ala Ala Glu Pro Thr Pro Pro Gly Ala Gln
        35                  40                  45

Pro Thr Ala Pro Gly Ser Leu Lys Ala Pro Asp Thr Arg Asn Glu Lys
    50                  55                  60

Leu Asn Ser Leu Glu Asp Val Arg Lys Gly Ser Glu Asn Tyr Ala Leu
65                  70                  75                  80

Thr Thr Asn Gln Gly Val Arg Ile Ala Asp Asp Gln Asn Ser Leu Arg
                85                  90                  95

Ala Gly Ser Arg Gly Pro Thr Leu Leu Glu Asp Phe Ile Leu Arg Glu
            100                 105                 110

-continued

Lys Ile Thr His Phe Asp His Glu Arg Ile Pro Glu Arg Ile Val His
            115                 120                 125

Ala Arg Gly Ser Ala Ala His Gly Tyr Phe Gln Pro Tyr Lys Ser Leu
        130                 135                 140

Ser Asp Ile Thr Lys Ala Asp Phe Leu Ser Asp Pro Asn Lys Ile Thr
145                 150                 155                 160

Pro Val Phe Val Arg Phe Ser Thr Val Gln Gly Ala Gly Ser Ala
                165                 170                 175

Asp Thr Val Arg Asp Ile Arg Gly Phe Ala Thr Lys Phe Tyr Thr Glu
                180                 185                 190

Glu Gly Ile Phe Asp Leu Val Gly Asn Asn Thr Pro Ile Phe Phe Ile
            195                 200                 205

Gln Asp Ala His Lys Phe Pro Asp Phe Val His Ala Val Lys Pro Glu
        210                 215                 220

Pro His Trp Ala Ile Pro Gln Gly Gln Ser Ala His Asp Thr Phe Trp
225                 230                 235                 240

Asp Tyr Val Ser Leu Gln Pro Glu Thr Leu His Asn Val Met Trp Ala
                245                 250                 255

Met Ser Asp Arg Gly Ile Pro Arg Ser Tyr Arg Thr Met Glu Gly Phe
                260                 265                 270

Gly Ile His Thr Phe Arg Leu Ile Asn Ala Glu Gly Lys Ala Thr Phe
            275                 280                 285

Val Arg Phe His Trp Lys Pro Leu Ala Gly Lys Ala Ser Leu Val Trp
        290                 295                 300

Asp Glu Ala Gln Lys Leu Thr Gly Arg Asp Pro Asp Phe His Arg Arg
305                 310                 315                 320

Glu Leu Trp Glu Ala Ile Glu Ala Gly Asp Phe Pro Glu Tyr Glu Leu
                325                 330                 335

Gly Phe Gln Leu Ile Pro Glu Gly Asp Glu Phe Lys Phe Asp Phe Asp
                340                 345                 350

Leu Leu Asp Pro Thr Lys Leu Ile Pro Glu Glu Leu Val Pro Val Gln
                355                 360                 365

Arg Val Gly Lys Met Val Leu Asn Arg Asn Pro Asp Asn Phe Phe Ala
        370                 375                 380

Glu Asn Glu Gln Ala Ala Phe His Pro Gly His Ile Val Pro Gly Leu
385                 390                 395                 400

Asp Phe Thr Asn Asp Pro Leu Leu Gln Gly Arg Leu Phe Ser Tyr Thr
                405                 410                 415

Asp Thr Gln Ile Ser Arg Leu Gly Gly Pro Asn Phe His Glu Ile Pro
                420                 425                 430

Ile Asn Arg Pro Thr Cys Pro Tyr His Asn Phe Gln Arg Asp Gly Met
            435                 440                 445

His Arg Met Gly Ile Asp Thr Asn Pro Ala Asn Tyr Glu Pro Asn Ser
        450                 455                 460

Ile Asn Asp Asn Trp Pro Arg Glu Thr Pro Pro Gly Pro Lys Arg Gly
465                 470                 475                 480

Gly Phe Glu Ser Tyr Gln Glu Arg Val Glu Gly Asn Lys Val Arg Glu
                485                 490                 495

Arg Ser Pro Ser Phe Gly Glu Tyr Tyr Ser His Pro Arg Leu Phe Trp
                500                 505                 510

Leu Ser Gln Thr Pro Phe Glu Gln Arg His Ile Val Asp Gly Phe Ser
        515                 520                 525

Phe Glu Leu Ser Lys Val Val Arg Pro Tyr Ile Arg Glu Arg Val Val

```
                    530            535            540
Asp Gln Leu Ala His Ile Asp Leu Thr Leu Ala Gln Ala Val Ala Lys
545                 550            555            560

Asn Leu Gly Ile Glu Leu Thr Asp Asp Gln Leu Asn Ile Thr Pro Pro
                565            570            575

Pro Asp Val Asn Gly Leu Lys Lys Asp Pro Ser Leu Ser Leu Tyr Ala
            580            585            590

Ile Pro Asp Gly Asp Val Lys Gly Arg Val Val Ala Ile Leu Leu Asn
        595            600            605

Asp Glu Val Arg Ser Ala Asp Leu Leu Ala Ile Leu Lys Ala Leu Lys
        610            615            620

Ala Lys Gly Val His Ala Lys Leu Leu Tyr Ser Arg Met Gly Glu Val
625            630            635            640

Thr Ala Asp Asp Gly Thr Val Leu Pro Ile Ala Ala Thr Phe Ala Gly
                645            650            655

Ala Pro Ser Leu Thr Val Asp Ala Val Ile Val Pro Cys Gly Asn Ile
            660            665            670

Ala Asp Ile Ala Asp Asn Gly Asp Ala Asn Tyr Tyr Leu Met Glu Ala
        675            680            685

Tyr Lys His Leu Lys Pro Ile Ala Leu Ala Gly Asp Ala Arg Lys Phe
690            695            700

Lys Ala Thr Ile Lys Ile Ala Asp Gln Gly Glu Gly Ile Val Glu
705            710            715            720

Ala Asp Ser Ala Asp Gly Ser Phe Met Asp Glu Leu Leu Thr Leu Met
                725            730            735

Ala Ala His Arg Val Trp Ser Arg Ile Pro Lys Ile Asp Lys Ile Pro
            740            745            750

Ala

<210> SEQ ID NO 42
<211> LENGTH: 25
<212> TYPE: DNA
<213> ORGANISM: Artificial sequence
<220> FEATURE:
<223> OTHER INFORMATION: Primer

<400> SEQUENCE: 42
gatctgactg gtggtctata gttag                                              25

<210> SEQ ID NO 43
<211> LENGTH: 25
<212> TYPE: DNA
<213> ORGANISM: Artificial sequence
<220> FEATURE:
<223> OTHER INFORMATION: Primer

<400> SEQUENCE: 43
gtagttatca tgatgtgtaa gtaag                                              25

<210> SEQ ID NO 44
<211> LENGTH: 978
<212> TYPE: DNA
<213> ORGANISM: Thermotoga neapolitana

<400> SEQUENCE: 44
atggccttct tcgatatgcc ccttgaggaa ctgaaaaagt accggcctga aggtacgag         60 gagaaagatt tcgatgagtt ctggagggaa acacttaaag aaagcgaagg attccctctg      120
gatcccgtct ttgaaaaggt ggactttcat ctcaaaacgg ttgaaacgta cgatgttact      180
```

```
ttctctggat acaggggca gagaataaag ggctggcttc ttgttccgaa gttggcggaa      240
gaaaagcttc catgcgtcgt gcagtacata ggttacaatg gtggaagggg ttttccacac      300
gactggctgt tctggccgtc aatgggttac atctgttttg tcatggacac caggggcag      360 ggaagcggct ggatgaaggg agacacaccg gattaccctg agggtccagt cgatccacag      420
taccccggat tcatgacgag ggcattctg gatccgggaa cctattacta caggcgagtc      480
ttcgtggatg cggtcagggc ggtggaagca gccatttcct tcccgagagt ggattccagg      540
aaggtggtgg tggccggagg cagtcagggt gggggaatcg cccttgcggt gagtgccctg      600
tcgaacaggg tgaaggctct gctctgcgat gtgccgtttc tgtgccactt cagaagggcc      660
gtgcaacttg tcgacacaca cccatacgtg gagatcacca acttcctcaa aacccacagg      720
gacaaagagg agattgtttt cagaacactt tcctacttcg atggtgtgaa ctttgcagca      780
agggcaaagg tgcccgccct gttttccgtt gggctcatgg acaccatctg tcctccctcg      840
acggtcttcg ccgcttacaa ccactacgcc ggtccaaagg agatcagaat ctatccgtac      900
aacaaccacg aaggtggagg ttctttccag gcaattgagc aggtgaaatt cttgaagaga      960
ctatttgagg aaggctag                                                   978

<210> SEQ ID NO 45
<211> LENGTH: 24
<212> TYPE: DNA
<213> ORGANISM: Artificial sequence
<220> FEATURE:
<223> OTHER INFORMATION: Primer

<400> SEQUENCE: 45
atggctttct tgacatgcc gctg                                              24

<210> SEQ ID NO 46
<211> LENGTH: 27
<212> TYPE: DNA
<213> ORGANISM: Artificial sequence
<220> FEATURE:
<223> OTHER INFORMATION: Primer

<400> SEQUENCE: 46
ttagccttct tcgaacaggc gtttcag                                          27

<210> SEQ ID NO 47
<211> LENGTH: 978
<212> TYPE: DNA
<213> ORGANISM: Thermotoga neapolitana

<400> SEQUENCE: 47
atggctttct tgacatgcc gctggaagaa ctgaaaaagt accgtccgga acgttacgag       60 gaaaagact ttgacgaatt tggcgcgaa accctgaaag aatccgaggg tttcccactg      120
gacccggtat ttgaaaaagt tgacttccac ctgaagaccg tcgaaactta cgacgtcacc      180
ttcagcggtt atcgtggcca gcgtatcaaa ggttggctgc tggtaccgaa actggcggaa      240
gagaaactgc cgtgtgttgt tcagtacatt ggttacaacg gtggccgtgg tttcccgcac      300
gactggctgt tctggccgtc tatgggttac atctgcttcg ttatggacac ccgtggtcag      360
ggtagcggtt ggatgaaggg tgatactccg gactacccgg aaggtccggt ggacccgcag      420 taccccgggct tcatgacgcg cggcatcctg gatcctggca cctattacta ccgtcgtgtg      480
tttgtcgatg ccgtgcgcgc cgttgaagcc gctatcagct tcccacgcgt cgattctcgt      540
aaagtggtag ttgctggtgg ctctcaaggt ggcggcattg cactggcagt ttccgcgctg      600
```

```
tccaaccgtg ttaaagccct gctgtgcgat gttccgttcc tgtgccactt ccgtcgtgcg      660
gtacagctgg tggacaccca cccgtacgta gaaattacga acttcctgaa aacccatcgt      720
gataaagaag agatcgtatt ccgtaccctg tcttactttg atggcgttaa ttttgcggct      780
cgtgcaaaag taccggcgct gttcagcgta ggtctgatgg acactatttg tccgccgtct      840
accgtattcg cagcctacaa ccactacgct ggtccgaaag aaatccgcat ctacccgtac      900
aacaaccacg aaggtggtgg ttctttccag gcaatcgaac aggttaaatt cctgaaacgc      960
ctgttcgaag aaggctaa                                                   978

<210> SEQ ID NO 48
<211> LENGTH: 978
<212> TYPE: DNA
<213> ORGANISM: Thermotoga maritima

<400> SEQUENCE: 48
atggccttct tcgatttacc actcgaagaa ctgaagaaat atcgtccaga gcggtacgaa       60
gagaaagact tcgatgagtt ctgggaagag acactcgcag agagcgaaaa gttcccctta      120
gaccccgtct tcgagaggat ggagtctcac ctcaaaacga tcgaagcgta cgatgtcacc      180
ttctccggat acaggggaca gaggatcaaa gggtggctcc ttgttccaaa actggaagaa      240
gaaaaacttc cctgcgttgt gcagtacata ggatacaacg gtggaagagg attccctcac      300
gactggctgt tctggccttc tatgggttac atatgtttcg tcatggatac tcgaggtcag      360
ggaagcggct ggctgaaagg agacacaccg gattaccctg agggtcccgt tgaccctcag      420
tatccaggat tcatgacaag aggaatactg gatcccagaa cttactacta cagacgagtc      480
ttcacggacg ctgtcagagc cgttgaagct gctgcttctt ttcctcaggt agatcaagaa      540
agaatcgtga tagctggagg cagtcagggt ggcggaatag cccttgcggt gagcgctctc      600
tcaaagaaag caaaggctct tctgtgcgat gtgccgtttc tgtgtcactt cagaagagca      660
gtacagcttg tggatacgca tccatacgcg gagatcacga actttctaaa gacccacaga      720
gacaaggaag aaatcgtgtt caggactctt tcctatttcg atggagtgaa cttcgcagcc      780
agagcgaaga tccctgcgct gttttctgtg gtctcatgg acaacatttg tcctccttca      840
acggttttcg ctgcctacaa ttactacgct ggaccgaagg aaatcagaat ctatccgtac      900
aacaaccacg agggaggagg ctctttccaa gcggttgaac aggtgaaatt cttgaaaaaa      960
ctatttgaga aaggctaa                                                   978

<210> SEQ ID NO 49
<211> LENGTH: 49
<212> TYPE: DNA
<213> ORGANISM: Artificial sequence
<220> FEATURE:
<223> OTHER INFORMATION: Primer

<400> SEQUENCE: 49
taactgcagt aaggaggaat aggacatggg gttcttcgac ctgcctctg                  49

<210> SEQ ID NO 50
<211> LENGTH: 38
<212> TYPE: DNA
<213> ORGANISM: Artificial sequence
<220> FEATURE:
<223> OTHER INFORMATION: Primer

<400> SEQUENCE: 50
tgatctagat tagcccttct caaacagttt ctttcagg                              38
```

```
<210> SEQ ID NO 51
<211> LENGTH: 1012
<212> TYPE: DNA
<213> ORGANISM: Artificial sequence
<220> FEATURE:
<223> OTHER INFORMATION: Synthetic construct

<400> SEQUENCE: 51
taactgcagt aaggaggaat aggacatggc gttcttcgac ctgcctctgg aagaactgaa      60
gaaataccgt ccagagcgtt acgaagagaa ggacttcgac gagttctggg aggaaactct     120
ggcggagagc gaaaagtttc cgctggaccc agtgttcgag cgtatggaat ctcacctgaa     180
aaccgtggag gcatatgacg ttacttttc tggttaccgt ggccagcgta tcaaaggctg      240
gctgctggtt ccgaaactgg aggaagaaaa actgccgtgc gtagttcagt acatcggtta     300
caacggtggc cgtggctttc cgcacgattg gctgttctgg ccgtctatgg gctacatttg     360
cttcgtcatg gatactcgtg gtcagggttc cggctggctg aaaggcgata ctccggatta     420
tccggagggc ccggtagacc cgcagtaccc tggcttcatg acgcgtggta ttctggatcc     480
gcgtacctat tactatcgcc gcgtttttac cgatgcagtt cgtgccgtag aggccgcggc     540
ttctttccct caggttgacc aggagcgtat tgttatcgct ggtggctccc agggtggcgg     600
catcgccctg gcggtatctg cgctgagcaa gaaagctaag gcactgctgt gtgacgtccc     660
gttcctgtgt cacttccgtc gcgctgttca gctggtagat acccatccgt acgcggagat     720
tactaacttc ctgaaaactc accgcgacaa agaagaaatc gttttccgca ccctgtccta     780
tttcgacggc gttaacttcg cggctcgtgc aaaaattccg gcactgttct ctgttggtct     840
gatggacaac atctgccctc cttctaccgt tttcgcggca tataactatt atgcgggtcc     900
gaaagaaatc cgtatctatc cgtacaacaa ccacgaaggc ggtggtagct ttcaggctgt     960
tgaacaagtg aaattcctga agaaactgtt tgagaagggc taatctagat ca           1012
```

US 8,283,142 B2

STABILIZATION OF PERHYDROLASES

CROSS REFERENCE TO RELATED APPLICATIONS

This application claims the benefit of U.S. Provisional Application Nos. 61/102,505; 61/102,512; 61/102,514; 61/102,520; 61/102,531; and 61/102,539; each filed Oct. 3, 2008, each of which incorporated by reference herein in their entireties.

FIELD OF THE INVENTION

This invention relates to the field of enzymatic peracid synthesis and in situ enzyme catalysis. At least one peroxycarboxylic acid is produced at sufficient concentrations as to be efficacious for the disinfection or sanitization of surfaces, medical instrument sterilization, food processing equipment sterilization, and suitable for use in textile and laundry care applications such as bleaching, destaining, deodorizing, disinfection or sanitization.

BACKGROUND OF THE INVENTION

Peracid compositions have been reported to be effective antimicrobial agents. Methods to clean, disinfect, and/or sanitize hard surfaces, meat products, living plant tissues, and medical devices against undesirable microbial growth have been described (e.g., U.S. Pat. Nos. 6,545,047; 6,183,807; 6,518,307; 5,683,724; and U.S. Patent Application Publication No. 2003/0026846). Peracids have also been reported to be useful in preparing bleaching compositions for laundry detergent applications (U.S. Pat. Nos. 3,974,082; 5,296,161; and 5,364,554).

Peracids can be prepared by the chemical reaction of a carboxylic acid and hydrogen peroxide (see *Organic Peroxides*, Daniel Swern, ed., Vol. 1, pp 313-516; Wiley Interscience, New York, 1971). The reaction is usually catalyzed by a strong inorganic acid, such as concentrated sulfuric acid. The reaction of hydrogen peroxide with a carboxylic acid is an equilibrium reaction, and the production of peracid is favored by the use of an excess concentration of peroxide and/or carboxylic acid, or by the removal of water.

Some peracid-based disinfectants or bleaching agents are comprised of an equilibrium mixture of peracid, hydrogen peroxide, and the corresponding carboxylic acid. One disadvantage of these commercial peracid cleaning systems is that the peracid is oftentimes unstable in solution over time. One way to overcome the stability problem is to generate the peracid prior to use by combining multiple reaction components that are individually stable for extended periods of time. Preferably, the individual reaction components are easy to store, relatively safe to handle, and capable of quickly producing an efficacious concentration of peracid upon mixing.

The CE-7 family of carbohydrate esterases has recently been reported to have perhydrolase activity. These "perhydrolase" enzymes have been demonstrated to be particularly effective for producing peracids from a variety of carboxylic acid ester substrates when combined with a source of peroxygen (See WO2007/070609 and U.S. Patent Application Publication Nos. 2008/0176299 and 2008/176783 to DiCosimo et al.; each herein incorporated by reference in their entireties). Some members of the CE-7 family of carbohydrate esterases have been demonstrated to have perhydrolytic activity sufficient to produce 4000-5000 ppm peracetic acid from acetyl esters of alcohols, diols, and glycerols in 1 minute and up to 9000 ppm between 5 minutes and 30 minutes once the reaction components were mixed (DiCosimo et al., U.S. Patent Application Publication No. 2009/0005590).

The enzymatic peracid generation system described by U.S. 2009/0005590 to DiCosimo et al. is typically based on the use of multiple reaction components that remain separated until the peracid solution is needed. Using this approach overcomes the peracid instability issues associated with storage of many peracid-based disinfectants and bleaching agents. However, specific formulations that provide long term stability of perhydrolase activity when using multicomponent formulations comprising CE-7 carbohydrate esterases remains to be addressed. Of particular concern is the long term storage stability of a CE-7 enzyme having perhydrolysis activity when stored in an organic liquid or solvent having a log P (i.e., the logarithm of the partition coefficient of a substance between octanol and water, where P equals $[solute]_{octanol}/[solute]_{water}$) of less than two. Several of the organic ester substrates previous described by DiCosimo et al. have log P values of less than two.

Organic liquids or solvents can be deleterious to the activity of enzymes, either when enzymes are suspended directly in organic liquids or solvents, or when miscible organic/aqueous single phase liquids or solvents are employed. Two literature publications that review the effects of organic solvents on enzyme activity and structure are: (a) C. Laane et al., *Biotechnol. Bioeng.* 30:81-87 (1987) and (b) Cowan, D. A. and Plant, A., *Biocatalysis in Organic Phase Systems.*, Ch. 7 in *Biocatalysis at Extreme Temperatures*, Kelly, R. W. W. and Adams, M., eds., Amer. Chem. Soc. Symposium Series, Oxford University Press, New York, N.Y., pp 86-107 (1992). Cowan and Plant, supra, note (on page 87) that the art generally recognizes that there is little or no value in using organic solvents having a log $P \leq 2$ to stabilize intracellular enzymes in an organic phase system. Organic solvents having a log P between two and four can be used on a case-by-case basis dependent on enzyme stability, and those having a log P>4 are generally useful in organic phase systems.

Cowan and Plant, supra, further note (on page 91) that the effect of direct exposure of an enzyme dissolved in a single-phase organic-aqueous solvent depends on solvent concentration, solvent/enzyme surface group interactions, and solvent/enzyme hydration shell interactions. Because a solvent's log P value must be sufficiently low so that the solvent is fully miscible with the aqueous phase to produce a single-phase, a single-phase organic-aqueous solvent containing a low log P organic solvent usually has a negative effect on enzyme stability except in low organic solvent concentration applications. Triacetin is reported to have a log P of 0.25 (Y. M. Gunning, et al., *J. Agric. Food Chem.* 48:395-399 (2000)), similar to that of ethanol (log P −0.26) and isopropanol (log P 0.15) (Cowan and Plant); therefore the storage of enzyme powder in triacetin would be expected to result in unacceptable loss of enzyme activity, as would the use of additional cosolvents with log P<2 (e.g., cyclohexanone, log P=0.94) (Cowan and Plant); 1,2-propanediol, log P=−1.41 (Gunning, et al.); 1,3-propanediol, log P=−1.3 (S-J. Kuo, et al., *J. Am. Oil Chem. Soc.* 73:1427-1433 (1996); diethylene glycol butyl ether, log P=0.56 (N. Funasaki, et al., *J. Phys. Chem.* 88:5786-5790 (1984); triethyleneglycol, log P=−1.75 (L. Braeken, et al., *Chem Phys Chem* 6:1606-1612 (2005)).

Thus, the problem to be solved is to formulate a product using a mixture of a peracid-generating enzyme in an organic ester substrate employed for peracid production, where the enzyme retains significant perhydrolase activity even when stored in a mixture with the carboxylic acid ester substrate.

SUMMARY OF THE INVENTION

The stated problem has been solved by the discovery of a process for stabilizing the perhydrolysis activity of at least one enzyme structurally classified as a CE-7 enzyme and having perhydrolysis activity when present in a formulation with a carboxylic acid ester. More specifically, the addition of at least one buffer to a formulation comprising a carboxylic acid ester and an enzyme powder comprising the CE-7 enzyme and at least one excipient enhances the stability of the perhydrolysis activity of the CE-7 enzyme stored in the formulation.

In one aspect, a process to stabilize the perhydrolysis activity of an enzyme when present in a formulation comprised of said enzyme and a carboxylic acid ester is provided, the process comprising:
(a) providing an aqueous formulation comprising at least one enzyme structurally classified as a CE-7 enzyme having perhydrolysis activity, at least one excipient, and optionally at least one surfactant;
(b) spray-drying the aqueous formulation of (a) to produce an enzyme powder comprising said at least one enzyme, said at least one oligosaccharide excipient, and optionally said at least one surfactant; and
(c) combining the enzyme powder of (b) with at least one buffer and a carboxylic acid ester to form a formulation, wherein the addition of the at least one buffer to the formulation enhances the stability of the perhydrolysis activity of said at least one enzyme when stored in said formulation.

In another aspect, a formulation used as a first component in a multi-component peracid generation system is provided, said formulation comprising a mixture of:
(a) at least one carboxylic acid ester selected from the group consisting of monoacetin, diacetin, triacetin, monopropionin, dipropionin, tripropionin, monobutyrin, dibutyrin, tributyrin, and mixtures thereof;
(b) an enzyme powder comprising a spray-dried formulation of at least one enzyme structurally classified as a CE-7 enzyme and having perhydrolysis activity, at least one excipient, and optionally at least one surfactant; and
(c) at least one buffer; wherein said at least one buffer enhances the stability of said at least one enzyme when present in said formulation.

In a further aspect, a disinfectant system comprising a first component and a second component is provided, said first component comprising the formulation described above and said second component comprising a source of peroxygen in water and optionally a hydrogen peroxide stabilizer.

In an additional aspect, a process for enzymatically producing a peroxycarboxylic acid is provided comprising:
(a) providing a set of reaction components, said components comprising:
(1) the formulation described above; and
(2) a source of peroxygen in water; and
(b) combining said reaction components whereby a peroxycarboxylic acid is produced.

In another aspect, a process to disinfect or sanitize a hard surface or inanimate object using an enzymatically-produced peroxycarboxylic acid composition is provided, said process comprising:
(a) providing a set of reaction components, said components comprising:
(1) the formulation described above; and
(2) a source of peroxygen in water;
(b) combining said reaction components whereby a peroxycarboxylic acid product is produced;
(c) optionally diluting said peroxycarboxylic acid product; and
(d) contacting said hard surface or inanimate object with the peroxycarboxylic acid produced in step (b) or step (c) whereby said surface or said inanimate object is disinfected.

A further aspect is for a process for treating an article of clothing or a textile for bleaching, stain removal, odor reduction, sanitization or disinfection using an enzymatically-produced peroxycarboxylic acid composition, said process comprising:
(a) providing a set of reaction components, said components comprising:
(1) a formulation comprising
(i) the formulation describe above; and
(ii) a carboxylic acid ester; and
(2) a source of peroxygen;
(b) combining said reaction components under suitable aqueous reaction conditions whereby a peroxycarboxylic acid product is formed;
(c) optionally diluting said peroxycarboxylic acid product; and
(d) contacting said article of clothing or textile fabric with the peroxycarboxylic acid produced in step (b) or step (c);
wherein said article of clothing or textile is cleaned, destained, deodorized, sanitized, disinfected, or a combination thereof.

BRIEF DESCRIPTION OF THE BIOLOGICAL SEQUENCES

The following sequences comply with 37 C.F.R. §§1.821-1.825 ("Requirements for Patent Applications Containing Nucleotide Sequences and/or Amino Acid Sequence Disclosures—the Sequence Rules") and are consistent with World Intellectual Property Organization (WIPO) Standard ST.25 (1998) and the sequence listing requirements of the European Patent Convention (EPC) and the Patent Cooperation Treaty (PCT) Rules 5.2 and 49.5(a-bis), and Section 208 and Annex C of the Administrative Instructions. The symbols and format used for nucleotide and amino acid sequence data comply with the rules set forth in 37 C.F.R. §1.822.

SEQ ID NO:1 is the deduced amino acid sequence of a cephalosporin C deacetylase from *Bacillus subtilis* ATCC® 31954™.

SEQ ID NO:2 is the deduced amino acid sequence of a cephalosporin C deacetylase from *B. subtilis* ATCC® 6633™.

SEQ ID NO:3 is the deduced amino acid sequence of a cephalosporin C deacetylase from *B. licheniformis* ATCC® 14580™.

SEQ ID NO:4 is the deduced amino acid sequence of an acetyl xylan esterase from *B. pumilus* PS213.

SEQ ID NO:5 is the deduced amino acid sequence of an acetyl xylan esterase from *Clostridium thermocellum* ATCC® 27405™.

SEQ ID NO:6 is the deduced amino acid sequence of an acetyl xylan esterase from *Thermotoga neapolitana*.

SEQ ID NO:7 is the deduced amino acid sequence of an acetyl xylan esterase from *Thermotoga maritima* MSB8.

SEQ ID NO:8 is the deduced amino acid sequence of an acetyl xylan esterase from *Thermoanaerobacterium* sp. JW/SL YS485.

SEQ ID NO:9 is the deduced amino acid sequence of a cephalosporin C deacetylase from *Bacillus* sp. NRRL B-14911. It should be noted that the nucleic acid sequence encoding the cephalosporin C deacetylase from *Bacillus* sp. NRRL B-14911 as reported in GENBANK® Accession number ZP_01168674 appears to encode a 15 amino acid N-terminal addition that is likely incorrect based on sequence alignments with other cephalosporin C deacetylases and a comparison of the reported length (340 amino acids) versus the observed length of other CAH enzymes (typically 318-325 amino acids in length; see co-owed, co-filed, and copending U.S. patent application Ser. No. 12/572,059 entitled "ENZYMATIC PERACID PRODUCTION USING A COSOLVENT"; herein incorporated by reference). As such, the deduced amino acid sequence reported herein for the cephalosporin C deacetylase sequence from *Bacillus* sp. NRRL B-14911 does not include the N-terminal 15 amino acids as reported under GENBANK® Accession number ZP_01168674.

SEQ ID NO:10 is the deduced amino acid sequence of a cephalosporin C deacetylase from *Bacillus halodurans* C-125.

SEQ ID NO:11 is the deduced amino acid sequence of a cephalosporin C deacetylase from *Bacillus clausii* KSM-K16.

SEQ ID NO:12 is the deduced amino acid sequence of a *Bacillus subtilis* ATCC® 29233™ cephalosporin C deacetylase (CAH).

SEQ ID NO:13 is the deduced amino acid sequence of a *Thermoanearobacterium saccharolyticum* cephalosporin C deacetylase.

SEQ ID NO:14 is the deduced amino acid sequence of a *Thermotoga lettingae* acetyl xylan esterase.

SEQ ID NO:15 is the deduced amino acid sequence of a *Thermotoga petrophila* acetyl xylan esterase.

SEQ ID NO:16 is the deduced amino acid sequence of a first acetyl xylan esterase from *Thermotoga* sp. RQ2 described herein as "RQ2(a)".

SEQ ID NO:17 is the deduced amino acid sequence of a second acetyl xylan esterase from *Thermotoga* sp. RQ2 described herein as "RQ2(b)".

SEQ ID NO:18 is the amino acid sequence of the region encompassing amino acids residues 118 through 299 of SEQ ID NO:1.

SEQ ID NO:19 is the deduced amino acid sequence of a *Thermotoga neapolitana* acetyl xylan esterase variant from co-owned, co-filed, and copending U.S. patent application Ser. No. 12/572,094 (incorporated herein by reference in its entirety), where the Xaa residue at position 277 is Ala, Val, Ser, or Thr.

SEQ ID NO:20 is the deduced amino acid sequence of a *Thermotoga maritima* MSB8 acetyl xylan esterase variant from co-owned, co-filed, and copending U.S. patent application Ser. No. 12/572,094, where the Xaa residue at position 277 is Ala, Val, Ser, or Thr.

SEQ ID NO:21 is the deduced amino acid sequence of a *Thermotoga lettingae* acetyl xylan esterase variant from co-owned, co-filed, and copending U.S. patent application Ser. No. 12/572,094, where the Xaa residue at position 277 is Ala, Val, Ser, or Thr.

SEQ ID NO:22 is the deduced amino acid sequence of a *Thermotoga petrophila* acetyl xylan esterase variant from co-owned, co-filed, and copending U.S. patent application Ser. No. 12/572,094, where the Xaa residue at position 277 is Ala, Val, Ser, or Thr.

SEQ ID NO:23 is the deduced amino acid sequence of a *Thermotoga* sp. RQ2 acetyl xylan esterase variant derived from"RQ2(a)" from co-owned, co-filed, and copending U.S. patent application Ser. No. 12/572,094, where the Xaa residue at position 277 is Ala, Val, Ser, or Thr.

SEQ ID NO:24 is the deduced amino acid sequence of a *Thermotoga* sp. RQ2 acetyl xylan esterase variant derived from "RQ2(b)" from co-owned, co-filed, and copending U.S. patent application Ser. No. 12/572,094, where the Xaa residue at position 278 is Ala, Val, Ser, or Thr.

SEQ ID NO:25 is the deduced amino acid sequence of a *Thermoanaerobacterium* sp. JW/SL YS485 acetyl xylan esterase.

SEQ ID NO:26 is the coding region of a kanamycin resistance gene (kan) from *Streptomyces kanamyceticus*.

SEQ ID NO:27 is plasmid pKD13, which contains the kanamycin resistance gene.

SEQ ID NO:28 is a forward primer used to clone katG from plasmid pKD13.

SEQ ID NO:29 is a reverse primer used to clone katG from plasmid pKD13.

SEQ ID NO:30 is the PCR product of the katG amplification from plasmid pKD13 using the primers of SEQ ID NO:28 and SEQ ID NO:29.

SEQ ID NO:31 is the coding region of the catalase-peroxidase gene (katG).

SEQ ID NO:32 is the deduced amino acid sequence of katG.

SEQ ID NO:33 is plasmid pKD46, which contains the λ-Red recombinase genes.

SEQ ID NO:34 is a forward primer used to confirm disruption of katG.

SEQ ID NO:35 is a reverse primer used to confirm disruption of katG.

SEQ ID NO:36 is the temperature-sensitive plasmid pCP20, which contains the FLP recombinase.

SEQ ID NO:37 is a forward primer used to clone katE from plasmid pKD13.

SEQ ID NO:38 is a reverse primer used to clone katE from plasmid pKD13.

SEQ ID NO:39 is the PCR product of the katE amplification from plasmid pKD13 using the primers of SEQ ID NO:37 and SEQ ID NO:38.

SEQ ID NO:40 is the coding region of the catalase HPII gene (katE).

SEQ ID NO:41 is the deduced amino acid sequence of katE.

SEQ ID NO:42 is a forward primer used to confirm disruption of katE.

SEQ ID NO:43 is a reverse primer used to confirm disruption of katE.

SEQ ID NO:44 is a coding region of a gene encoding acetyl xylan esterase from *Thermotoga neapolitana* as reported in GENBANK® (accession #AE000512).

SEQ ID NO:45 is a forward primer used to amplify the acetyl xylan esterase gene from *Thermotoga neapolitana*.

SEQ ID NO:46 is a reverse primer used to amplify the acetyl xylan esterase gene from *Thermotoga neapolitana*.

SEQ ID NO:47 is the PCR product of the acetyl xylan esterase amplification using the primers of SEQ ID NO:45 and SEQ ID NO:46.

SEQ ID NO:48 is a gene encoding acetyl xylan esterase from *Thermotoga maritima* MSB8 as reported in GENBANK® (accession #NP_227893.1).

SEQ ID NO:49 is a forward primer used to amplify the acetyl xylan esterase gene from *Thermotoga maritima*.

SEQ ID NO:50 is a reverse primer used to amplify the acetyl xylan esterase gene from *Thermotoga maritima*.

SEQ ID NO:51 is the PCR product of the acetyl xylan esterase amplification using the primers of SEQ ID NO:49 and SEQ ID NO:50.

DETAILED DESCRIPTION OF THE INVENTION

Disclosed herein is a method for stabilization of the perhydrolase activity of a CE-7 esterase in a formulation with a carboxylic acid ester that employs the addition of a buffering agent, substantially undissolved, to the formulation of the CE-7 esterase and the carboxylic acid ester. Further, disinfectant formulations comprising the peracids produced by the processes described herein are provided.

In this disclosure, a number of terms and abbreviations are used. The following definitions apply unless specifically stated otherwise.

As used herein, the articles "a", "an", and "the" preceding an element or component of the invention are intended to be nonrestrictive regarding the number of instances (i.e., occurrences) of the element or component. Therefore "a", "an" and "the" should be read to include one or at least one, and the singular word form of the element or component also includes the plural unless the number is obviously meant to be singular.

As used herein, the term "comprising" means the presence of the stated features, integers, steps, or components as referred to in the claims, but that it does not preclude the presence or addition of one or more other features, integers, steps, components or groups thereof. The term "comprising" is intended to include embodiments encompassed by the terms "consisting essentially of" and "consisting of". Similarly, the term "consisting essentially of" is intended to include embodiments encompassed by the term "consisting of".

As used herein, the term "about" modifying the quantity of an ingredient or reactant employed refers to variation in the numerical quantity that can occur, for example, through typical measuring and liquid handling procedures used for making concentrates or use solutions in the real world; through inadvertent error in these procedures; through differences in the manufacture, source, or purity of the ingredients employed to make the compositions or carry out the methods; and the like. The term "about" also encompasses amounts that differ due to different equilibrium conditions for a composition resulting from a particular initial mixture. Whether or not modified by the term "about", the claims include equivalents to the quantities.

Where present, all ranges are inclusive and combinable. For example, when a range of "1 to 5" is recited, the recited range should be construed as including ranges "1 to 4", "1 to 3", "1-2", "1-2 & 4-5", "1-3 & 5", and the like.

As used herein, the terms "substrate", "suitable substrate", and "carboxylic acid ester substrate" interchangeably refer specifically to:

(a) one or more esters having the structure $[X]_m R_5$ wherein
X is an ester group of the formula $R_6C(O)O$;
$R_6$ is a C1 to C7 linear, branched or cyclic hydrocarbyl moiety, optionally substituted with a hydroxyl group or C1 to C4 alkoxy group, wherein $R_6$ optionally comprises one or more ether linkages where $R_6$ is C2 to C7;
$R_5$ is a C1 to C6 linear, branched, or cyclic hydrocarbyl moiety optionally substituted with a hydroxyl group, wherein each carbon atom in $R_5$ individually comprises no more than one hydroxyl group or no more than one ester group, and wherein $R_5$ optionally comprises one or more ether linkages;
m is 1 to the number of carbon atoms in $R_5$,
said one or more esters having a solubility in water of at least 5 ppm at 25° C.; or (b) one or more glycerides having the structure

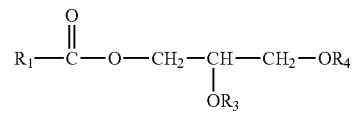

wherein $R_1$ is a C1 to C7 straight chain or branched chain alkyl optionally substituted with an hydroxyl or a C1 to C4 alkoxy group and $R_3$ and $R_4$ are individually H or $R_1C(O)$; or (c) one or more esters of the formula

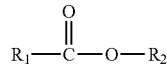

wherein $R_1$ is a C1 to C7 straight chain or branched chain alkyl optionally substituted with an hydroxyl or a C1 to C4 alkoxy group and $R_2$ is a C1 to C10 straight chain or branched chain alkyl, alkenyl, alkynyl, aryl, alkylaryl, alkylheteroaryl, heteroaryl, $(CH_2CH_2O)_n$, or $(CH_2CH(CH_3)-O)_nH$ and n is 1 to 10; or (d) one or more acetylated monosaccharides, acetylated disaccharides, or acetylated polysaccharides; or (e) any combination of (a) through (d).

Examples of said carboxylic acid ester substrate may include monoacetin; triacetin; monopropionin; dipropionin; tripropionin; monobutyrin; dibutyrin; tributyrin; glucose pentaacetate; xylose tetraacetate; acetylated xylan; acetylated xylan fragments; β-D-ribofuranose-1,2,3,5-tetraacetate; tri-O-acetyl-D-galactal; tri-O-acetyl-glucal; propylene glycol diacetate; ethylene glycol diacetate; monoesters or diesters of 1,2-ethanediol; 1,2-propanediol; 1,3-propanediol; 1,2-butanediol; 1,3-butanediol; 2,3-butanediol; 1,4-butanediol; 1,2-pentanediol; 2,5-pentanediol; 1,6-pentanediol, 1,2-hexanediol; 2,5-hexanediol; 1,6-hexanediol; or any combination thereof.

As used herein, the term "peracid" is synonymous with peroxyacid, peroxycarboxylic acid, peroxy acid, percarboxylic acid and peroxoic acid.

As used herein, the term "peracetic acid" is abbreviated as "PAA" and is synonymous with peroxyacetic acid, ethaneperoxoic acid and all other synonyms of CAS Registry Number 79-21-0.

As used herein, the term "monoacetin" is synonymous with glycerol monoacetate, glycerin monoacetate, and glyceryl monoacetate.

As used herein, the term "diacetin" is synonymous with glycerol diacetate; glycerin diacetate, glyceryl diacetate, and all other synonyms of CAS Registry Number 25395-31-7.

As used herein, the term "triacetin" is synonymous with glycerin triacetate; glycerol triacetate; glyceryl triacetate, 1,2,3-triacetoxypropane; 1,2,3-propanetriol triacetate and all other synonyms of CAS Registry Number 102-76-1.

As used herein, the term "monobutyrin" is synonymous with glycerol monobutyrate, glycerin monobutyrate, and glyceryl monobutyrate.

As used herein, the term "dibutyrin" is synonymous with glycerol dibutyrate and glyceryl dibutyrate.

As used herein, the term "tributyrin" is synonymous with glycerol tributyrate, 1,2,3-tributyrylglycerol, and all other synonyms of CAS Registry Number 60-01-5.

As used herein, the term "monopropionin" is synonymous with glycerol monopropionate, glycerin monopropionate, and glyceryl monopropionate.

As used herein, the term "dipropionin" is synonymous with glycerol dipropionate and glyceryl dipropionate.

As used herein, the term "tripropionin" is synonymous with glyceryl tripropionate, glycerol tripropionate, 1,2,3-tripropionylglycerol, and all other synonyms of CAS Registry Number 139-45-7.

As used herein, the term "ethyl acetate" is synonymous with acetic ether, acetoxyethane, ethyl ethanoate, acetic acid ethyl ester, ethanoic acid ethyl ester, ethyl acetic ester and all other synonyms of CAS Registry Number 141-78-6.

As used herein, the term "ethyl lactate" is synonymous with lactic acid ethyl ester and all other synonyms of CAS Registry Number 97-64-3.

As used herein, the terms "acetylated sugar" and "acetylated saccharide" refer to mono-, di- and polysaccharides comprising at least one acetyl group. Examples include, but are not limited to, glucose pentaacetate, xylose tetraacetate, acetylated xylan, acetylated xylan fragments, β-D-ribofuranose-1,2,3,5-tetraacetate, tri-O-acetyl-D-galactal, and tri-O-acetyl-glucal.

As used herein, the terms "hydrocarbyl", "hydrocarbyl group", and "hydrocarbyl moiety" is meant a straight chain, branched or cyclic arrangement of carbon atoms connected by single, double, or triple carbon to carbon bonds and/or by ether linkages, and substituted accordingly with hydrogen atoms. Such hydrocarbyl groups may be aliphatic and/or aromatic. Examples of hydrocarbyl groups include methyl, ethyl, propyl, isopropyl, butyl, isobutyl, t-butyl, cyclopropyl, cyclobutyl, pentyl, cyclopentyl, methylcyclopentyl, hexyl, cyclohexyl, benzyl, and phenyl. In a preferred embodiment, the hydrocarbyl moiety is a straight chain, branched or cyclic arrangement of carbon atoms connected by single carbon to carbon bonds and/or by ether linkages, and substituted accordingly with hydrogen atoms.

As used herein, the terms "monoesters" and "diesters" of 1,2-ethanediol; 1,2-propanediol; 1,3-propanediol; 1,2-butanediol; 1,3-butanediol; 2,3-butanediol; 1,4-butanediol; 1,2-pentanediol; 2,5-pentanediol; 1,6-pentanediol; 1,2-hexanediol; 2,5-hexanediol; 1,6-hexanediol; and mixtures thereof, refer to said compounds comprising at least one ester group of the formula RC(O)O, wherein R is a C1 to C7 linear hydrocarbyl moiety. In one embodiment, the carboxylic acid ester substrate is selected from the group consisting of propylene glycol diacetate (PGDA), ethylene glycol diacetate (EDGA), and mixtures thereof.

As used herein, the term "propylene glycol diacetate" is synonymous with 1,2-diacetoxypropane, propylene diacetate, 1,2-propanediol diacetate, and all other synonyms of CAS Registry Number 623-84-7.

As used herein, the term "ethylene glycol diacetate" is synonymous with 1,2-diacetoxyethane, ethylene diacetate, glycol diacetate, and all other synonyms of CAS Registry Number 111-55-7.

As used herein, the terms "suitable enzymatic reaction mixture", "components suitable for in situ generation of a peracid", "suitable reaction components", and "suitable aqueous reaction mixture" refer to the materials and water in which the reactants and enzyme catalyst come into contact. The components of the suitable aqueous reaction mixture are provided herein and those skilled in the art appreciate the range of component variations suitable for this process. In one embodiment, the suitable enzymatic reaction mixture produces peracid in situ upon combining the reaction components. As such, the reaction components may be provided as a multicomponent system wherein one or more of the reaction components remains separated until use. In another embodiment, the reaction components are first combined to form an aqueous solution of peracid which is subsequently contacted with the surface to be disinfected and/or bleached. The design of systems and means for separating and combining multiple active components are known in the art and generally will depend upon the physical form of the individual reaction components. For example, multiple active fluids (liquid-liquid) systems typically use multi-chamber dispenser bottles or two-phase systems (e.g., U.S. Patent Application Publication No. 2005/0139608; U.S. Pat. Nos. 5,398,846; 5,624,634; 6,391,840; E.P. Patent 0807156B1; U.S. Patent Application Publication No. 2005/0008526; and PCT Publication No. WO 00/61713) such as found in some bleaching applications wherein the desired bleaching agent is produced upon mixing the reactive fluids. Other forms of multi-component systems used to generate peracid may include, but are not limited to, those designed for one or more solid components or combinations of solid-liquid components, such as powders (e.g., U.S. Pat. No. 5,116,575), multi-layered tablets (e.g., U.S. Pat. No. 6,210,639), water dissolvable packets having multiple compartments (e.g., U.S. Pat. No. 6,995,125) and solid agglomerates that react upon the addition of water (e.g., U.S. Pat. No. 6,319,888). In one embodiment, a multicomponent formulation is provided as two individual components whereby an aqueous solution comprising a peroxycarboxylic acid is generated upon combining the two components. In another embodiment, a multicomponent formulation is provided comprising:

a) a first component comprising:
  i) an enzyme powder as disclosed herein; and
  ii) a carboxylic acid ester, said first component optionally comprising a further ingredient selected from the group consisting of an inorganic or organic buffer, a corrosion inhibitor, a wetting agent, and combinations thereof; and b) a second component comprising a source of peroxygen and water, said second component optionally comprising a hydrogen peroxide stabilizer.

In another embodiment, the carboxylic acid ester in the first component is selected from the group consisting of monoacetin, diacetin, triacetin, and combinations thereof. In another embodiment, the carboxylic acid ester in the first component is an acetylated saccharide. In another embodiment, the enzyme catalyst in the first component is a particulate solid. In another embodiment, the first reaction component is a solid tablet or powder.

As used herein, the term "perhydrolysis" is defined as the reaction of a selected substrate with peroxide to form a peracid. Typically, inorganic peroxide is reacted with the selected substrate in the presence of a catalyst to produce the peracid. As used herein, the term "chemical perhydrolysis" includes perhydrolysis reactions in which a substrate (a peracid precursor) is combined with a source of hydrogen peroxide wherein peracid is formed in the absence of an enzyme catalyst.

As used herein, the term "perhydrolase activity" refers to the catalyst activity per unit mass (for example, milligram) of protein, dry cell weight, or immobilized catalyst weight.

As used herein, "one unit of enzyme activity" or "one unit of activity" or "U" is defined as the amount of perhydrolase activity required for the production of 1 μmol of peracid product per minute at a specified temperature.

As used herein, the terms "enzyme catalyst" and "perhydrolase catalyst" refer to a catalyst comprising an enzyme having perhydrolysis activity and may be in the form of a whole microbial cell, permeabilized microbial cell(s), one or more cell components of a microbial cell extract, partially purified enzyme, or purified enzyme. The enzyme catalyst may also be chemically modified (e.g., by pegylation or by reaction with cross-linking reagents). The perhydrolase catalyst may also be immobilized on a soluble or insoluble support using methods well-known to those skilled in the art; see for example, *Immobilization of Enzymes and Cells*; Gordon F. Bickerstaff, Editor; Humana Press, Totowa, N.J., USA; 1997. As described herein, all of the present enzymes having perhydrolysis activity are structurally members of the carbohydrate family esterase family 7 (CE-7 family) of enzymes (see Coutinho, P. M., Henrissat, B. "Carbohydrate-active enzymes: an integrated database approach" in *Recent Advances in Carbohydrate Bioengineering*, H. J. Gilbert, G. Davies, B. Henrissat and B. Svensson eds., (1999) The Royal Society of Chemistry, Cambridge, pp. 3-12.). The CE-7 family of enzymes has been demonstrated to be particularly effective for producing peracids from a variety of carboxylic acid ester substrates when combined with a source of peroxygen (See PCT publication No. WO2007/070609 and U.S. Patent Application Publication Nos. 2008/0176299, 2008/176783, and 2009/0005590 to DiCosimo et al.; each herein incorporated by reference in their entireties).

Members of the CE-7 family include cephalosporin C deacetylases (CAHs; E.C. 3.1.1.41) and acetyl xylan esterases (AXEs; E.C. 3.1.1.72). Members of the CE-7 esterase family share a conserved signature motif (Vincent et al., *J. Mol. Biol.*, 330:593-606 (2003)). Perhydrolases comprising the CE-7 signature motif and/or a substantially similar structure are suitable for use in the present invention. Means to identify substantially similar biological molecules are well known in the art (e.g., sequence alignment protocols, nucleic acid hybridizations, and/or the presence of a conserved signature motif). In one aspect, the present perhydrolases include enzymes comprising the CE-7 signature motif and at least 30%, preferably at least 33%, more preferably at least 40%, even more preferably at least 42%, even more preferably at least 50%, even more preferably at least 60%, even more preferably at least 70%, even more preferably at least 80%, even more preferably at least 90%, and most preferably at least 90%, 91%, 92%, 93%, 94%, 95%, 96%, 97%, 98%, or 99% amino acid identity to the sequences provided herein. In a further aspect, the present perhydrolases include enzymes comprising the CE-7 signature motif and at least 30%, preferably at least 33%, more preferably at least 40%, even more preferably at least 42%, even more preferably at least 50%, even more preferably at least 60%, even more preferably at least 70%, even more preferably at least 80%, even more preferably at least 90%, and most preferably at least 90%, 91%, 92%, 93%, 94%, 95%, 96%, 97%, 98%, or 99% amino acid identity to SEQ ID NO: 1.

As used herein, the term "enzyme powder" refers to the spray-dried product of an aqueous formulation comprising (1) at least one enzyme structurally classified as a CE-7 carbohydrate esterase that has perhydrolysis activity, (2) at least one oligosaccharide excipient, and optionally at least one surfactant. In some embodiments, the at least one oligosaccharide excipient has a number average molecular weight of at least about 1250 and a weight average molecular weight of at least about 9000.

As used herein, the terms "cephalosporin C deacetylase" and "cephalosporin C acetyl hydrolase" refer to an enzyme (E.C. 3.1.1.41) that catalyzes the deacetylation of cephalosporins such as cephalosporin C and 7-aminocephalosporanic acid (Mitsushima et al., (1995) *Appl. Env. Microbiol.* 61(6):2224-2229). Several cephalosporin C deacetylases are provided herein having significant perhydrolysis activity.

As used herein, "acetyl xylan esterases" refers to an enzyme (E.C. 3.1.1.72; AXEs) that catalyzes the deacetylation of acetylated xylans and other acetylated saccharides. As illustrated herein, several enzymes classified as acetyl xylan esterases are provided having significant perhydrolysis activity.

As used herein, the term "*Bacillus subtilis* ATCC® 31954™" refers to a bacterial cell deposited to the American Type Culture Collection (ATCC®) having international depository accession number ATCC® 31954™. *Bacillus subtilis* ATCC® 31954™ has been reported to have an ester hydrolase ("diacetinase") activity capable of hydrolyzing glycerol esters having 2 to 8 carbon acyl groups, especially diacetin (U.S. Pat. No. 4,444,886; herein incorporated by reference in its entirety). As described herein, an enzyme having significant perhydrolase activity has been isolated from *B. subtilis* ATCC® 31954™ and is provided as SEQ ID NO:1. The amino acid sequence of the isolated enzyme has 100% amino acid identity to the cephalosporin C deacetylase provided by GENBANK® Accession No. BAA01729.1 (Mitsushima et al., supra).

As used herein, the term "*Bacillus subtilis* ATCC® 29233™" refers to a strain of *Bacillus subtilis* deposited to the American Type Culture Collection (ATCC®) having international depository accession number ATCC® 29233™. As described herein, an enzyme having significant perhydrolase activity has been isolated and sequenced from *B. subtilis* ATCC® 29233™ and is provided as SEQ ID NO:12.

As used herein, the term "*Clostridium thermocellum* ATCC® 27405™" refers to a strain of *Clostridium thermocellum* deposited to the American Type Culture Collection (ATCC®) having international depository accession number ATCC® 27405™. The amino acid sequence of the enzyme having perhydrolase activity from *C. thermocellum* ATCC® 27405™ is provided as SEQ ID NO:5.

As used herein, the term "*Bacillus subtilis* ATCC® 6633™" refers to a bacterial cell deposited to the American Type Culture Collection (ATCC®) having international depository accession number ATCC® 6633™. *Bacillus subtilis* ATCC® 6633™ has been reported to have cephalosporin acetylhydrolase activity (U.S. Pat. No. 6,465,233). The amino acid sequence of the enzyme having perhydrolase activity from *B. subtilis* ATCC® 6633™ is provided as SEQ ID NO:2.

As used herein, the term "*Bacillus licheniformis* ATCC® 14580™" refers to a bacterial cell deposited to the American Type Culture Collection (ATCC®) having international depository accession number ATCC® 14580™. *Bacillus licheniformis* ATCC® 14580™ has been reported to have cephalosporin acetylhydrolase activity. The amino acid sequence of the enzyme having perhydrolase activity from *B. licheniformis* ATCC® 14580™ is provided as SEQ ID NO:3.

As used herein, the term "*Bacillus pumilus* PS213" refers to a bacterial cell reported to have acetyl xylan esterase activity (GENBANK® AJ249957). The amino acid sequence of the enzyme having perhydrolase activity from *Bacillus pumilus* PS213 is provided as SEQ ID NO:4.

As used herein, the term "*Thermotoga neapolitana*" refers to a strain of *Thermotoga neapolitana* reported to have acetyl xylan esterase activity (GENBANK® AAB70869). The amino acid sequence of the enzyme having perhydrolase activity from *Thermotoga neapolitana* is provided as SEQ ID NO: 6.

As used herein, the term "*Thermotoga maritima* MSB8" refers to a bacterial cell reported to have acetyl xylan esterase activity (GENBANK® NP_227893.1). The amino acid sequence of the enzyme having perhydrolase activity from *Thermotoga maritima* MSB8 is provided as SEQ ID NO: 7.

As used herein, the term "*Bacillus clausii* KSM-K16" refers to a bacterial cell reported to have cephalosporin-C deacetylase activity (GENBANK® YP_175265). The amino acid sequence of the enzyme having perhydrolase activity from *Bacillus clausii* KSM-K16 is provided as SEQ ID NO: 11.

As used herein, the term "*Thermoanearobacterium saccharolyticum*" refers to a bacterial strain reported to have acetyl xylan esterase activity (GENBANK® S41858). The amino acid sequence of the enzyme having perhydrolase activity from *Thermoanearobacterium saccharolyticum* is provided as SEQ ID NO: 13.

As used herein, the term "*Thermotoga lettingae*" refers to a bacterial cell reported to have acetyl xylan esterase activity (GENBANK®CP000812). The deduced amino acid sequence of the enzyme having perhydrolase activity from *Thermotoga lettingae* is provided as SEQ ID NO: 14.

As used herein, the term "*Thermotoga petrophila*" refers to a bacterial cell reported to have acetyl xylan esterase activity (GENBANK® CP000702). The deduced amino acid sequence of the enzyme having perhydrolase activity from *Thermotoga lettingae* is provided as SEQ ID NO: 15.

As used herein, the term "*Thermotoga sp. RQ2*" refers to a bacterial cell reported to have acetyl xylan esterase activity (GENBANK® CP000969). Two different acetyl xylan esterases have been identified from *Thermotoga sp.* RQ2 and are referred to herein as "RQ2(a)" (the deduced amino acid sequence provided as SEQ ID NO: 16) and "RQ2(b)" (the deduced amino acid sequence provided as SEQ ID NO: 17).

As used herein, an "isolated nucleic acid molecule" and "isolated nucleic acid fragment" will be used interchangeably and refer to a polymer of RNA or DNA that is single- or double-stranded, optionally containing synthetic, non-natural or altered nucleotide bases. An isolated nucleic acid molecule in the form of a polymer of DNA may be comprised of one or more segments of cDNA, genomic DNA or synthetic DNA.

The term "amino acid" refers to the basic chemical structural unit of a protein or polypeptide. The following abbreviations are used herein to identify specific amino acids:

| Amino Acid | Three-Letter Abbreviation | One-Letter Abbreviation |
|---|---|---|
| Alanine | Ala | A |
| Arginine | Arg | R |
| Asparagine | Asn | N |
| Aspartic acid | Asp | D |
| Cysteine | Cys | C |
| Glutamine | Gln | Q |
| Glutamic acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |
| Any amino acid or as defined herein | Xaa | X |

As used herein, "substantially similar" refers to nucleic acid molecules wherein changes in one or more nucleotide bases results in the addition, substitution, or deletion of one or more amino acids, but does not affect the functional properties (i.e., perhydrolytic activity) of the protein encoded by the DNA sequence. As used herein, "substantially similar" also refers to an enzyme having an amino acid sequence that is at least 30%, preferably at least 33%, more preferably at least 40%, more preferably at least 50%, even more preferably at least 60%, even more preferably at least 70%, even more preferably at least 80%, yet even more preferably at least 90%, 91%, 92%, 93%, 94%, 95%, 96%, 97%, 98%, or 99% identical to the sequences reported herein wherein the resulting enzyme retains the present functional properties (i.e., perhydrolytic activity). "Substantially similar" may also refer to an enzyme having perhydrolytic activity encoded by nucleic acid molecules that hybridize under stringent conditions to the nucleic acid molecules reported herein. It is therefore understood that the invention encompasses more than the specific exemplary sequences.

For example, it is well known in the art that alterations in a gene which result in the production of a chemically equivalent amino acid at a given site, but do not affect the functional properties of the encoded protein are common. For the purposes of the present invention substitutions are defined as exchanges within one of the following five groups:
1. Small aliphatic, nonpolar or slightly polar residues: Ala, Ser, Thr (Pro, Gly);
2. Polar, negatively charged residues and their amides: Asp, Asn, Glu, Gln;
3. Polar, positively charged residues: His, Arg, Lys;
4. Large aliphatic, nonpolar residues: Met, Leu, Ile, Val (Cys); and
5. Large aromatic residues: Phe, Tyr, and Trp.

Thus, a codon for the amino acid alanine, a hydrophobic amino acid, may be substituted by a codon encoding another less hydrophobic residue (such as glycine) or a more hydrophobic residue (such as valine, leucine, or isoleucine). Similarly, changes which result in substitution of one negatively charged residue for another (such as aspartic acid for glutamic acid) or one positively charged residue for another (such as lysine for arginine) can also be expected to produce a functionally equivalent product. In many cases, nucleotide changes which result in alteration of the N-terminal and C-terminal portions of the protein molecule would also not be expected to alter the activity of the protein.

Each of the proposed modifications is well within the routine skill in the art, as is determination of retention of biological activity of the encoded products. Moreover, the skilled artisan recognizes that substantially similar sequences are encompassed by the present invention. In one embodiment, substantially similar sequences are defined by their ability to hybridize, under stringent conditions (0.1×SSC, 0.1% SDS, 65° C. and washed with 2×SSC, 0.1% SDS followed by 0.1×SSC, 0.1% SDS, 65° C.) with the sequences exemplified herein.

As used herein, a nucleic acid molecule is "hybridizable" to another nucleic acid molecule, such as a cDNA, genomic DNA, or RNA, when a single strand of the first molecule can anneal to the other molecule under appropriate conditions of temperature and solution ionic strength. Hybridization and washing conditions are well known and exemplified in Sambrook, J. and Russell, D., T. *Molecular Cloning: A Laboratory Manual*, Third Edition, Cold Spring Harbor Laboratory Press, Cold Spring Harbor (2001). The conditions of temperature and ionic strength determine the "stringency" of the hybridization. Stringency conditions can be adjusted to screen for moderately similar molecules, such as homologous sequences from distantly related organisms, to highly similar molecules, such as genes that duplicate functional enzymes from closely related organisms. Post-hybridization washes typically determine stringency conditions. One set of preferred conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of conditions uses higher temperatures in which the washes are identical to those above except for the temperature of the final two 30 min washes in 0.2×SSC, 0.5% SDS was increased to 60° C. Another preferred set of stringent hybridization conditions is 0.1×SSC, 0.1% SDS, 65° C. and washed with 2×SSC, 0.1% SDS followed by a final wash of 0.1×SSC, 0.1% SDS, 65° C. with the sequences exemplified herein. In a further embodiment, the present compositions and methods employ an enzyme having perhydrolase activity encoded by isolated nucleic acid molecule that hybridizes under stringent conditions to a nucleic acid molecule encoding a polypeptide having perhydrolysis activity, said polypeptide having an amino acid sequence selected from the group consisting of SEQ ID NO: 1, SEQ ID NO: 2, SEQ ID NO: 3; SEQ ID NO: 4; SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13; SEQ ID NO: 14; SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, and SEQ ID NO: 25.

Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of Tm for hybrids of nucleic acids having those sequences. The relative stability (corresponding to higher Tm) of nucleic acid hybridizations decreases in the following order: RNA:RNA, DNA:RNA, DNA:DNA. For hybrids of greater than 100 nucleotides in length, equations for calculating Tm have been derived (Sambrook and Russell, supra). For hybridizations with shorter nucleic acids, i.e., oligonucleotides, the position of mismatches becomes more important, and the length of the oligonucleotide determines its specificity (Sambrook and Russell, supra). In one aspect, the length for a hybridizable nucleic acid is at least about 10 nucleotides. Preferably, a minimum length for a hybridizable nucleic acid is at least about 15 nucleotides in length, more preferably at least about 20 nucleotides in length, even more preferably at least 30 nucleotides in length, even more preferably at least 300 nucleotides in length, and most preferably at least 800 nucleotides in length. Furthermore, the skilled artisan will recognize that the temperature and wash solution salt concentration may be adjusted as necessary according to factors such as length of the probe.

As used herein, the term "percent identity" is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to, methods described in: *Computational Molecular Biology* (Lesk, A. M., ed.) Oxford University Press, NY (1988); *Biocomputing: Informatics and Genome Projects* (Smith, D. W., ed.) Academic Press, NY (1993); *Computer Analysis of Sequence Data, Part I* (Griffin, A. M., and Griffin, H. G., eds.) Humana Press, NJ (1994); *Sequence Analysis in Molecular Biology* (von Heinje, G., ed.) Academic Press (1987); and *Sequence Analysis Primer* (Gribskov, M. and Devereux, J., eds.) Stockton Press, NY (1991). Methods to determine identity and similarity are codified in publicly available computer programs. Sequence alignments and percent identity calculations may be performed using the Megalign program of the LASERGENE bioinformatics computing suite (DNASTAR Inc., Madison, Wis.), the AlignX program of Vector NTI v. 7.0 (Informax, Inc., Bethesda, Md.), or the EMBOSS Open Software Suite (EMBL-EBI; Rice et al., *Trends in Genetics* 16, (6):276-277 (2000)). Multiple alignment of the sequences can be performed using the Clustal method (e.g., CLUSTALW; for example version 1.83) of alignment (Higgins and Sharp, *CABIOS*, 5:151-153 (1989); Higgins et al., *Nucleic Acids Res.* 22:4673-4680 (1994); and Chenna et al., *Nucleic Acids Res* 31 (13):3497-500 (2003)), available from the European Molecular Biology Laboratory via the European Bioinformatics Institute) with the default parameters. Suitable parameters for CLUSTALW protein alignments include GAP Existence penalty=15, GAP extension=0.2, matrix=Gonnet (e.g. Gonnet250), protein ENDGAP=−1, Protein GAPDIST=4, and KTUPLE=1. In one embodiment, a fast or slow alignment is used with the default settings where a slow alignment is preferred. Alternatively, the parameters using the CLUSTALW method (version 1.83) may be modified to also use KTUPLE=1, GAP PENALTY=10, GAP extension=1, matrix=BLOSUM (e.g. BLOSUM64), WINDOW=5, and TOP DIAGONALS SAVED=5.

In one aspect, suitable isolated nucleic acid molecules encode a polypeptide having an amino acid sequence that is at least about 30%, preferably at least 33%, preferably at least 40%, preferably at least 50%, preferably at least 60%, more preferably at least 70%, more preferably at least 80%, even more preferably at least 85%, even more preferably at least 90%, 91%, 92%, 93%, 94%, 95%, 96%, 97%, 98%, or 99% identical to the amino acid sequences reported herein. Suitable nucleic acid molecules not only have the above homologies, but also typically encode a polypeptide having about 300 to about 340 amino acids, more preferably about 310 to about 330 amino acids, and most preferably about 318 amino acids.

As used herein, the terms "signature motif", "CE-7 signature motif", and "diagnostic motif" refer to conserved structures shared among a family of enzymes having a defined activity. The signature motif can be used to define and/or identify the family of structurally related enzymes having similar enzymatic activity for a defined family of substrates. The signature motif can be a single contiguous amino acid sequence or a collection of discontiguous, conserved motifs that together form the signature motif. Typically, the conserved motif(s) is represented by an amino acid sequence. As described herein, the present enzymes having perhydrolysis activity ("perhydrolases") belong to the family of CE-7 carbohydrate esterases (DiCosimo et al., supra). As used herein, the phrase "enzyme is structurally classified as a CE-7 enzyme" or "CE-7 perhydrolase" will be used to refer to enzymes having perhydrolysis activity which are structurally classified as a CE-7 carbohydrate esterase. This family of enzymes can be defined by the presence of a signature motif (Vincent et al., supra). As defined herein, the signature motif for CE-7 esterases comprises three conserved motifs (residue position numbering relative to reference sequence SEQ ID NO:1):

a) Arg118-Gly119-Gln120;

b) Gly179-Xaa180-Ser181-Gln182-Gly183; and c) His298-Glu299.

Typically, the Xaa at amino acid residue position 180 is glycine, alanine, proline, tryptophan, or threonine. Two of the three amino acid residues belonging to the catalytic triad are in bold. In one embodiment, the Xaa at amino acid residue position 180 is selected from the group consisting of glycine, alanine, proline, tryptophan, and threonine.

Further analysis of the conserved motifs within the CE-7 carbohydrate esterase family indicates the presence of an additional conserved motif (LXD at amino acid positions 267-269 of SEQ ID NO:1) that may be used to further define a perhydrolase belonging to the CE-7 carbohydrate esterase family. In a further embodiment, the signature motif defined above includes a fourth conserved motif defined as:

Leu267-Xaa268-Asp269.

The Xaa at amino acid residue position 268 is typically isoleucine, valine, or methionine. The fourth motif includes the aspartic acid residue (bold) belonging to the catalytic triad (Ser181-Asp269-His298).

A number of well-known global alignment algorithms may be used to align two or more amino acid sequences representing enzymes having perhydrolase activity to determine if the enzyme is comprised of the present signature motif. The aligned sequence(s) are compared to the reference sequence (SEQ ID NO:1) to determine the existence of the signature motif. In one embodiment, a CLUSTAL alignment (such as CLUSTALW) using a reference amino acid sequence (as used herein the perhydrolase sequence (SEQ ID NO:1) from the *Bacillus subtilis* ATCC® 31954™) is used to identify perhydrolases belonging to the CE-7 esterase family. The relative numbering of the conserved amino acid residues is based on the residue numbering of the reference amino acid sequence to account for small insertions or deletions (for example, five amino acids or less) within the aligned sequence.

Examples of other suitable algorithms that may be used to identify sequences comprising the present signature motif (when compared to the reference sequence) include, but are not limited to, Needleman and Wunsch (*J. Mol. Biol.* 48, 443-453 (1970); a global alignment tool) and Smith-Waterman (*J. Mol. Biol.* 147:195-197 (1981); a local alignment tool). In one embodiment, a Smith-Waterman alignment is implemented using default parameters. An example of suitable default parameters include the use of a BLOSUM62 scoring matrix with GAP open penalty=10 and a GAP extension penalty=0.5.

A comparison of the overall percent identity among perhydrolases exemplified herein indicates that enzymes having as little as 33% identity to SEQ ID NO:1 (while retaining the signature motif) exhibit significant perhydrolase activity and are structurally classified as CE-7 carbohydrate esterases. In one embodiment, suitable perhydrolases include enzymes comprising the CE-7 signature motif and at least 30%, preferably at least 33%, more preferably at least 40%, even more preferably at least 42%, even more preferably at least 50%, even more preferably at least 60%, even more preferably at least 70%, even more preferably at least 80%, even more preferably at least 90%, and most preferably at least 90%, 91%, 92%, 93%, 94%, 95%, 96%, 97%, 98%, or 99% amino acid identity to SEQ ID NO: 1.

Alternatively, a contiguous amino acid sequence comprising the region encompassing the conserved motifs may also be used to identify CE-7 family members.

As used herein, "codon degeneracy" refers to the nature of the genetic code permitting variation of the nucleotide sequence without affecting the amino acid sequence of an encoded polypeptide. Accordingly, the present invention relates to any nucleic acid molecule that encodes all or a substantial portion of the amino acid sequences encoding the present microbial polypeptide. The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

As used herein, the term "codon optimized", as it refers to genes or coding regions of nucleic acid molecules for transformation of various hosts, refers to the alteration of codons in the gene or coding regions of the nucleic acid molecules to reflect the typical codon usage of the host organism without altering the polypeptide for which the DNA codes.

As used herein, "synthetic genes" can be assembled from oligonucleotide building blocks that are chemically synthesized using procedures known to those skilled in the art. These building blocks are ligated and annealed to form gene segments that are then enzymatically assembled to construct the entire gene. "Chemically synthesized", as pertaining to a DNA sequence, means that the component nucleotides were assembled in vitro. Manual chemical synthesis of DNA may be accomplished using well-established procedures, or automated chemical synthesis can be performed using one of a number of commercially available machines. Accordingly, the genes can be tailored for optimal gene expression based on optimization of nucleotide sequences to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

As used herein, "gene" refers to a nucleic acid molecule that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different from that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

As used herein, "coding sequence" refers to a DNA sequence that codes for a specific amino acid sequence. "Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, RNA processing site, effector binding site and stem-loop structure.

As used herein, "promoter" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene at different stages of development, or in response to different environmental or physiological conditions. Promoters that cause a gene to be expressed at most times are commonly referred to as "constitutive promoters". It is further recognized that since in most cases the exact boundaries of regulatory sequences have not been completely defined, DNA fragments of different lengths may have identical promoter activity.

As used herein, the "3' non-coding sequences" refer to DNA sequences located downstream of a coding sequence and include polyadenylation recognition sequences (normally limited to eukaryotes) and other sequences encoding regulatory signals capable of affecting mRNA processing or gene expression. The polyadenylation signal is usually characterized by affecting the addition of polyadenylic acid tracts (normally limited to eukaryotes) to the 3' end of the mRNA precursor.

As used herein, the term "operably linked" refers to the association of nucleic acid sequences on a single nucleic acid molecule so that the function of one is affected by the other. For example, a promoter is operably linked with a coding sequence when it is capable of affecting the expression of that coding sequence, i.e., that the coding sequence is under the transcriptional control of the promoter. Coding sequences can be operably linked to regulatory sequences in sense or antisense orientation.

As used herein, the term "expression" refers to the transcription and stable accumulation of sense (mRNA) or antisense RNA derived from the nucleic acid molecule of the invention. Expression may also refer to translation of mRNA into a polypeptide.

As used herein, "transformation" refers to the transfer of a nucleic acid molecule into the genome of a host organism, resulting in genetically stable inheritance. In the present invention, the host cell's genome includes chromosomal and extrachromosomal (e.g. plasmid) genes. Host organisms containing the transformed nucleic acid molecules are referred to as "transgenic" or "recombinant" or "transformed" organisms.

As used herein, the terms "plasmid", "vector" and "cassette" refer to an extrachromosomal element often carrying genes which are not part of the central metabolism of the cell, and usually in the form of circular double-stranded stranded DNA molecules. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. "Transformation cassette" refers to a specific vector containing a foreign gene and having elements in addition to the foreign gene that facilitate transformation of a particular host cell. "Expression cassette" refers to a specific vector containing a foreign gene and having elements in addition to the foreign gene that allow for enhanced expression of that gene in a foreign host.

As used herein, the term "sequence analysis software" refers to any computer algorithm or software program that is useful for the analysis of nucleotide or amino acid sequences. "Sequence analysis software" may be commercially available or independently developed. Typical sequence analysis software will include, but is not limited to, the GCG suite of programs (Wisconsin Package Version 9.0, Genetics Computer Group (GCG), Madison, Wis.), BLASTP, BLASTN, BLASTX (Altschul et al., *J. Mol. Biol.* 215:403-410 (1990), and DNASTAR (DNASTAR, Inc. 1228 S. Park St. Madison, Wis. 53715 USA), CLUSTALW (for example, version 1.83; Thompson et al., *Nucleic Acids Research,* 22(22):4673-4680 (1994), and the FASTA program incorporating the Smith-Waterman algorithm (W. R. Pearson, *Comput. Methods Genome Res.*, [Proc. Int. Symp.] (1994), Meeting Date 1992, 111-20. Editor(s): Suhai, Sandor. Publisher: Plenum, New York, N.Y.), Vector NTI (Informax, Bethesda, Md.) and Sequencher v. 4.05. Within the context of this application it will be understood that where sequence analysis software is used for analysis, that the results of the analysis will be based on the "default values" of the program referenced, unless otherwise specified. As used herein "default values" will mean any set of values or parameters set by the software manufacturer that originally load with the software when first initialized.

As used herein, the term "biological contaminants" refers to one or more unwanted and/or pathogenic biological entities including, but not limited to, microorganisms, spores, viruses, prions, and mixtures thereof. The process produces an efficacious concentration of at least one percarboxylic acid useful to reduce and/or eliminate the presence of the viable biological contaminants. In a preferred embodiment, the biological contaminant is a viable pathogenic microorganism.

As used herein, the term "disinfect" refers to the process of destruction of or prevention of the growth of biological contaminants. As used herein, the term "disinfectant" refers to an agent that disinfects by destroying, neutralizing, or inhibiting the growth of biological contaminants. Typically, disinfectants are used to treat inanimate objects or surfaces. As used herein, the term "disinfection" refers to the act or process of disinfecting. As used herein, the term "antiseptic" refers to a chemical agent that inhibits the growth of disease-carrying microorganisms. In one aspect, the biological contaminants are pathogenic microorganisms.

As used herein, the term "sanitary" means of or relating to the restoration or preservation of health, typically by removing, preventing or controlling an agent that may be injurious to health. As used herein, the term "sanitize" means to make sanitary. As used herein, the term "sanitizer" refers to a sanitizing agent. As used herein the term "sanitization" refers to the act or process of sanitizing.

As used herein, the term "virucide" refers to an agent that inhibits or destroys viruses, and is synonymous with "viricide". An agent that exhibits the ability to inhibit or destroy viruses is described as having "virucidal" activity. Peracids can have virucidal activity. Typical alternative virucides known in the art which may be suitable for use with the present invention include, for example, alcohols, ethers, chloroform, formaldehyde, phenols, beta propiolactone, iodine, chlorine, mercury salts, hydroxylamine, ethylene oxide, ethylene glycol, quaternary ammonium compounds, enzymes, and detergents.

As used herein, the term "biocide" refers to a chemical agent, typically broad spectrum, which inactivates or destroys microorganisms. A chemical agent that exhibits the ability to inactivate or destroy microorganisms is described as having "biocidal" activity. Peracids can have biocidal activity. Typical alternative biocides known in the art, which may be suitable for use in the present invention include, for example, chlorine, chlorine dioxide, chloroisocyanurates, hypochlorites, ozone, acrolein, amines, chlorinated phenolics, copper salts, organo-sulphur compounds, and quaternary ammonium salts.

As used herein, the phrase "minimum biocidal concentration" refers to the minimum concentration of a biocidal agent that, for a specific contact time, will produce a desired lethal, irreversible reduction in the viable population of the targeted microorganisms. The effectiveness can be measured by the $\log_{10}$ reduction in viable microorganisms after treatment. In one aspect, the targeted reduction in viable microorganisms after treatment is at least a 3-log reduction, more preferably at least a 4-log reduction, and most preferably at least a 5-log reduction. In another aspect, the minimum biocidal concentration is at least a 6-log reduction in viable microbial cells.

As used herein, the terms "peroxygen source" and "source of peroxygen" refer to compounds capable of providing hydrogen peroxide at a concentration of about 1 mM or more when in an aqueous solution including, but not limited to, hydrogen peroxide, hydrogen peroxide adducts (e.g., urea-hydrogen peroxide adduct (carbamide peroxide)), perborates, and percarbonates. As described herein, the concentration of the hydrogen peroxide provided by the peroxygen compound in the aqueous reaction formulation is initially at least 1 mM or more upon combining the reaction components. In one embodiment, the hydrogen peroxide concentration in the aqueous reaction formulation is at least 10 mM. In another embodiment, the hydrogen peroxide concentration in the aqueous reaction formulation is at least 100 mM. In another embodiment, the hydrogen peroxide concentration in the aqueous reaction formulation is at least 200 mM. In another embodiment, the hydrogen peroxide concentration in the aqueous reaction formulation is 500 mM or more. In yet another embodiment, the hydrogen peroxide concentration in the aqueous reaction formulation is 1000 mM or more. The molar ratio of the hydrogen peroxide to enzyme substrate, e.g. triglyceride, ($H_2O_2$:substrate) in the aqueous reaction formulation may be from about 0.002 to 20, preferably about 0.1 to 10, and most preferably about 0.5 to 5.

By "oligosaccharide" is meant compounds containing between 2 and at least 24 monosaccharide units linked by glycosidic linkages. The term "monosaccharide" refers to a compound of empirical formula $(CH_2O)_n$, where $n \geq 13$, the carbon skeleton is unbranched, each carbon atom except one contains a hydroxyl group, and the remaining carbon atom is an aldehyde or ketone at carbon atom 2. The term "monosaccharide" also refers to intracellular cyclic hemiacetal or hemiketal forms.

As used herein, the term "excipient" refers to an inactive substance used to stabilize the active ingredient in a formulation, such as the storage stability of the active ingredient. Excipients are also sometimes used to bulk up formulations that contain active ingredients. As described herein, the "active ingredient" is an enzyme catalyst comprising at least one enzyme having perhydrolysis activity. In one embodiment, the active ingredient is at least one CE-7 carbohydrate esterase having perhydrolysis activity.

As used herein, the term "oligosaccharide excipient" means an oligosaccharide that, when added to an aqueous enzyme solution, improves recovery/retention of active enzyme (i.e., perhydrolase activity) after spray drying and/or improves storage stability of the resulting spray-dried enzyme powder or a formulation of the enzyme powder and a carboxylic acid ester. In one embodiment, the addition of the oligosaccharide excipient prior to spray drying improves the storage stability of the enzyme when stored in the carboxylic acid ester (i.e., a storage mixture substantially free of water). The carboxylic acid ester may contain a very low concentration of water, for example, triacetin typically has between 180 ppm and 300 ppm of water. As used herein, the phrase "substantially free of water" will refer to a concentration of water in a mixture of the enzyme powder and the carboxylic acid ester that does not adversely impact the storage stability of enzyme powder when present in the carboxylic acid ester. In a further embodiment, "substantially free of water" may mean less than 2000 ppm, preferably less than 1000 ppm, more preferably less than 500 ppm, and even more preferably less than 250 ppm of water in the formulation comprising the enzyme powder and the carboxylic acid ester.

Enzyme Powder

One aspect is for an enzyme powder comprising a formulation of at least one enzyme structurally classified as a CE-7 enzyme and having perhydrolysis activity, at least one excipient, and optionally at least one surfactant. In one embodiment, the enzyme powder is formed by spray drying.

In some embodiments, the at least one excipient is an oligosaccharide excipient has a number average molecular weight of at least about 1250 and a weight average molecular weight of at least about 9000.

The at least one enzyme can be any of the CE-7 carbohydrate esterases described herein or can be any of the CE-7 carbohydrate esterases described in co-owned, copending Published U.S. Patent Application Nos. 2008/0176299 and 2009/0005590 (each incorporated herein by reference in its entirety). In some embodiments, the at least one enzyme is selected from the group consisting of SEQ ID NOs: 1, 2, 3, 4, 5, 6, 7, 8, 9, 10, 11, 12, 13, 14, 15, 16, 17, 19, 20, 21, 22, 23, 24, and 25.

The at least one enzyme is present in the spray-dried formulation in an amount in a range of from about 5 wt % to about 75 wt % based on the dry weight of the spray-dried formulation. A preferred wt % range of enzyme in the spray-dried formulation is from about 10 wt % to 50 wt %, and a more preferred wt % range of enzyme in the spray-dried formulation is from about 20 wt % to 33 wt %

The spray-dried formulation further comprises at least one oligosaccharide excipient. In some embodiments, the at least one oligosaccharide excipient has a number average molecular weight of at least about 1250 and a weight average molecular weight of at least about 9000. In some embodiments, the oligosaccharide excipient has a number average molecular weight of at least about 1700 and a weight average molecular weight of at least about 15000. Specific oligosaccharides useful in the present invention include, but are not limited to, maltodextrin, xylan, mannan, fucoidan, galactomannan, chitosan, raffinose, stachyose, pectin, inulin, levan, graminan, and amylopectin, sucrose, lactulose, lactose, maltose, trehalose, cellobiose, nigerotriose, maltotriose, melezitose, maltotriulose, raffinose, kestose, and mixtures thereof. Oligosaccharide-based excipients useful in the present invention include, but are not limited to, water-soluble non-ionic cellulose ethers, such as hydroxymethyl-cellulose and hydroxypropylmethylcellulose, and mixtures thereof.

The excipient is present in the formulation in an amount in a range of from about 95 wt % to about 25 wt % based on the dry weight of the spray-dried formulation. A preferred wt % range of excipient in the spray-dried formulation is from about 90 wt % to 50 wt %, and a more preferred wt % range of excipient in the spray-dried formulation is from about 80 wt % to 67 wt %.

In some embodiments, the formulation further comprises at least one surfactant. Useful surfactants include, but are not limited to, ionic and nonionic surfactants or wetting agents, such as ethoxylated castor oil, polyglycolyzed glycerides, acetylated monoglycerides, sorbitan fatty acid esters, poloxamers, polyoxyethylene sorbitan fatty acid esters, polyoxyethylene derivatives, monoglycerides or ethoxylated derivatives thereof, diglycerides or polyoxyethylene derivatives thereof, sodium docusate, sodium laurylsulfate, cholic acid or derivatives thereof, lecithins, phospholipids, block copolymers of ethylene glycol and propylene glycol, and non-ionic organosilicones. Preferably, the surfactant is a polyoxyethylene sorbitan fatty ester, with polysorbate 80 being more preferred.

When part of the formulation, the surfactant is present in an amount in a range of from about 5 wt % to 0.1 wt % based on the weight of protein present in the spray dried formulation, preferably from about 2 wt % to 0.5 wt % based on the weight of protein present in the spray dried formulation.

The spray dried formulation may additionally comprise one or more buffers (such as sodium and/or potassium salts of bicarbonate, citrate, acetate, phosphate, pyrophosphate, methylphosphonate, succinate, malate, fumarate, tartrate, or maleate), and an enzyme stabilizer (e.g., ethylenediaminetetraacetic acid, (1-hydroxyethylidene)bisphosphonic acid).

Spray drying of the formulation of at least one enzyme, at least one oligosaccharide excipient, and optionally at least one surfactant is carried out, for example, as described generally in the *Spray Drying Handbook*, 5$^{th}$ ed., K. Masters, John Wiley & Sons, Inc., NY, N.Y. (1991), and in PCT Patent Publication Nos. WO 97/41833 (1997) and WO 96/32149 (1996) to Platz, R., et al.

In general spray drying consists of bringing together a highly dispersed liquid and a sufficient volume of hot air to produce evaporation and drying of the liquid droplets. Typically the feed is sprayed into a current of warm filtered air that evaporates the solvent and conveys the dried product to a collector. The spent air is then exhausted with the solvent. Those skilled in the art will appreciate that several different types of apparatus may be used to provide the desired product. For example, commercial spray dryers manufactured by Buchi Ltd. (Postfach, Switzerland) or GEA Niro Corp. (Copenhagen, Denmark) will effectively produce particles of desired size. It will further be appreciated that these spray dryers, and specifically their atomizers, may be modified or customized for specialized applications, such as the simultaneous spraying of two solutions using a double nozzle technique. More specifically, a water-in-oil emulsion can be atomized from one nozzle and a solution containing an anti-adherent such as mannitol can be co-atomized from a second nozzle. In other cases it may be desirable to push the feed solution though a custom designed nozzle using a high pressure liquid chromatography (HPLC) pump. Provided that microstructures comprising the correct morphology and/or composition are produced the choice of apparatus is not critical and would be apparent to the skilled artisan in view of the teachings herein.

The temperature of both the inlet and outlet of the gas used to dry the sprayed material is such that it does not cause degradation of the enzyme in the sprayed material. Such temperatures are typically determined experimentally, although generally, the inlet temperature will range from about 50° C. to about 225° C., while the outlet temperature will range from about 30° C. to about 150° C. Preferred parameters include atomization pressures ranging from about 20-150 psi (0.14 MPa-1.03 MPa), and preferably from about 30-40 to 100 psi (0.21-0.28 MPa to 0.69 MPa). Typically the atomization pressure employed will be one of the following (MPa) 0.14, 0.21, 0.28, 0.34, 0.41, 0.48, 0.55, 0.62, 0.69, 0.76, 0.83 or above.

The enzyme powder or a formulation of the enzyme powder in carboxylic acid ester substantially retains its enzymatic activity for an extended period of time when stored at ambient temperature. The enzyme powder or a formulation of the spray-dried enzyme powder in carboxylic acid ester substantially retains its enzymatic activity at elevated temperatures for short periods of time. In one embodiment, "substantially retains its enzymatic activity" is meant that the spray-dried enzyme powder or a formulation of the spray-dried enzyme powder in carboxylic acid ester retains at least about 75 percent of the enzyme activity of the enzyme in the spray-dried enzyme powder or a formulation of the spray-dried enzyme powder after an extended storage period at ambient temperature and/or after a short storage period at an elevated temperature (above ambient temperature) in a formulation comprised of a carboxylic acid ester and the enzyme powder as compared to the initial enzyme activity of the enzyme powder prior to the preparation of a formulation comprised of the carboxylic acid ester and the enzyme powder. The extended storage period is a period of time of from about one year to about two years at ambient temperature. In one embodiment, the short storage period is at an elevated temperature for a period of time of from when the formulation comprised of a carboxylic acid ester and the enzyme powder is produced at 40° C. to about eight weeks at 40° C. In another embodiment, the elevated temperature is in a range of from about 30° C. to about 52° C. In a preferred embodiment, the elevated temperature is in a range of from about 30° C. to about 40° C.

In some embodiments, the spray-dried enzyme powder has at least 75 percent of the enzyme activity of the at least one enzyme after eight weeks storage at 40° C. in a formulation comprised of a carboxylic acid ester and the enzyme powder as compared to the initial enzyme activity of the enzyme powder prior to the preparation of a formulation comprised of the carboxylic acid ester and the enzyme powder at 40° C. In other embodiments, the enzyme powder has at least 76, 77, 78, 79, 80, 81, 82, 83, 84, 85, 86, 87, 88, 89, 90, 91, 92, 93, 94, 95, 96, 97, 98, 99, or 100 percent of the enzyme activity of the at least one enzyme after eight weeks storage at 40° C. in a formulation comprised of a carboxylic acid ester and the enzyme powder as compared to the initial enzyme activity of the enzyme powder prior to the preparation of a formulation comprised of the carboxylic acid ester and the enzyme powder at 40° C. Preferably, perhydrolysis activity is measured as described in Example 8-13, infra, but any method of measuring perhydrolysis activity can be used in the practice of the present invention.

In some embodiments, further improvement in enzyme activity over the stated periods of time can be achieved by adding a buffer having a buffering capacity in a pH range of from about 5.5 to about 9.5 to the formulation comprised of the carboxylic acid ester and the spray-dried enzyme powder. Suitable buffer for use in the formulation may include, but is not limited to, sodium salt, potassium salt, or mixtures of sodium or potassium salts of bicarbonate, pyrophosphate, phosphate, methylphosphonate, citrate, acetate, malate, fumarate, tartrate maleate or succinate. Preferred buffers for use in the formulation comprised of the carboxylic acid ester and the spray-dried enzyme powder include the sodium salt, potassium salt, or mixtures of sodium or potassium salts of bicarbonate, phosphate, methylphosphonate, or citrate.

In embodiments where a buffer is present in the carboxylic acid ester and enzyme powder formulation, the buffer may be present in an amount in a range of from about 0.01 wt % to about 50 wt % based on the weight of carboxylic acid ester in the formulation comprised of carboxylic acid ester and enzyme powder. The buffer may be present in a more preferred range of from about 0.10% to about 10% based on the weight of carboxylic acid ester in the formulation comprised of carboxylic acid ester and enzyme powder. Further, in these embodiments, the comparison between perhydrolysis activities of the enzyme is determined as between (a) an enzyme powder which retains at least 75 percent of the perhydrolysis activity of the at least one enzyme after eight weeks storage at 40° C. in a formulation comprised of a carboxylic acid ester, a buffer having a buffering capacity in a pH range of from about 5.5 to about 9.5, and the enzyme powder and (b) the initial perhydrolysis activity of the enzyme powder prior to the preparation of a formulation comprised of the carboxylic acid ester, the buffer having a buffering capacity in a pH range of from about 5.5 to about 9.5, and the enzyme powder.

It is intended that the enzyme powder be stored as a formulation in the organic compound that is a substrate for the at least one enzyme, such as triacetin. In the absence of added hydrogen peroxide, triacetin is normally hydrolyzed in aqueous solution by a CE-7 carbohydrate esterase to produce diacetin and acetic acid, and the production of acetic acid results in a decrease in the pH of the reaction mixture. One requirement for long term storage stability of the enzyme in triacetin is that there not be significant reaction of the triacetin with any water that might be present in the triacetin; the specification for water content in one commercial triacetin (supplied by Tessenderlo Group, Brussels, Belgium) is 0.03 wt % water (300 ppm). Any hydrolysis of triacetin that occurs during storage of the enzyme in triacetin would produce acetic acid, which could result in a decrease in activity or inactivation of the perhydrolysis activity of the CE-7 carbohydrate esterases; the perhydrolase activity of the CE-7 carbohydrate esterases is typically inactivated at or below a pH of 5.0 (see U.S. patent application Ser. No. 12/539,025 to DiCosimo, R., et al.). The oligosaccharide excipient selected for use in the present application must provide stability of the enzyme in the organic substrate for the enzyme under conditions where acetic acid might be generated due to the presence of low concentrations of water in the formulation.

Suitable Reaction Conditions for the Enzyme-catalyzed Preparation of Peracids from Carboxylic Acid Esters and Hydrogen Peroxide In one aspect of the invention, a process is provided to produce an aqueous formulation comprising a peracid by reacting one or more carboxylic acid esters with source of peroxygen (hydrogen peroxide, sodium perborate or sodium percarbonate) in the presence of an enzyme catalyst having perhydrolysis activity. In one embodiment, the enzyme catalyst comprises at least one enzyme having perhydrolysis activity, wherein said enzyme is structurally classified as a member of the CE-7 carbohydrate esterase family (CE-7; see Coutinho, P. M., Henrissat, B., supra). In another embodiment, the perhydrolase catalyst is structurally classified as a cephalosporin C deacetylase. In another embodiment, the perhydrolase catalyst is structurally classified as an acetyl xylan esterase.

In one embodiment, the perhydrolase catalyst comprises an enzyme having perhydrolysis activity and a signature motif comprising:

a) an RGQ motif as amino acid residues 118-120;
b) a GXSQG motif at amino acid residues 179-183; and
c) an HE motif as amino acid residues 298-299 when aligned to reference sequence SEQ ID NO:1 using CLUSTALW.

In a further embodiment, the signature motif additional comprises a fourth conserved motif defined as an LXD motif at amino acid residues 267-269 when aligned to reference sequence SEQ ID NO:1 using CLUSTALW.

In another embodiment, the perhydrolase catalyst comprises an enzyme having the present signature motif and at least 30% amino acid to SEQ ID NO:1.

In another embodiment, the perhydrolase catalyst comprises an enzyme having perhydrolase activity selected from the group consisting of SEQ ID NOs: 1, 2, 3, 4, 5, 6, 7, 8, 9, 10, 11, 12, 13, 14, 15, 16, 17, 19, 20, 21, 22, 23, 24, and 25.

In another embodiment, the perhydrolase catalyst comprises an enzyme having at least 40% amino acid identity to a contiguous signature motif defined as SEQ ID NO: 18 wherein the conserved motifs described above (i.e., RGQ, GXSQG, and HE, and optionally, LXD) are conserved.

In another embodiment, the perhydrolase catalyst comprises an enzyme having an amino acid sequence selected from the group consisting of SEQ ID NOs: 1, 2, 3, 4, 5, 6, 7, 8, 9, 10, 11, 12, 13, 14, 15, 16, 17, 19, 20, 21, 22, 23, 24, and 25, wherein said enzyme may have one or more additions, deletions, or substitutions so long as the signature motif is conserved and perhydrolase activity is retained.

Suitable carboxylic acid ester substrates may include esters provided by the following formula:

wherein X=an ester group of the formula $R_6C(O)O$ $R_6$=C1 to C7 linear, branched or cyclic hydrocarbyl moiety, optionally substituted with hydroxyl groups or C1 to C4 alkoxy groups, wherein $R_6$ optionally comprises one or more ether linkages for $R_6$=C2 to C7;

$R_5$=a C1 to C6 linear, branched, or cyclic hydrocarbyl moiety optionally substituted with hydroxyl groups; wherein each carbon atom in $R_5$ individually comprises no more than one hydroxyl group or no more than one ester group; wherein $R_5$ optionally comprises one or more ether linkages;

m=1 to the number of carbon atoms in $R_5$; and wherein said esters have solubility in water of at least 5 ppm at 25° C.

In other embodiments, suitable substrates may also include esters of the formula:

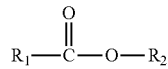

wherein $R_1$=C1 to C7 straight chain or branched chain alkyl optionally substituted with a hydroxyl or a C1 to C4 alkoxy group and $R_2$=C1 to C10 straight chain or branched chain alkyl, alkenyl, alkynyl, aryl, alkylaryl, alkylheteroaryl, heteroaryl, $(CH_2CH_2\text{—}O)_n H$ or $(CH_2CH(CH_3)\text{—}O)_n H$ and n=1 to 10.

In other embodiments, suitable carboxylic acid ester substrates may include glycerides of the formula:

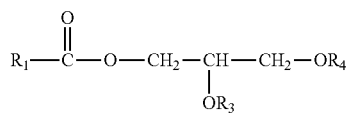

wherein $R_1$=C1 to C7 straight chain or branched chain alkyl optionally substituted with a hydroxyl or a C1 to C4 alkoxy group and $R_3$ and $R_4$ are individually H or $R_1C(O)$.

In other embodiments, $R_6$ is C1 to C7 linear hydrocarbyl moiety, optionally substituted with hydroxyl groups or C1 to C4 alkoxy groups, optionally comprising one or more ether linkages. In further preferred embodiments, $R_6$ is C2 to C7 linear hydrocarbyl moiety, optionally substituted with hydroxyl groups, and/or optionally comprising one or more ether linkages.

In other embodiments, suitable carboxylic acid ester substrates may also include acetylated saccharides selected from the group consisting of acetylated mono-, di-, and polysaccharides. In preferred embodiments, the acetylated saccharides include acetylated mono-, di-, and polysaccharides. In other embodiments, the acetylated saccharides are selected from the group consisting of acetylated xylan, fragments of acetylated xylan, acetylated xylose(such as xylose tetraacetate), acetylated glucose (such as glucose pentaacetate), β-D-ribofuranose-1,2,3,5-tetraacetate, tri-O-acetyl-D-galactal, tri-O-acetyl-D-glucal, and acetylated cellulose. In preferred embodiments, the acetylated saccharide is selected from the group consisting of β-D-ribofuranose-1,2,3,5-tetraacetate, tri-O-acetyl-D-galactal, tri-O-acetyl-D-glucal, and acetylated cellulose. As such, acetylated carbohydrates may be suitable substrates for generating percarboxylic acids using the present methods and systems (i.e., in the presence of a peroxygen source).

In additional embodiments, the carboxylic acid ester substrate may be monoacetin; triacetin; monopropionin; dipropionin; tripropionin; monobutyrin; dibutyrin; tributyrin; glucose pentaacetate; xylose tetraacetate; acetylated xylan; acetylated xylan fragments; β-D-ribofuranose-1,2,3,5-tetraacetate; tri-O-acetyl-D-galactal; tri-O-acetyl-D-glucal; propylene glycol diacetate; ethylene glycol diacetate; monoesters or diesters of 1,2-ethanediol; 1,2-propanediol; 1,3-propanediol; 1,2-butanediol; 1,3-butanediol; 2,3-butanediol; 1,4-butanediol; 1,2-pentanediol; 2,5-pentanediol; 1,6-pentanediol; 1,2-hexanediol; 2,5-hexanediol; 1,6-hexanediol; and mixtures thereof. In preferred embodiments of the present methods and systems, the substrate comprises triacetin.

The carboxylic acid ester is present in the reaction formulation at a concentration sufficient to produce the desired concentration of peracid upon enzyme-catalyzed perhydrolysis. The carboxylic acid ester need not be completely soluble in the reaction formulation, but has sufficient solubility to permit conversion of the ester by the perhydrolase catalyst to the corresponding peracid. The carboxylic acid ester is present in the reaction formulation at a concentration of 0.05 wt % to 40 wt % of the reaction formulation, preferably at a concentration of 0.1 wt % to 20 wt % of the reaction formulation, and more preferably at a concentration of 0.5 wt % to 10 wt % of the reaction formulation.

The peroxygen source may include, but is not limited to, hydrogen peroxide, hydrogen peroxide adducts (e.g., urea-hydrogen peroxide adduct (carbamide peroxide)) perborate salts and percarbonate salts. The concentration of peroxygen compound in the reaction formulation may range from 0.0033 wt % to about 50 wt %, preferably from 0.033 wt % to about 40 wt %, more preferably from 0.33 wt % to about 30 wt %.

Many perhydrolase catalysts (whole cells, permeabilized whole cells, and partially purified whole cell extracts) have been reported to have catalase activity (EC 1.11.1.6). Catalases catalyze the conversion of hydrogen peroxide into oxygen and water. In one aspect, the perhydrolysis catalyst lacks catalase activity. In another aspect, a catalase inhibitor is added to the reaction formulation. Examples of catalase inhibitors include, but are not limited to, sodium azide and hydroxylamine sulfate. One of skill in the art can adjust the concentration of catalase inhibitor as needed. The concentration of the catalase inhibitor typically ranges from 0.1 mM to about 1 M; preferably about 1 mM to about 50 mM; more preferably from about 1 mM to about 20 mM. In one aspect, sodium azide concentration typically ranges from about 20 mM to about 60 mM while hydroxylamine sulfate is concentration is typically about 0.5 mM to about 30 mM, preferably about 10 mM.

In another embodiment, the enzyme catalyst lacks significant catalase activity or is engineered to decrease or eliminate catalase activity. The catalase activity in a host cell can be down-regulated or eliminated by disrupting expression of the gene(s) responsible for the catalase activity using well known techniques including, but not limited to, transposon mutagenesis, RNA antisense expression, targeted mutagenesis, and random mutagenesis. In a preferred embodiment, the gene(s) encoding the endogenous catalase activity are down-regulated or disrupted (i.e. knocked-out). As used herein, a "disrupted" gene is one where the activity and/or function of the protein encoded by the modified gene is no longer present. Means to disrupt a gene are well-known in the art and may include, but are not limited to, insertions, deletions, or mutations to the gene so long as the activity and/or function of the corresponding protein is no longer present. In a further preferred embodiment, the production host is an *E. coli* production host comprising a disrupted catalase gene selected from the group consisting of katG and katE (see Published U.S. Patent Application No. 20080176299). In another embodiment, the production host is an *E. coli* strain comprising a down-regulation and/or disruption in both katg1 and a katE catalase genes.

The concentration of the catalyst in the aqueous reaction formulation depends on the specific catalytic activity of the catalyst, and is chosen to obtain the desired rate of reaction. The weight of catalyst in perhydrolysis reactions typically ranges from 0.0001 mg to 10 mg per mL of total reaction volume, preferably from 0.001 mg to 2.0 mg per mL. The catalyst may also be immobilized on a soluble or insoluble support using methods well-known to those skilled in the art; see for example, *Immobilization of Enzymes and Cells*; Gordon F. Bickerstaff, Editor; Humana Press, Totowa, N.J., USA; 1997. The use of immobilized catalysts permits the recovery and reuse of the catalyst in subsequent reactions. The enzyme catalyst may be in the form of whole microbial cells, permeabilized microbial cells, microbial cell extracts, partially-purified or purified enzymes, and mixtures thereof.

In one aspect, the concentration of peracid generated by the combination of chemical perhydrolysis and enzymatic perhydrolysis of the carboxylic acid ester is sufficient to provide an effective concentration of peracid for bleaching or disinfection at a desired pH. In another aspect, the present methods provide combinations of enzymes and enzyme substrates to produce the desired effective concentration of peracid, where, in the absence of added enzyme, there is a significantly lower concentration of peracid produced. Although there may in some cases be substantial chemical perhydrolysis of the enzyme substrate by direct chemical reaction of inorganic peroxide with the enzyme substrate, there may not be a sufficient concentration of peracid generated to provide an effective concentration of peracid in the desired applications, and a significant increase in total peracid concentration is achieved by the addition of an appropriate perhydrolase catalyst to the reaction formulation.

The concentration of peracid generated (such as peracetic acid) by the perhydrolysis of at least one carboxylic acid ester is at least about 20 ppm, preferably at least 100 ppm, more preferably at least about 200 ppm peracid, more preferably at least 300 ppm, more preferably at least 500 ppm, more preferably at least 700 ppm, more preferably at least about 1000 ppm peracid, most preferably at least 2000 ppm peracid within 10 minutes, preferably within 5 minutes, more preferably within 1 minute of initiating the perhydrolysis reaction. The product formulation comprising the peracid may be optionally diluted with water, or a solution predominantly comprised of water, to produce a formulation with the desired lower concentration of peracid. In one aspect, the reaction time required to produce the desired concentration of peracid is not greater than about two hours, preferably not greater than about 30 minutes, more preferably not greater than about 10 minutes, and most preferably in about 5 minutes or less. In other aspects, a hard surface or inanimate object contaminated with a biological contaminant(s) is contacted with the peracid formed in accordance with the processes described herein within about 5 minutes to about 168 hours of combining said reaction components, or within about 5 minutes to about 48 hours, or within about 5 minutes to 2 hours of combining said reaction components, or any such time interval therein.

In another aspect, the peroxycarboxylic acid formed in accordance with the processes describe herein is used in a laundry care application wherein the peroxycarboxylic acid is contacted with at least one article of clothing or textile to provide a benefit, such as disinfecting, bleaching, destaining, sanitizing, deodorizing or a combination thereof. The peroxycarboxylic acid may be used in a variety of laundry care products including, but not limited to, textile pre-wash treatments, laundry detergents, stain removers, bleaching compositions, deodorizing compositions, and rinsing agents. In one embodiment, the present process to produce a peroxycarboxylic acid for a target surface is conducted in situ.

In the context of laundry care applications, the term "contacting an article of clothing or textile" means that the article of clothing or textile is exposed to a formulation disclosed herein. To this end, there are a number of formats the formulation may be used to treat fabric including, but not limited to, liquid, solids, gel, paste, bars, tablets, spray, foam, powder, or granules and can be delivered via hand dosing, unit dosing, dosing from a substrate, spraying and automatic dosing from a laundry washing or drying machine. Granular compositions can also be in compact form; liquid compositions can also be in a concentrated form.

When the formulations disclosed herein are used in a laundry machine, the formulation can further contain components typical to laundry detergents. For example, typical components included, but are not limited to, surfactants, bleaching agents, bleach activators, additional enzymes, suds suppressors, dispersants, lime-soap dispersants, soil suspension and anti-redeposition agents, softening agents, corrosion inhibitors, tarnish inhibitors, germicides, pH adjusting agents, non-builder alkalinity sources, chelating agents, organic and/or inorganic fillers, solvents, hydrotropes, optical brighteners, dyes, and perfumes.

The formulations disclosed herein can also be used as detergent additive products in solid or liquid form. Such additive products are intended to supplement or boost the performance of conventional detergent compositions and can be added at any stage of the cleaning process.

In connection with the present systems and methods for laundry care where the peracid is generated for one or more of bleaching, stain removal, and odor reduction, the concentration of peracid generated (e.g., peracetic acid) by the perhydrolysis of at least one carboxylic acid ester may be at least about 2 ppm, preferably at least 20 ppm, preferably at least 100 ppm, and more preferably at least about 200 ppm peracid. In connection with the present systems and methods for laundry care where the peracid is generated for disinfection or sanitization, the concentration of peracid generated (e.g., peracetic acid) by the perhydrolysis of at least one carboxylic acid ester may be at least about 2 ppm, more preferably at least 20 ppm, more preferably at least 200 ppm, more preferably at least 500 ppm, more preferably at least 700 ppm, more preferably at least about 1000 ppm peracid, most preferably at least 2000 ppm peracid within 10 minutes, preferably within 5 minutes, and most preferably within 1 minute of initiating the perhydrolysis reaction. The product mixture comprising the peracid may be optionally diluted with water, or a solution predominantly comprised of water, to produce a mixture with the desired lower concentration of peracid. In one aspect of the present methods and systems, the reaction time required to produce the desired concentration of peracid is not greater than about two hours, preferably not greater than about 30 minutes, more preferably not greater than about 10 minutes, even more preferably not greater than about 5 minutes, and most preferably in about 1 minute or less.

The temperature of the reaction is chosen to control both the reaction rate and the stability of the enzyme catalyst activity. The temperature of the reaction may range from just above the freezing point of the reaction formulation (approximately 0° C.) to about 95° C., with a preferred range of reaction temperature of from about 5° C. to about 55° C. The pH of the final reaction formulation containing peracid is from about 2 to about 9, preferably from about 3 to about 8, more preferably from about 5 to about 8, even more preferably about 5.5 to about 8, and yet even more preferably about 6.0 to about 7.5. In another embodiment, the pH of the reaction formulation is acidic (pH<7). The pH of the reaction, and of the final reaction formulation, may optionally be controlled by the addition of a suitable buffer, including, but not limited to, bicarbonate, pyrophosphate, phosphate, methylphosphonate, citrate, acetate, malate, fumarate, tartrate maleate or succinate. The concentration of buffer, when employed, is typically from 0.1 mM to 1.0 M, preferably from 1 mM to 300 mM, most preferably from 10 mM to 100 mM.

In another aspect, the enzymatic perhydrolysis reaction formulation may contain an organic solvent that acts as a dispersant to enhance the rate of dissolution of the carboxylic acid ester in the reaction formulation. Such solvents include, but are not limited to, propylene glycol methyl ether, acetone, cyclohexanone, diethylene glycol butyl ether, tripropylene glycol methyl ether, diethylene glycol methyl ether, propylene glycol butyl ether, dipropylene glycol methyl ether, cyclohexanol, benzyl alcohol, isopropanol, ethanol, propylene glycol, and mixtures thereof.

In another aspect, the enzymatic perhydrolysis product may contain additional components that provide desirable functionality. These additional components include, but are not limited to, buffers, detergent builders, thickening agents, emulsifiers, surfactants, wetting agents, corrosion inhibitors (such as benzotriazole), enzyme stabilizers, and peroxide stabilizers (e.g., metal ion chelating agents). Many of the additional components are well known in the detergent industry (see, for example, U.S. Pat. No. 5,932,532; hereby incorporated by reference). Examples of emulsifiers include, but are not limited to polyvinyl alcohol or polyvinylpyrrolidone. Examples of thickening agents include, but are not limited to, LAPONITE® RD, corn starch, PVP, CARBOWAX®, CARBOPOL®, CABOSIL®, polysorbate 20, PVA, and lecithin. Examples of buffering systems include, but are not limited to, sodium phosphate monobasic/sodium phosphate dibasic; sulfamic acid/triethanolamine; citric acid/triethanolamine; tartaric acid/triethanolamine; succinic acid/triethanolamine; and acetic acid/triethanolamine. Examples of surfactants include, but are not limited to, a) non-ionic surfactants such as block copolymers of ethylene oxide or propylene oxide, ethoxylated or propoxylated linear and branched primary and secondary alcohols, and aliphatic phosphine oxides; b) cationic surfactants such as quaternary ammonium compounds, particularly quaternary ammonium compounds having a C8-C20 alkyl group bound to a nitrogen atom additionally bound to three C1-C2 alkyl groups; c) anionic surfactants such as alkane carboxylic acids (e.g., C8-C20 fatty acids), alkyl phosphonates, alkane sulfonates (e.g., sodium dodecylsulphate "SDS") or linear or branched alkyl benzene sulfonates, alkene sulfonates; and d) amphoteric and zwitterionic surfactants, such as aminocarboxylic acids, aminodicarboxylic acids, alkybetaines, and mixtures thereof. Additional components may include fragrances, dyes, stabilizers of hydrogen peroxide (e.g., metal chelators such as 1-hydroxyethylidene-1,1-diphosphonic acid (DEQUEST® 2010, Solutia Inc., St. Louis, Mo. and ethylenediaminetetraacetic acid (EDTA)), TURPINAL® SL (CAS#2809-21-4), DEQUEST® 0520, DEQUEST® 0531, stabilizers of enzyme activity (e.g., polyethylene glycol (PEG)), and detergent builders.

In Situ Production of Peracids using a Perhydrolase Catalyst

Cephalosporin C deacetylases (E.C. 3.1.1.41; systematic name cephalosporin C acetylhydrolases; CAHs) are enzymes having the ability to hydrolyze the acetyl ester bond on cephalosporins such as cephalosporin C, 7-aminocephalosporanic acid, and 7-(thiophene-2-acetamido)cephalosporanic acid (Abbott, B. and Fukuda, D., *Appl. Microbiol.* 30(3):413-419 (1975)). CAHs belong to a larger family of structurally related enzymes referred to as the carbohydrate esterase family seven ("CE-7"; Coutinho, P. M., Henrissat, B., supra).

The CE-7 carbohydrate esterase family includes both CAHs and acetyl xylan esterases (AXEs; E.C. 3.1.1.72). CE-7 family members share a common structural motif and are quite unusual in that they typically exhibit ester hydrolysis activity for both acetylated xylooligosaccharides and acetylated cephalosporin C, suggesting that the CE-7 family represents a single class of proteins with a multifunctional deacetylase activity against a range of small substrates (Vincent et al., supra). Vincent et al. describes the structural similarity among the members of this family and defines a signature sequence motif characteristic of the CE-7 family.

Members of the CE-7 family are found in plants, fungi (e.g., *Cephalosporidium acremonium*), yeasts (e.g., *Rhodosporidium toruloides, Rhodotorula glutinis*), and bacteria such as *Thermoanaerobacterium* sp.; *Norcardia lactamdurans*, and various members of the genus *Bacillus* (Politino et al., *Appl. Environ. Microbiol.*, 63(12):4807-4811 (1997); Sakai et al., *J. Ferment. Bioeng.* 85:53-57 (1998); Lorenz, W. and Wiegel, J., *J. Bacteriol* 179:5436-5441 (1997); Cardoza et al., *Appl. Microbiol. Biotechnol.*, 54(3):406-412 (2000); Mitsushima et al., supra; Abbott, B. and Fukuda, D., *Appl. Microbiol.* 30(3):413-419 (1975); Vincent et al., supra, Takami et al., *NAR*, 28(21):4317-4331 (2000); Rey et al., *Genome Biol.*, 5(10): article 77 (2004); Degrassi et al., *Microbiology.*, 146:1585-1591 (2000); U.S. Pat. No. 6,645,233; U.S. Pat. No. 5,281,525; U.S. Pat. No. 5,338,676; and WO 99/03984.

WO2007/070609 and U.S. Patent Application Publication Nos. 2008/0176299 and 2008/176783 to DiCosimo et al. disclose various enzymes structurally classified as CE-7 enzymes that have perhydrolysis activity suitable for producing efficacious concentrations of peracids from a variety of carboxylic acid ester substrates when combined with a source of peroxygen. Variant CE-7 enzymes having improved perhydrolysis activity are also described in a co-filed, co-owned, and copending U.S. patent application Ser. No. 12/572,094, incorporated herein by reference in its entirety).

The present method produces industrially-useful, efficacious concentrations of peracids in situ under aqueous reaction conditions using the perhydrolase activity of an enzyme belonging to the CE-7 family of carbohydrate esterases.

HPLC Assay Method for Determining the Concentration of Peracid and Hydrogen Peroxide.

A variety of analytical methods can be used in the present methods to analyze the reactants and products including, but not limited to, titration, high performance liquid chromatography (HPLC), gas chromatography (GC), mass spectroscopy (MS), capillary electrophoresis (CE), the analytical procedure described by U. Karst et al., (*Anal. Chem.*, 69(17): 3623-3627 (1997)), and the 2,2'-azino-bis(3-ethylbenzothazoline)-6-sulfonate (ABTS) assay (S. Minning, et al., *Analytica Chimica Acta* 378:293-298 (1999) and WO 2004/058961 A1) as described in the present examples.

Determination of Minimum Biocidal Concentration of Peracids

The method described by J. Gabrielson, et al. (*J. Microbiol. Methods* 50: 63-73 (2002)) can be employed for determination of the Minimum Biocidal Concentration (MBC) of peracids, or of hydrogen peroxide and enzyme substrates. The assay method is based on XTT reduction inhibition, where XTT ((2,3-bis[2-methoxy-4-nitro-5-sulfophenyl]-5-[(phenylamino)carbonyl]-2H-tetrazolium, inner salt, monosodium salt) is a redox dye that indicates microbial respiratory activity by a change in optical density (OD) measured at 490 nm or 450 nm. However, there are a variety of other methods available for testing the activity of disinfectants and antiseptics including, but not limited to, viable plate counts, direct microscopic counts, dry weight, turbidity measurements, absorbance, and bioluminescence (see, for example Brock, Semour S., *Disinfection, Sterilization, and Preservation*, 5$^{th}$ edition, Lippincott Williams & Wilkins, Philadelphia, Pa., USA; 2001).

Uses of Enzymatically Prepared Peroxycarboxylic acid Compositions

The enzyme catalyst-generated peroxycarboxylic acid produced according to the present method can be used in a variety of hard surface/inanimate object applications for reduction of concentrations of biological contaminants, such as decontamination of medical instruments (e.g., endoscopes), textiles (e.g., garments, carpets), food preparation surfaces, food storage and food-packaging equipment, materials used for the packaging of food products, chicken hatcheries and grow-out facilities, animal enclosures, and spent process waters that have microbial and/or virucidal activity. The enzyme-generated peroxycarboxylic acids may be used in formulations designed to inactivate prions (e.g., certain proteases) to additionally provide biocidal activity. In a preferred aspect, the present peroxycarboxylic acid compositions are particularly useful as a disinfecting agent for non-autoclavable medical instruments and food packaging equipment. As the peroxycarboxylic acid-containing formulation may be prepared using GRAS or food-grade components (enzyme, enzyme substrate, hydrogen peroxide, and buffer), the enzyme-generated peroxycarboxylic acid may also be used for decontamination of animal carcasses, meat, fruits and vegetables, or for decontamination of prepared foods. The enzyme-generated peroxycarboxylic acid may be incorporated into a product whose final form is a powder, liquid, gel, film, solid or aerosol. The enzyme-generated peroxycarboxylic acid may be diluted to a concentration that still provides an efficacious decontamination.

The compositions comprising an efficacious concentration of peroxycarboxylic acid can be used to disinfect surfaces and/or objects contaminated (or suspected of being contaminated) with biological contaminants by contacting the surface or object with the products produced by the present processes. As used herein, "contacting" refers to placing a disinfecting composition comprising an effective concentration of peroxycarboxylic acid in contact with the surface or inanimate object suspected of contamination with a biological contaminant for a period of time sufficient to clean and disinfect. Contacting includes spraying, treating, immersing, flushing, pouring on or in, mixing, combining, painting, coating, applying, affixing to and otherwise communicating a peroxycarboxylic acid solution or composition comprising an efficacious concentration of peroxycarboxylic acid, or a solution or composition that forms an efficacious concentration of peroxycarboxylic acid, with the surface or inanimate object suspected of being contaminated with a concentration of a biological contaminant. The disinfectant compositions may be combined with a cleaning composition to provide both cleaning and disinfection. Alternatively, a cleaning agent (e.g., a surfactant or detergent) may be incorporated into the formulation to provide both cleaning and disinfection in a single composition.

The compositions comprising an efficacious concentration of peroxycarboxylic acid can also contain at least one additional antimicrobial agent, combinations of prion-degrading proteases, a virucide, a sporicide, or a biocide. Combinations of these agents with the peroxycarboxylic acid produced by the claimed processes can provide for increased and/or synergistic effects when used to clean and disinfect surfaces and/or objects contaminated (or suspected of being contaminated) with biological contaminants. Suitable antimicrobial agents include carboxylic esters (e.g., p-hydroxy alkyl benzoates and alkyl cinnamates); sulfonic acids (e.g., dodecylbenzene sulfonic acid); iodo-compounds or active halogen compounds (e.g., elemental halogens, halogen oxides (e.g., NaOCl, HOCl, HOBr, ClO2), iodine, interhalides (e.g., iodine monochloride, iodine dichloride, iodine trichloride, iodine tetrachloride, bromine chloride, iodine monobromide, or iodine dibromide), polyhalides, hypochlorite salts, hypochlorous acid, hypobromite salts, hypobromous acid, chloro- and bromo-hydantoins, chlorine dioxide, and sodium chlorite); organic peroxides including benzoyl peroxide, alkyl benzoyl peroxides, ozone, singlet oxygen generators, and mixtures thereof; phenolic derivatives (such as o-phenyl phenol, o-benzyl-p-chlorophenol, tert-amyl phenol and $C_1$-$C_6$ alkyl hydroxy benzoates); quaternary ammonium compounds (such as alkyldimethylbenzyl ammonium chloride, dialkyldimethyl ammonium chloride and mixtures thereof); and mixtures of such antimicrobial agents, in an amount sufficient to provide the desired degree of microbial protection. Effective amounts of antimicrobial agents include about 0.001 wt % to about 60 wt % antimicrobial agent, about 0.01 wt % to about 15 wt % antimicrobial agent, or about 0.08 wt % to about 2.5 wt % antimicrobial agent.

In one aspect, the peroxycarboxylic acids formed by the present process can be used to reduce the concentration of viable biological contaminants (such as a viable microbial population) when applied on and/or at a locus. As used herein, a "locus" comprises part or all of a target surface suitable for disinfecting or bleaching. Target surfaces include all surfaces that can potentially be contaminated with biological contaminants. Non-limiting examples include equipment surfaces found in the food or beverage industry (such as tanks, conveyors, floors, drains, coolers, freezers, equipment surfaces, walls, valves, belts, pipes, drains, joints, crevasses, combinations thereof, and the like); building surfaces (such as walls, floors and windows); non-food-industry related pipes and drains, including water treatment facilities, pools and spas, and fermentation tanks; hospital or veterinary surfaces (such as walls, floors, beds, equipment (such as endoscopes), clothing worn in hospital/veterinary or other healthcare settings, including clothing, scrubs, shoes, and other hospital or veterinary surfaces); restaurant surfaces; bathroom surfaces; toilets; clothes and shoes; surfaces of barns or stables for livestock, such as poultry, cattle, dairy cows, goats, horses and pigs; hatcheries for poultry or for shrimp; and pharmaceutical or biopharmaceutical surfaces (e.g., pharmaceutical or biopharmaceutical manufacturing equipment, pharmaceutical or biopharmaceutical ingredients, pharmaceutical or biopharmaceutical excipients). Additional hard surfaces also include food products, such as beef, poultry, pork, vegetables, fruits, seafood, combinations thereof, and the like. The locus can also include water absorbent materials such as infected linens or other textiles. The locus also includes harvested plants or plant products including seeds, corms, tubers, fruit, and vegetables, growing plants, and especially crop growing plants, including cereals, leaf vegetables and salad crops, root vegetables, legumes, berried fruits, citrus fruits and hard fruits.

Non-limiting examples of hard surface materials are metals (e.g., steel, stainless steel, chrome, titanium, iron, copper, brass, aluminum, and alloys thereof), minerals (e.g., concrete), polymers and plastics (e.g., polyolefins, such as polyethylene, polypropylene, polystyrene, poly(meth)acrylate, polyacrylonitrile, polybutadiene, poly(acrylonitrile, butadiene, styrene), poly(acrylonitrile, butadiene), acrylonitrile butadiene; polyesters such as polyethylene terephthalate; and polyamides such as nylon). Additional surfaces include brick, tile, ceramic, porcelain, wood, vinyl, linoleum, and carpet.

The peroxycarboxylic acids formed by the present process may be used to provide a benefit to an article of clothing or textile including, but not limited to, bleaching, destaining, sanitizing, disinfecting, and deodorizing. The peroxycarboxylic acids formed by the present process may be used in any number of laundry care products including, but not limited to, textile pre-wash treatments, laundry detergents, stain removers, bleaching compositions, deodorizing compositions, and rinsing agents.

Recombinant Microbial Expression

The genes and gene products of the instant sequences may be produced in heterologous host cells, particularly in the cells of microbial hosts. Preferred heterologous host cells for expression of the instant genes and nucleic acid molecules are microbial hosts that can be found within the fungal or bacterial families and which grow over a wide range of temperature, pH values, and solvent tolerances. For example, it is contemplated that any of bacteria, yeast, and filamentous fungi may suitably host the expression of the present nucleic acid molecules. The perhydrolase may be expressed intracellularly, extracellularly, or a combination of both intracellularly and extracellularly, where extracellular expression renders recovery of the desired protein from a fermentation product more facile than methods for recovery of protein produced by intracellular expression. Transcription, translation and the protein biosynthetic apparatus remain invariant relative to the cellular feedstock used to generate cellular biomass; functional genes will be expressed regardless. Examples of host strains include, but are not limited to, bacterial, fungal or yeast species such as *Aspergillus, Trichoderma, Saccharomyces, Pichia, Phaffia, Kluyveromyces, Candida, Hansenula, Yarrowia, Salmonella, Bacillus, Acinetobacter, Zymomonas, Agrobacterium, Erythrobacter, Chlorobium, Chromatium, Flavobacterium, Cytophaga, Rhodobacter, Rhodococcus, Streptomyces, Brevibacterium, Corynebacteria, Mycobacterium, Deinococcus, Escherichia, Erwinia, Pantoea, Pseudomonas, Sphingomonas, Methylomonas, Methylobacter, Methylococcus, Methylosinus, Methylomicrobium, Methylocystis, Alcaligenes, Synechocystis, Synechococcus, Anabaena, Thiobacillus, Methanobacterium, Klebsiella,* and *Myxococcus*. In one embodiment, bacterial host strains include *Escherichia, Bacillus, Kluyveromyces,* and *Pseudomonas*. In a preferred embodiment, the bacterial host cell is *Escherichia coli*.

Large-scale microbial growth and functional gene expression may use a wide range of simple or complex carbohydrates, organic acids and alcohols or saturated hydrocarbons, such as methane or carbon dioxide in the case of photosynthetic or chemoautotrophic hosts, the form and amount of nitrogen, phosphorous, sulfur, oxygen, carbon or any trace micronutrient including small inorganic ions. The regulation of growth rate may be affected by the addition, or not, of specific regulatory molecules to the culture and which are not typically considered nutrient or energy sources.

Vectors or cassettes useful for the transformation of suitable host cells are well known in the art. Typically the vector or cassette contains sequences directing transcription and translation of the relevant gene, a selectable marker, and sequences allowing autonomous replication or chromosomal integration. Suitable vectors comprise a region 5' of the gene which harbors transcriptional initiation controls and a region 3' of the DNA fragment which controls transcriptional termination. It is most preferred when both control regions are derived from genes homologous to the transformed host cell and/or native to the production host, although such control regions need not be so derived.

Initiation control regions or promoters, which are useful to drive expression of the present cephalosporin C deacetylase coding region in the desired host cell are numerous and familiar to those skilled in the art. Virtually any promoter capable of driving these genes is suitable for the present invention including, but not limited to, CYC1, HIS3, GAL1, GAL10, ADH1, PGK, PHO5, GAPDH, ADC1, TRP1, URA3, LEU2, ENO, TPI (useful for expression in *Saccharomyces*); AOX1 (useful for expression in *Pichia*); and lac, araB, tet, trp, $IP_L$, $IP_R$, T7, tac, and trc (useful for expression in *Escherichia coli*) as well as the amy, apr, npr promoters and various phage promoters useful for expression in *Bacillus*.

Termination control regions may also be derived from various genes native to the preferred host cell. In one embodiment, the inclusion of a termination control region is optional. In another embodiment, the chimeric gene includes a termination control region derived from the preferred host cell.

Industrial Production

A variety of culture methodologies may be applied to produce the perhydrolase catalyst. For example, large-scale production of a specific gene product overexpressed from a recombinant microbial host may be produced by batch, fed-batch, and continuous culture methodologies. Batch and fed-batch culturing methods are common and well known in the art and examples may be found in Thomas D. Brock in *Biotechnology: A Textbook of Industrial Microbiology*, Second Edition, Sinauer Associates, Inc., Sunderland, Mass. (1989) and Deshpande, Mukund V., *Appl. Biochem. Biotechnol.*, 36:227 (1992).

Commercial production of the desired perhydrolase catalyst may also be accomplished with a continuous culture. Continuous cultures are an open system where a defined culture media is added continuously to a bioreactor and an equal amount of conditioned media is removed simultaneously for processing. Continuous cultures generally maintain the cells at a constant high liquid phase density where cells are primarily in log phase growth. Alternatively, continuous culture may be practiced with immobilized cells where carbon and nutrients are continuously added and valuable products, by-products or waste products are continuously removed from the cell mass. Cell immobilization may be performed using a wide range of solid supports composed of natural and/or synthetic materials.

Recovery of the desired perhydrolase catalysts from a batch fermentation, fed-batch fermentation, or continuous culture, may be accomplished by any of the methods that are known to those skilled in the art. For example, when the enzyme catalyst is produced intracellularly, the cell paste is separated from the culture medium by centrifugation or membrane filtration, optionally washed with water or an aqueous buffer at a desired pH, then a suspension of the cell paste in an aqueous buffer at a desired pH is homogenized to produce a cell extract containing the desired enzyme catalyst. The cell extract may optionally be filtered through an appropriate filter aid such as celite or silica to remove cell debris prior to a heat-treatment step to precipitate undesired protein from the enzyme catalyst solution. The solution containing the desired enzyme catalyst may then be separated from the precipitated cell debris and protein by membrane filtration or centrifugation, and the resulting partially-purified enzyme catalyst solution concentrated by additional membrane filtration, then optionally mixed with an appropriate carrier (for example, maltodextrin, phosphate buffer, citrate buffer, or mixtures thereof) and spray-dried to produce a solid powder comprising the desired enzyme catalyst.

When an amount, concentration, or other value or parameter is given either as a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope be limited to the specific values recited when defining a range.

General Methods

The following examples are provided to demonstrate preferred embodiments. It should be appreciated by those of skill in the art that the techniques disclosed in the examples which follow represent techniques discovered by the inventor to function well in the practice of the methods disclosed herein, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the presently disclosed methods.

All reagents and materials were obtained from DIFCO Laboratories (Detroit, Mich.), GIBCO/BRL (Gaithersburg, Md.), TCI America (Portland, Oreg.), Roche Diagnostics Corporation (Indianapolis, Ind.) or Sigma-Aldrich Chemical Company (St. Louis, Mo.), unless otherwise specified.

The following abbreviations in the specification correspond to units of measure, techniques, properties, or compounds as follows: "sec" or "s" means second(s), "min" means minute(s), "h" or "hr" means hour(s), "µL" means microliter(s), "mL" means milliliter(s), "L" means liter(s), "mM" means millimolar, "M" means molar, "mmol" means millimole(s), "ppm" means part(s) per million, "wt" means weight, "wt %" means weight percent, "g" means gram(s), "mg" means milligram(s), "µg" means microgram(s), "ng" means nanogram(s), "g" means gravity, "HPLC" means high performance liquid chromatography, "dd $H_2O$" means distilled and deionized water, "dcw" means dry cell weight, "ATCC" or "ATCC®" means the American Type Culture Collection (Manassas, Va.), "U" means unit(s) of perhydrolase activity, "rpm" means revolution(s) per minute, "Tg" means glass transition temperature, and "EDTA" means ethylenediaminetetraacetic acid.

EXAMPLE 1

Construction of a katG Catalase Disrupted *E. Coli* Strain

The coding region of the kanamycin resistance gene (kan; SEQ ID NO:26) was amplified from the plasmid pKD13 (SEQ ID NO: 27) by PCR (0.5 min at 94° C., 0.5 min at 55° C., 1 min at 70° C., 30 cycles) using primers identified as SEQ ID NO: 28 and SEQ ID NO: 29 to generate the PCR product identified as SEQ ID NO: 30. The katG nucleic acid sequence is provided as SEQ ID NO: 31 and the corresponding amino acid sequence is SEQ ID NO: 32. *E. coli* MG1655 (ATCC® 47076™) was transformed with the temperature-sensitive plasmid pKD46 (SEQ ID NO: 33), which contains the λ-Red recombinase genes (Datsenko and Wanner, (2000), PNAS USA 97:6640-6645), and selected on LB-amp plates for 24 h at 30° C. MG1655/pKD46 was transformed with 50-500 ng of the PCR product by electroporation (BioRad Gene Pulser, 0.2 cm cuvette, 2.5 kV, 200 W, 25 µF), and selected on LB-kan plates for 24 h at 37° C. Several colonies were streaked onto LB-kan plates and incubated overnight at 42° C. to cure the pKD46 plasmid. Colonies were checked to confirm a phenotype of kanR/ampS. Genomic DNA was isolated from several colonies using the PUREGENE® DNA purification system (Gentra Systems, Minneapolis, Minn.), and checked by PCR to confirm disruption of the katG gene using primers identified as SEQ ID NO:34 and SEQ ID NO:35. Several katG-disrupted strains were transformed with the temperature-sensitive plasmid pCP20 (SEQ ID NO:36), which contains the FLP recombinase, used to excise the kan gene, and selected on LB-amp plates for 24 h at 37° C. Several colonies were streaked onto LB plates and incubated overnight at 42° C. to cure the pCP20 plasmid. Two colonies were checked to confirm a phenotype of kanS/ampS, and called MG1655 KatG1 and MG1655 KatG2.

EXAMPLE 2

Construction of a katE Catalase Disrupted *E. Coli* Strain

The kanamycin resistance gene (SEQ ID NO:26) was amplified from the plasmid pKD13 (SEQ ID NO:27) by PCR (0.5 min at 94° C., 0.5 min at 55° C., 1 min at 70° C., 30 cycles) using primers identified as SEQ ID NO:37 and SEQ ID NO:38 to generate the PCR product identified as SEQ ID NO:39. The katE nucleic acid sequence is provided as SEQ ID NO:40 and the corresponding amino acid sequence is SEQ ID NO:41. *E. coli* MG1655 (ATCC® 47076™) was transformed with the temperature-sensitive plasmid pKD46 (SEQ ID NO:33), which contains the λ-Red recombinase genes, and selected on LB-amp plates for 24 h at 30° C. MG1655/pKD46 was transformed with 50-500 ng of the PCR product by electroporation (BioRad Gene Pulser, 0.2 cm cuvette, 2.5 kV, 200 W, 25 µF), and selected on LB-kan plates for 24 h at 37° C. Several colonies were streaked onto LB-kan plates and incubated overnight at 42° C. to cure the pKD46 plasmid. Colonies were checked to confirm a phenotype of kanR/ampS. Genomic DNA was isolated from several colonies using the PUREGENE® DNA purification system, and checked by PCR to confirm disruption of the katE gene using primers identified as SEQ ID NO:42 and SEQ ID NO:43. Several katE-disrupted strains were transformed with the temperature-sensitive plasmid pCP20 (SEQ ID NO:36), which contains the FLP recombinase, used to excise the kan gene, and selected on LB-amp plates for 24 h at 37° C. Several colonies were streaked onto LB plates and incubated overnight at 42° C. to cure the pCP20 plasmid. Two colonies were checked to confirm a phenotype of kanS/ampS, and called MG1655 KatE1 and MG1655 KatE2.

EXAMPLE 3

Construction of a katG Catalase and Kate Catalase Disrupted *E. Coli* Strain (KLP18)

The Kanamycin Resistance Gene (SEQ Id NO:26) was Amplified from the plasmid pKD13 (SEQ ID NO:27) by PCR (0.5 min at 94° C., 0.5 min at 55° C., 1 min at 70° C., 30 cycles) using primers identified as SEQ ID NO:37 and SEQ ID NO:38 to generate the PCR product identified as SEQ ID NO:39. *E. coli* MG1655 KatG1 (EXAMPLE 1) was transformed with the temperature-sensitive plasmid pKD46 (SEQ ID NO:33), which contains the λ-Red recombinase genes, and selected on LB-amp plates for 24 h at 30° C. MG1655 KatG1/pKD46 was transformed with 50-500 ng of the PCR product by electroporation (BioRad Gene Pulser, 0.2 cm cuvette, 2.5 kV, 200 W, 25 µF), and selected on LB-kan plates for 24 h at 37° C. Several colonies were streaked onto LB-kan plates and incubated overnight at 42° C. to cure the pKD46 plasmid. Colonies were checked to confirm a phenotype of kanR/ampS. Genomic DNA was isolated from several colonies using the PUREGENE® DNA purification system, and checked by PCR to confirm disruption of the katE gene using primers identified as SEQ ID NO:42 and SEQ ID NO:43. Several katE-disrupted strains (A katE) were transformed with the temperature-sensitive plasmid pCP20 (SEQ ID NO:36), which contains the FLP recombinase, used to excise the kan gene, and selected on LB-amp plates for 24 h at 37° C. Several colonies were streaked onto LB plates and incubated overnight at 42° C. to cure the pCP20 plasmid. Two colonies were checked to confirm a phenotype of kanS/ampS, and called MG1655 KatG1KatE18.1 and MG1655 KatG1KatE23. MG1655 KatG1KatE18.1 is designated *E. coli* KLP18.

EXAMPLE 4

Cloning and Expression of Perhydrolase from *Thermotoga neapolitana*

The coding region of the gene encoding acetyl xylan esterase from *Thermotoga neapolitana* as reported in GEN-BANK® (accession number AE000512; region 80481-81458; SEQ ID NO:44) was synthesized using codons optimized for expression in *E. coli* (DNA 2.0, Menlo Park, Calif.). The coding region of the gene was subsequently amplified by PCR (0.5 min at 94° C., 0.5 min at 55° C., 1 min at 70° C., 30 cycles) using primers identified as SEQ ID NO:45 and SEQ ID NO:46. The resulting nucleic acid product (SEQ ID NO:47) was subcloned into pTrcHis2-TOPO® to generate the plasmid identified as pSW196. The plasmid pSW196 was used to transform *E. coli* KLP18 (EXAMPLE 3) to generate the strain KLP18/pSW196. KLP18/pSW196 was grown in LB media at 37° C. with shaking up to $OD_{600nm}$=0.4-0.5, at which time IPTG was added to a final concentration of 1 mM, and incubation continued for 2-3 h. Cells were harvested by centrifugation and SDS-PAGE was performed to confirm expression of the perhydrolase at 20-40% of total soluble protein.

EXAMPLE 5

Cloning and Expression of Perhydrolase from *Thermotoga maritima* MSB8

The coding region of the gene encoding acetyl xylan esterase from *Thermotoga maritima* MSB8 as reported in GENBANK® (accession #NP_227893.1; SEQ ID NO: 48) was synthesized (DNA 2.0, Menlo Park, Calif.). The coding region of the gene was subsequently amplified by PCR (0.5 min @ 94° C., 0.5 min @ 55° C., 1 min @ 70° C., 30 cycles) using primers identified as SEQ ID NO:49 and SEQ ID NO:50. The resulting nucleic acid product (SEQ ID NO:51) was cut with restriction enzymes PstI and XbaI and subcloned between the PstI and XbaI sites in pUC19 to generate the plasmid identified as pSW207. The plasmid pSW207 was used to transform *E. coli* KLP18 (EXAMPLE 3) to generate the strain identified as KLP18/pSW207. KLP18/pSW207 was grown in LB media at 37° C. with shaking up to $OD_{600nm}$=0.4-0.5, at which time IPTG was added to a final concentration of 1 mM, and incubation continued for 2-3 h. Cells were harvested by centrifugation and SDS-PAGE was performed to confirm expression of the perhydrolase enzyme at 20-40% of total soluble protein.

EXAMPLE 6

Fermentation of *E. coli* KLP18 Transformants Expressing Perhydrolase

A fermentor seed culture was prepared by charging a 2-L shake flask with 0.5 L seed medium containing yeast extract (Amberex 695, 5.0 g/L), $K_2HPO_4$ (10.0 g/L), $KH_2PO_4$ (7.0 g/L), sodium citrate dihydrate (1.0 g/L), $(NH_4)_2SO_4$ (4.0 g/L), $MgSO_4$ heptahydrate (1.0 g/L) and ferric ammonium citrate (0.10 g/L). The pH of the medium was adjusted to 6.8 and the medium was sterilized in the flask. Post sterilization additions included glucose (50 wt %, 10.0 mL) and 1 mL ampicillin (25 mg/mL) stock solution. The seed medium was inoculated with a 1-mL culture of *E. coli* KLP18/pSW196 or *E. coli* KLP18/pSW207 in 20% glycerol, and cultivated at 35° C. and 300 rpm. The seed culture was transferred at ca. 1-2 $OD_{550nm}$ to a 14-L fermentor (Braun Biotech, Allentown, Pa.) with 8 L of medium at 35° C. containing $KH_2PO_4$ (3.50 g/L), $FeSO_4$ heptahydrate (0.05 g/L), $MgSO_4$ heptahydrate (2.0 g/L), sodium citrate dihydrate (1.90 g/L), yeast extract (Amberex 695, 5.0 g/L), Biospumex153K antifoam (0.25 mL/L, Cognis Corporation, Monheim, Germany), NaCl (1.0 g/L), $CaCl_2$ dihydrate (10 g/L), and NIT trace elements solution (10 mL/L). The trace elements solution contained citric acid monohydrate (10 g/L), $MnSO_4$ hydrate (2 g/L), NaCl (2 g/L), $FeSO_4$ heptahydrate (0.5 g/L), $ZnSO_4$ heptahydrate (0.2 g/L), $CuSO_4$ pentahydrate (0.02 g/L) and $NaMoO_4$ dihydrate (0.02 g/L). Post sterilization additions included glucose solution (50% w/w, 80.0 g) and ampicillin (25 mg/mL) stock solution (16.00 mL). Glucose solution (50% w/w) was used for fed batch. Glucose feed was initiated when glucose concentration decreased to 0.5 g/L, starting at 0.31 g feed/min and increasing progressively each hour to 0.36, 0.42, 0.49, 0.57, 0.66, 0.77, 0.90, 1.04, 1.21, 1.41, and 1.63 g/min respectively; the rate remained constant afterwards. Glucose concentration in the medium was monitored and if the concentration exceeded 0.1 g/L the feed rate was decreased or stopped temporarily. Induction was initiated between $OD_{550nm}$=56 and $OD_{550nm}$=80 with addition of 16 mL IPTG (0.5 M) for the various strains. The dissolved oxygen (DO) concentration was controlled at 25% of air saturation. The DO was controlled first by impeller agitation rate (400 to 1400 rpm) and later by aeration rate (2 to 10 slpm). The pH was controlled at 6.8. $NH_4OH$ (29% w/w) and $H_2SO_4$ (20% w/v) were used for pH control. The head pressure was 0.5 bars. The cells were harvested by centrifugation 16 h post IPTG addition.

EXAMPLE 7

Preparation of Heat-Treated Cell Extracts of CE-7 Esterases/Perhydrolases

A cell extract of an *E. coli* transformant expressing perhydrolase from *Thermotoga neapolitana* (KLP18/pSW196) or *Thermotoga maritima* MSB8 (KLP18/pSW207) was prepared by passing a suspension of cell paste (20 wt % wet cell weight) in 0.05 M potassium phosphate buffer (pH 7.0) containing dithiothreitol (1 mM) twice through a French press having a working pressure of 16,000 psi (~110 MPa). The crude extract was then centrifuged at 20,000×g to remove cellular debris, producing a clarified cell extract that was assayed for total soluble protein (Bicinchoninic Acid Kit for Protein Determination, Sigma Aldrich catalog #BCA1-KT). The clarified *Thermotoga maritima* MSB8 or *Thermotoga neapolitana* perhydrolase-containing extract was heated for 20 min at 75° C., followed immediately by cooling in an ice/water bath to 5° C. The resulting mixture was centrifuged to remove precipitated protein, and the supernatant collected and assayed for total soluble protein as before. SDS-PAGE of the heat-treated supernatant indicated that the perhydrolase constituted at least ca. 90% of the total soluble protein present in the supernatant.

EXAMPLE 8

Temperature Stability of *T. neapolitana* Perhydrolase/Trehalose Spray-Dried Enzyme Powders A set of ten aqueous mixtures were prepared that contained varying concentrations of the heat-treated cell extract protein of *E. coli* KLP18/pSW196 (≧90% *T. neapolitana* perhydrolase by PAGE), trehalose (Cargill), and, optionally, polysorbate 80 (p80) as surfactant in sodium bicarbonate buffer (50 mM, pH=8.1) (Table 1). These solutions were spray-dried using a Buchi B-290 glass-chamber spray dryer (inlet temperature=170° C., exit temperature=90° C., feed rate=3 mL/min to 10 mL/min) to produce ten spray-dried enzyme powders; the weight percent protein in the powders was determined using the BCA (Bicinchoninic acid) protein assay, and the glass transition temperatures (Tg) of these powders were measured using modulated differential scanning calorimetry (Table 1).

UFC3LKT 00) by centrifugation for 2 min at 12,000 rpm. An aliquot (0.100 mL) of the resulting filtrate was transferred to a 1.5-mL screw cap HPLC vial (Agilent Technologies, Palo Alto, Calif.; #5182-0715) containing 0.300 mL of deionized water, then 0.100 mL of 20 mM MTS (methyl-p-tolyl sulfide) in acetonitrile was added, the vial capped, and the contents briefly mixed prior to a 10 min incubation at ca. 25° C. in the absence of light. To the vial was then added 0.400 mL of acetonitrile and 0.100 mL of a solution of triphenylphosphine (TPP, 40 mM) in acetonitrile, the vial re-capped, and the resulting solution mixed and incubated at ca. 25° C. for 30 min in the absence of light. To the vial was then added 0.100 mL of 10 mM N,N-diethyl-m-toluamide (DEET; HPLC external standard) and the resulting solution analyzed by HPLC for MTSO (methyl-p-tolyl sulfoxide), the stoichiometric oxidation product produced by reaction of MTS with peracetic acid. A control reaction was run in the absence of added extract protein or triacetin to determine the rate of oxidation of MTS in the assay mixture by hydrogen peroxide, for correction of the rate of peracetic acid production for background MTS oxidation. HPLC method: Supelco Discovery C8 column (10-cm×4.0-mm, 5 μm) (cat. #569422-U) with Supelco Supelguard Discovery C8 precolumn (Sigma-Aldrich; cat #59590-U); 10 microliter injection volume; gradient method with $CH_3CN$ (Sigma-Aldrich; catalog #270717) and deionized water at 1.0 mL/min and ambient temperature.

TABLE 1

Composition of protein/excipient solutions used to produce *T. neapolitana* perhydrolase/trehalose spray-dried enzyme powders, and Tg of corresponding powders.

| protein/excipient solution | trehalose (g/L) | protein (g/L) | excipient/protein | p80 (g/L) | protein/excipient powder | wt % protein in protein/excipient powder | Tg of protein/excipient powder (° C.) |
|---|---|---|---|---|---|---|---|
| S1-1  | 52.5 | 35 | 1.5 | 0.25 | P1-2  | 39.2 | 42 |
| S2-1  | 100  | 50 | 2.0 | 0    | P2-2  | 32.5 | 48 |
| S3-1  | 100  | 50 | 2.0 | 0.50 | P3-2  | 33.2 | 40 |
| S4-1  | 50   | 50 | 1.0 | 0    | P4-2  | 45.1 | 40 |
| S5-1  | 50   | 50 | 1.0 | 0.50 | P5-2  | 46.7 | 54 |
| S6-1  | 40   | 20 | 2.0 | 0    | P6-2  | 31.4 | 44 |
| S7-1  | 40   | 20 | 2.0 | 0.50 | P7-2  | 32.5 | 45 |
| S8-1  | 20   | 20 | 1.0 | 0    | P8-2  | 47.8 | 38 |
| S9-1  | 20   | 20 | 1.0 | 0.50 | P9-2  | 46.6 | 58 |
| S10-1 | 52.5 | 35 | 1.5 | 0.25 | P10-2 | 37.8 | 21 |

The spray-dried enzyme powders were stored in sealed vials at 40° C. and sampled at one-week intervals, and the samples assayed for the concentration of peracetic acid produced in 5 minutes in reactions containing *T. neapolitana* perhydrolase (50 μg protein/mL), $H_2O_2$ (100 mM), triacetin (100 mM) and TURPINAL® SL (500 ppm) in sodium bicarbonate buffer (50 mM, pH 7.2) at 25° C., and analyzed for production of peracetic acid using a modification of the analytical method reported by Karst et al. (below).

A sample (0.040 mL) of the reaction mixture was removed at a predetermined time (5 min) and immediately mixed with 0.960 mL of 5 mM phosphoric acid in water to terminate the reaction by adjusting the pH of the diluted sample to less than pH 4. The resulting solution was filtered using an ULTRAFREE® MC-filter unit (30,000 Normal Molecular Weight Limit (NMWL), Millipore Corp., Billerica, Mass., cat

TABLE 2

HPLC Gradient for analysis of peracetic acid.

| Time (min:sec) | (% $CH_3CN$) |
|---|---|
| 0:00 | 40 |
| 3:00 | 40 |
| 3:10 | 100 |
| 4:00 | 100 |
| 4:10 | 40 |
| 7:00 (stop) | 40 |

The perhydrolytic activity of the *T. neapolitana* perhydrolase/trehalose spray-dried powder was stable over eight weeks of storage at 40° C. (Table 3).

TABLE 3

Temperature stability of T. neapolitana perhydrolase/trehalose spray-dried enzyme powders during storage at 40° C. PAA (ppm) produced in 5 min at 25° C. by reaction of triacetin (100 mM) and $H_2O_2$ (100 mM) in sodium bicarbonate buffer (50 mM, pH 7.2) containing T. neapolitana perhydrolase/trehalose spray-dried powder (50 µg protein/mL) and TURPINAL® SL (500 ppm).

| time at 40 °C. | PAA (ppm) in 5 minutes | | | | | | | | | |
|---|---|---|---|---|---|---|---|---|---|---|
| | P1-2 | P2-2 | P3-2 | P4-2 | P5-2 | P6-2 | P7-2 | P8-2 | P9-2 | P10-2 |
| initial | 1855 | 1983 | 2075 | 2025 | 1769 | 1891 | 1902 | 1777 | 1880 | 1945 |
| week 1 | 1872 | 2019 | 2060 | 1785 | 1776 | 1887 | 2013 | 1903 | 2046 | 2204 |
| week 2 | 1830 | 1899 | 1870 | 1771 | 1833 | 1930 | 1987 | 1933 | 2146 | 2222 |
| week 3 | 1888 | 1974 | 1887 | 1973 | 1977 | 2223 | 2102 | 1924 | 2080 | 2104 |
| week 4 | 1894 | 1878 | 2035 | 1881 | 1712 | 1918 | 1902 | 1793 | 1720 | 1988 |
| week 5 | 1595 | 1744 | 1706 | 1565 | 1871 | 2052 | 1933 | 1783 | 1908 | 1985 |
| week 6 | 1908 | 1760 | 1538 | 1545 | 1825 | 1864 | 1756 | 1675 | 1659 | 1758 |
| week 7 | 1562 | 1797 | 1614 | 1487 | 1551 | 1774 | 1879 | 1927 | 1866 | 1957 |
| week 8 | 1881 | 1959 | 1792 | 1753 | 1939 | 2123 | 1972 | 1907 | 1902 | 2095 |

EXAMPLE 9

Temperature Stability of T. neapolitana Perhydrolase/Trehalose Spray-Dried Enzyme Powders in a Mixture of Enzyme Powder and Triacetin The spray-dried enzyme powders prepared as described in Example 8 were evaluated for stability when stored for eight weeks at 40° C. as a mixture of the spray-dried powder in triacetin. Spray-dried enzyme powders were added to triacetin to produce a mixture containing 0.200 g of protein in 87.2 g of triacetin. The resulting mixtures were stored at 40° C., and a 2.19 g sample of the well-stirred mixture was assayed weekly at 25° C. in a 100-mL reaction containing 100 mM hydrogen peroxide and TURPINAL® SL (500 ppm) in 50 mM sodium bicarbonate buffer at pH 7.2, where the resulting concentration of triacetin and protein was 100 mM and 50 µg/mL, respectively. Comparison of the data in Table 4 with the data in Example 8, Table 3, demonstrates the instability of T. neapolitana perhydrolase/trehalose spray-dried enzyme powders when stored as a mixture with triacetin.

EXAMPLE 10

Temperature Stability of T. neapolitana Perhydrolase/Maltodextrin Spray-Dried Enzyme Powder An aqueous mixture was prepared containing heat-treated cell extract protein of E. coli KLP18/pSW196 (34 g protein/L, ≧90% T. neapolitana perhydrolase by PAGE) and maltodextrin (66.7 g/L MALTRIN® M100 maltodextrin, 14.7 g/L MALTRIN® M250, 14.7 g/L MALTRIN® M040, Grain Processing Corporation, Muscatine, Iowa) as excipient in 50 mM sodium bicarbonate (pH 8.1). This solution was spray-dried using a spray dryer (GEA Niro, 3-ft diameter, inlet temperature=226° C., exit temperature=76° C., feed rate=60 g/min) to produce a spray-dried enzyme powder; the weight percent protein in the powder (20.3 wt %) was determined using the BCA (Bicinchoninic acid) protein assay, and the glass transition temperature of this powder (Tg=54° C.) was measured using modulated differential scanning calorimetry. This solution was spray-dried to produce a powder that was then tested for stability during storage at 40° C. for 9 weeks. The spray-dried enzyme powder (stored at 40° C.) was sampled at one-week intervals and assayed for activity using 50 µg protein/mL of T. neapolitana perhydrolase, $H_2O_2$ (100 mM), triacetin

TABLE 4

Temperature stability of T. neapolitana perhydrolase/trehalose spray-dried enzyme powders during storage in a mixture of enzyme powder and triacetin at 40° C. PAA (ppm) produced in 5 min at 25° C. by reaction of triacetin (100 mM) and $H_2O_2$ (100 mM) in sodium bicarbonate buffer (50 mM, pH 7.2) containing T. neapolitana perhydrolase (50 µg protein/mL) and TURPINAL® SL (500 ppm).

| time at 40 °C. | PAA (ppm) in 5 minutes | | | | | | | | | |
|---|---|---|---|---|---|---|---|---|---|---|
| | P1-2 | P2-2 | P3-2 | P4-2 | P5-2 | P6-2 | P7-2 | P8-2 | P9-2 | P10-2 |
| initial | 1650 | 1495 | 1539 | 1569 | 1666 | 1735 | 1552 | 1327 | 1712 | 1816 |
| week 1 | 1214 | 1359 | 1597 | 1599 | 1589 | 1632 | 1515 | 1469 | 1421 | 1577 |
| week 2 | 1303 | 1609 | 1580 | 1316 | 1293 | 1682 | 1353 | 971 | 1402 | 1483 |
| week 3 | 1092 | 1573 | 1568 | 1233 | 1293 | 1245 | 1268 | 849 | 1324 | 1388 |
| week 4 | 828 | 1563 | 1420 | 1226 | 1199 | 1608 | 1361 | 961 | 1172 | 1273 |
| week 5 | 622 | 1340 | 1114 | 1294 | 1154 | 1663 | 1163 | 739 | 815 | 667 |
| week 6 | 636 | 1301 | 990 | 970 | 895 | 1318 | 514 | 313 | 699 | 372 |
| week 7 | 281 | 998 | 1140 | 841 | 798 | 962 | 259 | 188 | 831 | 521 |
| week 8 | 254 | 569 | 659 | 563 | 567 | 483 | 414 | 323 | 494 | 321 |

(100 mM) and TURPINAL® SL (500 ppm) in 50 mM bicarbonate buffer (pH 7.2) at 25° C., and analyzed for production of peracetic acid using a modification of the analytical method reported by Karst et al., supra. The perhydrolytic activity of the *T. neapolitana* perhydrolase/maltodextrin spray-dried powder was stable over eight weeks of storage at 40° C. (Table 5).

TABLE 5

Temperature stability of *T. neapolitana* perhydrolase/maltodextrin spray-dried enzyme powder during storage at 40° C. PAA (ppm) produced in 5 min at 25° C. by reaction of triacetin (100 mM) and $H_2O_2$ (100 mM) in sodium bicarbonate buffer (50 mM, pH 7.2) containing *T. neapolitana* perhydrolase (50 µg protein/mL) and TURPINAL ® SL (500 ppm).

| time at 40° C. | PAA (ppm) in 5 min |
| --- | --- |
| initial | 1142 |
| week 1 | 1117 |
| week 2 | 1135 |
| week 3 | 1087 |
| week 4 | 964 |
| week 5 | 1153 |
| week 6 | 930 |
| week 7 | 1025 |
| week 8 | 964 |

EXAMPLE 11

Temperature Stability of *T. neapolitana* perhydrolase/Maltodextrin Spray-Dried Enzyme Powder Stored in a Mixture of Enzyme Powder and Triacetin The spray-dried enzyme powder prepared as described in Example 10 was evaluated for stability when stored for twenty-one weeks at 40° C. as a mixture of the spray-dried powder in triacetin. The spray-dried enzyme powder (1.235 g, 20.3 wt % protein) was added to 109 g of triacetin. The resulting mixture was stored at 40° C., and a 2.19 g sample of the well-stirred mixture assayed in duplicate at 25° C. in a 100-mL reaction containing hydrogen peroxide (100 mM) and TURPINAL® SL (500 ppm) in 50 mM sodium bicarbonate buffer at pH 7.2, where the resulting concentration of triacetin and protein was 100 mM and 50 µg/mL, respectively. Comparison of the data in Table 6 with the data in Example 10, Table 5, demonstrates the stability of *T. neapolitana* perhydrolase/maltodextrin spray-dried enzyme powders when stored as a mixture with triacetin.

TABLE 6

Temperature stability of *T. neapolitana* perhydrolase/maltodextrin spray-dried enzyme powder during storage in a mixture of enzyme powder and triacetin at 40° C. PAA (ppm) produced in 5 min at 25° C. by reaction of triacetin (100 mM) and $H_2O_2$ (100 mM) in sodium bicarbonate buffer (50 mM, pH 7.2) containing *T. neapolitana* perhydrolase (50 µg protein/mL) and TURPINAL ® SL (500 ppm).

| time at 40° C. | PAA (ppm) in 5 min | | |
| --- | --- | --- | --- |
| | duplicate A | duplicate B | Average |
| initial | 1010 | 1019 | 1015 |
| week 1 | 983 | 1054 | 1019 |
| week 2 | 897 | 927 | 912 |
| week 3 | 1194 | 1137 | 1166 |
| week 4 | 1139 | 1088 | 1114 |
| week 5 | 1099 | 1069 | 1084 |

TABLE 6-continued

Temperature stability of *T. neapolitana* perhydrolase/maltodextrin spray-dried enzyme powder during storage in a mixture of enzyme powder and triacetin at 40° C. PAA (ppm) produced in 5 min at 25° C. by reaction of triacetin (100 mM) and $H_2O_2$ (100 mM) in sodium bicarbonate buffer (50 mM, pH 7.2) containing *T. neapolitana* perhydrolase (50 µg protein/mL) and TURPINAL ® SL (500 ppm).

| time at 40° C. | PAA (ppm) in 5 min | | |
| --- | --- | --- | --- |
| | duplicate A | duplicate B | Average |
| week 6 | 1098 | 978 | 1038 |
| week 7 | 1018 | 1006 | 1012 |
| week 8 | 907 | 892 | 900 |
| week 12 | 925 | 936 | 931 |
| week 18 | 824 | ND | |
| week 21 | 792 | ND | |

ND = a duplicate assay was not done

EXAMPLE 12

Temperature Stability of *T. neapolitana* Perhydrolase/Maltodextrin Spray-Dried Enzyme Powder Stored in a Mixture of Enzyme Powder, Sodium Bicarbonate and Triacetin The spray-dried enzyme powder prepared as described in Example 10 was evaluated for stability when stored for 21 weeks at 40° C. as a mixture of the spray-dried powder in a mixture of triacetin and sodium bicarbonate. The spray-dried enzyme powder (0.988 g, 20.3 wt % protein) was added to a mixture of 87.2 g of triacetin and 16.8 g of sodium bicarbonate (Grade 3DF (powder), Church & Dwight). The resulting mixture was stored at 40° C., and a 2.62 g sample of the well-stirred mixture was assayed in duplicate at 25° C. in a 100-mL reaction containing hydrogen peroxide (100 mM) and TURPINAL® SL (500 ppm), where the resulting concentrations of triacetin, sodium bicarbonate and protein were 100 mM, 50 mM (pH 7.2) and 50 µg/mL, respectively. Comparison of the data in Table 7 with the data in Example 11, Table 6, demonstrates the stability of *T. neapolitana* perhydrolase/maltodextrin spray-dried enzyme powders when stored for twenty-one weeks at 40° C. as a mixture with triacetin and solid sodium bicarbonate is improved when compared to the stability of *T. neapolitana* perhydrolase/maltodextrin spray-dried enzyme powders when stored for twenty-one weeks at 40° C. as a mixture with triacetin alone. At the longer storage times, e.g. 21 weeks, the perhydrolase still retains ca. 100% of initial activity in a mixture of triacetin and sodium bicarbonate.

TABLE 7

Temperature stability of *T. neapolitana* perhydrolase/maltodextrin spray-dried enzyme powder during storage in a mixture of enzyme powder, sodium bicarbonate and triacetin at 40° C. PAA (ppm) produced in 5 min at 25° C. by reaction of triacetin (100 mM) and $H_2O_2$ (100 mM) in sodium bicarbonate buffer (50 mM, pH 7.2) containing *T. neapolitana* perhydrolase (50 µg protein/mL) and TURPINAL ® SL (500 ppm).

| time at 40° C. | PAA (ppm) in 5 min | | |
| --- | --- | --- | --- |
| | duplicate A | duplicate B | average |
| initial | 950 | 1032 | 991 |
| week 1 | 1060 | 1096 | 1078 |
| week 2 | 1114 | 1114 | 1114 |
| week 4 | 1044 | 974 | 1009 |
| week 8 | 1085 | 1046 | 1066 |
| week 12 | 1101 | 1122 | 1112 |

TABLE 7-continued

Temperature stability of *T. neapolitana* perhydrolase/maltodextrin spray-dried enzyme powder during storage in a mixture of enzyme powder, sodium bicarbonate and triacetin at 40° C. PAA (ppm) produced in 5 min at 25° C. by reaction of triacetin (100 mM) and $H_2O_2$ (100 mM) in sodium bicarbonate buffer (50 mM, pH 7.2) containing *T. neapolitana* perhydrolase (50 µg protein/mL) and TURPINAL® SL (500 ppm).

| time at 40° C. | PAA (ppm) in 5 min | | |
|---|---|---|---|
| | duplicate A | duplicate B | average |
| week 17 | 1013 | ND | |
| week 21 | 1162 | ND | |

ND = a duplicate assay was not done

EXAMPLE 13

Temperature Stability of *T. maritima* Perhydrolase/Maltodextrin Spray-Dried Enzyme Powder An aqueous mixture was prepared containing heat-treated cell extract protein of *E. coli* KLP18/pSW207 (21 g protein/L, ≧90% *T. maritima* perhydrolase by PAGE) and maltodextrin (31 g/L maltodextrin DE 13-17 and 31 g/L maltodextrin DE 4-7, Aldrich) as excipient in 50 mM sodium bicarbonate (pH 8.1). This solution was spray-dried using a Buchi B-290 glass-chamber spray dryer (inlet temperature=170° C., exit temperature=90° C., feed rate=4.5 mL/min) to produce a spray-dried enzyme powder; the weight percent protein in the powder (18.0 wt %) was determined using the BCA (Bicinchoninic acid) protein assay, and the glass transition temperature of this powder (Tg=90° C.) was measured using modulated differential scanning calorimetry. This solution was spray-dried to produce a powder that was then tested for stability during storage at 40° C. for 7 weeks. The spray-dried enzyme powder (stored at 40° C.) was sampled at one-week intervals and assayed for activity using 50 µg protein/mL of *T. maritima* perhydrolase, $H_2O_2$ ($H_2O_2$ (100 mM)), triacetin (100 mM) and TURPINAL® SL (500 ppm) in 50 mM bicarbonate buffer (pH 7.2) at 25° C., and analyzed for production of peracetic acid using a modification of the analytical method reported by Karst et al., supra. The perhydrolytic activity of the *T. maritima* perhydrolase/maltodextrin spray-dried powder was stable over seven weeks of storage at 40° C. (Table 8).

TABLE 8

Temperature stability of *T. maritima* perhydrolase/maltodextrin spray-dried enzyme powder during storage at 40° C. PAA (ppm) produced in 5 min at 25° C. by reaction of triacetin (100 mM) and $H_2O_2$ (100 mM) in sodium bicarbonate buffer (50 mM, pH 7.2) containing *T. maritima* perhydrolase (50 µg protein/mL) and TURPINAL® SL (500 ppm).

| time at 40° C. | PAA (ppm) in 5 min |
|---|---|
| initial | 1373 |
| week 1 | 1262 |
| week 2 | 1548 |
| week 3 | 1317 |
| week 4 | 1316 |
| week 5 | 1378 |
| week 6 | 1296 |
| week 7 | 1475 |

EXAMPLE 14

Temperature Stability of *T. maritima* Perhydrolase/Maltodextrin Spray-Dried Enzyme Powder Stored in a Mixture of Enzyme Powder and Triacetin The spray-dried enzyme powder prepared as described in Example 13 was evaluated for stability when stored for seven weeks at 40° C. as a mixture of the spray-dried powder in triacetin. The spray-dried enzyme powder (0.556 g, 18.0 wt % protein) was added to 43.6 g of triacetin. The resulting mixture was stored at 40° C., and a 2.21 g sample of the well-stirred mixture assayed in duplicate at 25° C. in a 100-mL reaction containing hydrogen peroxide (100 mM) and TURPINAL® SL (500 ppm) in 50 mM sodium bicarbonate buffer at pH 7.2, where the resulting concentration of triacetin and protein was 100 mM and 50 µg/mL, respectively. Comparison of the data in Table 9 with the data in Example 13, Table 8, demonstrates the stability of *T. maritima* perhydrolase/maltodextrin spray-dried enzyme powders when stored as a mixture with triacetin.

TABLE 9

Temperature stability of *T. maritima* perhydrolase/maltodextrin spray-dried enzyme powder during storage in a mixture of enzyme powder and triacetin at 40° C. PAA (ppm) produced in 5 min at 25° C. by reaction of triacetin (100 mM) and $H_2O_2$ (100 mM) in sodium bicarbonate buffer (50 mM, pH 7.2) containing *T. maritima* perhydrolase (50 µg protein/mL) and TURPINAL® SL (500 ppm).

| time at 40° C. | PAA (ppm) in 5 min |
|---|---|
| initial | 1137 |
| week 1 | 1089 |
| week 2 | 1138 |
| week 3 | 1213 |
| week 4 | 1130 |
| week 5 | 872 |
| week 6 | 858 |
| week 7 | 1004 |

EXAMPLE 15

Temperature Stability of *T. maritima* Perhydrolase/Maltodextrin Spray-Dried Enzyme Powder Stored in a Mixture of Enzyme Powder, Sodium Bicarbonate and Triacetin The spray-dried enzyme powder prepared as described in Example 13 was evaluated for stability when stored for seven weeks at 40° C. as a mixture of the spray-dried powder in a mixture of triacetin and sodium bicarbonate. The spray-dried enzyme powder (0.556 g, 18.0 wt % protein) was added to 43.6 g of triacetin and 8.4 g of sodium bicarbonate (Grade 3DF (powder), Church & Dwight). The resulting mixture was stored at 40° C., and a 2.63 g sample of the well-stirred mixture assayed in duplicate at 25° C. in a 100-mL reaction containing hydrogen peroxide (100 mM) and TURPINAL® SL (500 ppm), where the resulting concentrations of triacetin, sodium bicarbonate buffer (pH 7.2) and protein were 100 mM, 50 mM and 50 µg/mL, respectively. Comparison of the data in Table 10 with the data in Example 14, Table 9, demonstrates the improved stability of *T. maritima* perhydrolase/maltodextrin spray-dried enzyme powders when stored for five, six and seven weeks at 40° C. as a mixture with triacetin and solid sodium bicarbonate when compared to the stability of *T. neapolitana* perhydrolase/maltodextrin spray-dried enzyme powders when stored for five, six and seven weeks at 40° C. as a mixture with triacetin alone.

TABLE 10

Temperature stability of *T. maritima* perhydrolase/maltodextrin spray-dried enzyme powder during storage in a mixture of enzyme powder, sodium bicarbonate and triacetin at 40° C. PAA (ppm) produced in 5 min at 25° C. by reaction of triacetin (100 mM) and $H_2O_2$ (100 mM) in sodium bicarbonate buffer (50 mM, pH 7.2) containing *T. maritima* perhydrolase (50 μg protein/mL) and TURPINAL ® SL (500 ppm).

| time at 40° C. | PAA (ppm) in 5 min |
|---|---|
| initial | 1153 |
| week 1 | 1138 |
| week 2 | 1343 |
| week 3 | 1242 |
| week 4 | 1111 |
| week 5 | 1149 |
| week 6 | 1184 |
| week 7 | 1109 |

EXAMPLE 16

Perhydrolysis of Propylene Glycol Diacetate or Ethylene Glycol Diacetate Using *Bacillus subtilis* ATCC® 31954™ Perhydrolase A homogenate of a transformant expressing wild-type perhydrolase from *Bacillus subtilis* ATCC® 31954™ (KLP18/pSW194) was prepared from a suspension of cell paste (20 wt % wet cell weight) in 0.05 M potassium phosphate buffer (pH 7.0) containing dithiothreitol (1 mM). The crude homogenate was centrifuged to remove cellular debris, producing a clarified cell extract that was heat-treated at 65° C. for 30 min. The resulting mixture was centrifuged, and the heat-treated supernatant concentrated on a 30K MWCO (molecular weight cutoff) membrane to a concentration of 32 mg/mL total dissolved solids; a SDS-PAGE of the clarified, heat-treated cell extract indicated that the perhydrolase was at least 85-90% pure. To this concentrate was then added 2.06 grams of $NaH_2PO_4$ and 1.17 grams $Na_2HPO_4$ per gram of solids was added to this concentrate to produce an approximate 3:1 ratio (wt/wt) of phosphate buffer to heat-treated cell extract protein. This solution was diluted by 30 wt % with deionized water, then spray-dried (180° C. inlet temperature, 70° C. exit temperature) using a Buchi B-290 laboratory spray dryer); the resulting spray-dried powder contained 25.5 wt % protein (Bradford protein assay) and was 94.3 wt % dry solids.

Reactions (10 mL total volume) were run at 23° C. in 50 mM sodium bicarbonate buffer (initial pH 7.2) containing propylene glycol diacetate (PGDA) or ethylene glycol diacetate (EGDA), hydrogen peroxide (100 mM) and 123 μg/mL of a heat-treated extract protein from the spray-dried *E. coli* KLP18/pSW194 (expressing *Bacillus subtilis* ATCC® 31954™ wild-type perhydrolase) (prepared as described above). A control reaction for each reaction condition was run to determine the concentration of peracetic acid produced by chemical perhydrolysis of triacetin by hydrogen peroxide in the absence of added heat-treated extract protein. The reactions were sampled at 1, 5, and 30 minutes and the samples analyzed for peracetic acid using the Karst derivatization protocol (Karst et al., supra); aliquots (0.040 mL) of the reaction mixture were removed and mixed with 0.960 mL of 5 mM phosphoric acid in water; adjustment of the pH of the diluted sample to less than pH 4 immediately terminated the reaction. The resulting solution was filtered using an ULTRAFREE® MC-filter unit (30,000 Normal Molecular Weight Limit (NMWL), Millipore cat #UFC3LKT 00) by centrifugation for 2 min at 12,000 rpm. An aliquot (0.100 mL) of the resulting filtrate was transferred to 1.5-mL screw cap HPLC vial (Agilent Technologies, Palo Alto, Calif.; #5182-0715) containing 0.300 mL of deionized water, then 0.100 mL of 20 mM MTS (methyl-p-tolyl-sulfide) in acetonitrile was added, the vials capped, and the contents briefly mixed prior to a 10 min incubation at ca. 25° C. in the absence of light. To each vial was then added 0.400 mL of acetonitrile and 0.100 mL of a solution of triphenylphosphine (TPP, 40 mM) in acetonitrile, the vials re-capped, and the resulting solution mixed and incubated at ca. 25° C. for 30 min in the absence of light. To each vial was then added 0.100 mL of 10 mM N,N-diethyl-m-toluamide (DEET; HPLC external standard) and the resulting solution analyzed by HPLC. The peracetic acid concentrations produced in 1 min, 5 min and 30 min are listed in Table 11.

TABLE 11

Peracetic acid (PAA) concentration produced in reactions utilizing propylene glycol diacetate (PGDA) or ethylene glycol diacetate (EGDA) and hydrogen peroxide (100 mM) in sodium bicarbonate buffer (50 mM, initial pH 7.2) at 23° C. using 123 μg/mL of heat-treated extract protein from *E. coli* KLP18/pSW194 (*Bacillus subtilis* ATCC ® 31954 ™ perhydrolase).

| perhydrolase (50 μg/mL) | substrate (100 mM) | PAA, 1 min (ppm) | PAA, 5 min (ppm) | PAA, 30 min (ppm) |
|---|---|---|---|---|
| no enzyme (control) | PGDA | 0 | 64 | 241 |
| *B. subtilis* ATCC ® 31954 | PGDA | 666 | 781 | 815 |
| no enzyme (control) | EGDA | 0 | 18 | 141 |
| *B. subtilis* ATCC ® 31954 | EGDA | 747 | 931 | 963 |

EXAMPLE 17

Perhydrolysis of Propylene Glycol Diacetate or Ethylene Glycol Diacetate Using *T. maritima* and *T. neapolitana* Wild-type and Variant Perhydrolases Cell extracts of transformants expressing *Thermotoga neapolitana* wild-type perhydrolase (KLP18/pSW196), *Thermotoga neapolitana* C277S variant perhydrolase (KLP18/pSW196/C277S), *Thermotoga neapolitana* C277T variant perhydrolase (KLP18/pSW196/C277T), *Thermotoga maritima* wild-type perhydrolase (KLP18/pSW228), *Thermotoga maritima* C277S variant perhydrolase (KLP18/pSW228/C277S), and *Thermotoga maritima* C277T variant perhydrolase (KLP18/pSW228/C277T) were each prepared by passing a suspension of cell paste (20 wt % wet cell weight) in 0.05 M potassium phosphate buffer (pH 7.0) containing dithiothreitol (1 mM) twice through a French press having a working pressure of 16,000 psi (~110 MPa). The lysed cells were centrifuged for 30 minutes at 12,000×g, producing a clarified cell extract that was assayed for total soluble protein (Bradford assay). The supernatant was heated at 75° C. for 20 minutes, followed by quenching in an ice bath for 2 minutes. Precipitated protein was removed by centrifugation for 10 minutes at 11,000×g. SDS-PAGE of the resulting heat-treated extract protein supernatant indicated that the CE-7 enzyme comprised approximately 85-90% of the total protein in the preparation. The heat-treated extract protein supernatant was frozen in dry ice and stored at −80° C. until use.

A first set of reactions (10 mL total volume) were run at 20° C. in 10 mM sodium bicarbonate buffer (initial pH 8.1) containing propylene glycol diacetate (PGDA) or ethylene glycol diacetate (EGDA) (100 mM), hydrogen peroxide (100 mM) and 25 µg/mL of heat-treated extract protein from one of *E. coli* KLP18/pSW196 (*Thermotoga neapolitana* wild-type perhydrolase), *E. coli* KLP18/pSW196/C277S (*Thermotoga neapolitana* C277S variant perhydrolase), *E. coli* KLP18/pSW196/C277T (*Thermotoga neapolitana* C277T variant perhydrolase), *E. coli* KLP18/pSW228 (*Thermotoga maritima* wild-type perhydrolase), *E. coli* KLP18/pSW228/C277S (*Thermotoga maritima* C277S variant perhydrolase), and *E. coli* KLP18/pSW228/C277T (*Thermotoga maritima* C277T variant perhydrolase) (prepared as described above). A control reaction for each reaction condition was run to determine the concentration of peracetic acid produced by chemical perhydrolysis of triacetin by hydrogen peroxide in the absence of added extract protein. The reactions were sampled at 1, 5, and 30 minutes and the samples analyzed for peracetic acid using the Karst derivatization protocol (Karst et al., supra) and HPLC analytical method (supra). The peracetic acid concentrations produced in 1 min, 5 min and 30 min are listed in Table 12.

A second set of reactions (10 mL total volume) were run at 20° C. in 10 mM sodium bicarbonate buffer (initial pH 8.1) containing propylene glycol diacetate (PGDA) or ethylene glycol diacetate (EGDA) (2 mM), hydrogen peroxide (10 mM) and 10 µg/mL of heat-treated extract protein from one of *E. coli* KLP18/pSW196 (*Thermotoga neapolitana* wild-type perhydrolase), *E. coli* KLP18/pSW196/C277S (*Thermotoga neapolitana* C277S variant perhydrolase), *E. coli* KLP18/pSW196/C277T (*Thermotoga neapolitana* C277T variant perhydrolase), *E. coli* KLP18/pSW228 (*Thermotoga maritima* wild-type perhydrolase), *E. coli* KLP18/pSW228/C277S (*Thermotoga maritima* C277S variant perhydrolase), and *E. coli* KLP18/pSW228/C277T (*Thermotoga maritima* C277T variant perhydrolase) (prepared as described above). A control reaction for each reaction condition was run to determine the concentration of peracetic acid produced by chemical perhydrolysis of triacetin by hydrogen peroxide in the absence of added extract protein. The reactions were sampled at 5 minutes and the samples analyzed for peracetic acid using the Karst derivatization protocol (Karst et al., supra) and HPLC analytical method (supra). The peracetic acid concentrations produced in 5 min are listed in Table 13.

TABLE 12

Peracetic acid (PAA) concentration produced utilizing *T. maritima* and *T. neapolitana* wild-type and variant perhydrolases in reactions at 20 °C. in sodium bicarbonate buffer (10 mM, initial pH 8.1) containing propylene glycol diacetate (PGDA) (100 mM) or ethylene glycol diacetate (EGDA) (100 mM), hydrogen peroxide (100 mM) and 25 µg/mL of heat-treated extract protein.

| perhydrolase | substrate | substrate conc. (mM) | $H_2O_2$ (mM) | PAA, 1 min (ppm) | PAA, 5 min (ppm) | PAA, 30 min (ppm) |
|---|---|---|---|---|---|---|
| no enzyme (control) | PGDA | 100 | 100 | 0 | 15 | 165 |
| *T. maritima* WT | PGDA | 100 | 100 | 534 | 1104 | 1695 |
| *T. maritima* C277S | PGDA | 100 | 100 | 647 | 1320 | 1864 |
| *T. maritima* C277T | PGDA | 100 | 100 | 656 | 1174 | 1418 |
| *T. neapolitana* WT | PGDA | 100 | 100 | 513 | 1052 | 1946 |
| *T. neapolitana* C277S | PGDA | 100 | 100 | 875 | 1327 | 1707 |
| *T. neapolitana* C277T | PGDA | 100 | 100 | 724 | 1325 | 1864 |
| no enzyme (control) | EGDA | 100 | 100 | 0 | 70 | 229 |
| *T. maritima* WT | EGDA | 100 | 100 | 765 | 1182 | 1595 |
| *T. maritima* C277S | EGDA | 100 | 100 | 725 | 1240 | 1724 |
| *T. maritima* C277T | EGDA | 100 | 100 | 802 | 1218 | 1734 |
| *T. neapolitana* WT | EGDA | 100 | 100 | 603 | 1132 | 1643 |
| *T. neapolitana* C277S | EGDA | 100 | 100 | 680 | 1305 | 1698 |
| *T. neapolitana* C277T | EGDA | 100 | 100 | 688 | 1164 | 1261 |

TABLE 13

Peracetic acid (PAA) concentration produced utilizing *T. maritima* and *T. neapolitana* wild-type and variant perhydrolases in reactions at 20° C. in sodium bicarbonate buffer (10 mM, initial pH 8.1) containing propylene glycol diacetate (PGDA) (2 mM) or ethylene glycol diacetate (EGDA) (2 mM), hydrogen peroxide (10 mM) and 10 µg/mL of heat-treated extract protein.

| perhydrolase | substrate | substrate conc. (mM) | $H_2O_2$ (mM) | PAA, 5 min (ppm) |
|---|---|---|---|---|
| no enzyme (control) | PGDA | 2 | 10 | 3.6 |
| *T. maritima* WT | PGDA | 2 | 10 | 5.0 |
| *T. maritima* C277S | PGDA | 2 | 10 | 7.2 |
| *T. maritima* C277T | PGDA | 2 | 10 | 7.9 |
| *T. neapolitana* WT | PGDA | 2 | 10 | 5.7 |
| *T. neapolitana* C277S | PGDA | 2 | 10 | 7.9 |
| *T. neapolitana* C277T | PGDA | 2 | 10 | 3.9 |
| no enzyme (control) | EGDA | 2 | 10 | 3.3 |
| *T. maritima* WT | EGDA | 2 | 10 | 9.9 |
| *T. maritima* C277S | EGDA | 2 | 10 | 13.6 |
| *T. maritima* C277T | EGDA | 2 | 10 | 22.9 |
| *T. neapolitana* WT | EGDA | 2 | 10 | 6.6 |
| *T. neapolitana* C277S | EGDA | 2 | 10 | 18.4 |
| *T. neapolitana* C277T | EGDA | 2 | 10 | 20.2 |

What is claimed is:

1. A process for enzymatically producing a peroxycarboxylic acid comprising:
   (a) providing a set of reaction components, said components comprising:
      (1) a formulation comprising a mixture of:
         (I) at least one carboxylic acid ester selected from the group consisting of monoacetin, diacetin, triacetin, monopropionin, dipropionin, tripropionin, monobutyrin, dibutyrin, tributyrin, and mixtures thereof;
         (II) an enzyme powder comprising
            (i) at least one enzyme structurally classified as a CE-7 enzyme and having perhydrolvsis activity and a signature motif comprising:
               (A) an RGQ motif at amino acid residues 118-120,
               (B) a GXSQG motif at amino acid residues 179-183, and
               (C) an HE motif at amino acid residues 298-299 when aligned to reference sequence SEQ ID NO:1 using CLUSTALW,
            (ii) at least one excipient, and
            (iii) optionally at least one surfactant; and
         (III) at least one buffer; wherein said at least one buffer enhances the stability of said at least one enzyme when present in said formulation as compared to the perhydrolase activity of said at least one enzyme when the at least one excipient is not present; and
      (2) a source of peroxygen in water; and
   (b) combining said reaction components whereby a peroxycarboxylic acid is produced.

2. The process of claim 1, wherein:
   (a) the at least one enzyme comprises an amino acid sequence selected from the group consisting of SEQ ID NO:6, SEQ ID NO:7, SEQ ID NO:19 and SEQ ID NO:20, wherein amino acid residue 277 of SEQ ID NO: 19 or SEQ ID NO: 20 is selected from the group consisting of alanine, valine, serine, and threonine;
   (b) the at least one excipient is maltodextrin;
   (c) the at least one buffer is selected from the group consisting of sodium bicarbonate, potassium bicarbonate, a mixture of sodium bicarbonate and potassium bicarbonate, sodium phosphate, potassium phosphate, and a mixture of sodium phosphate and potassium phosphate;
   (d) the at least one carboxylic acid ester is triacetin; and
   (e) the peroxycarboxylic acid produced is peracetic acid.

3. The process of claim 1, wherein the at least one excipient ranges from about 95 wt % to about 25 wt % of the enzyme powder.

4. The process of claim 3, wherein the at least one excipient is selected from the group consisting of maltodextrin, trehalose, xylan, mannan, fucoidan, galactomannan, chitosan, raffinose, stachyose, pectin, inulin, levan, graminan, amylopectin, and mixtures thereof.

5. The process of claim 4, wherein the at least one excipient is maltodextrin.

6. The process of claim 4, wherein the at least one excipient is trehalose.

7. The process of claim 1, wherein the carboxylic acid ester is triacetin.

8. The process of claim 1, wherein the at least one surfactant is present and is polysorbate 80.

9. The process of claim 3, wherein the at least one excipient is an oligosaccharide excipient having a number average molecular weight of at least about 1250 and a weight average molecular weight of at least about 9000.

10. The process of claim 9, wherein the oligosaccharide excipient has a number average molecular weight of at least about 1700 and a weight average molecular weight of at least about 15000.

11. The process of claim 1, wherein the formulation is substantially free of water.

12. The process of claim 11, wherein the at least one buffer is sodium bicarbonate, potassium bicarbonate, a mixture of sodium bicarbonate and potassium bicarbonate, sodium phosphate, potassium phosphate, or a mixture of sodium phosphate and potassium phosphate.

13. The process of claim 12, wherein the at least one buffer has a buffering capacity in a pH range of from about 5.5 to about 9.5.

14. The process of claim 12, wherein:
(a) the at least one enzyme comprises an amino acid sequence selected from the group consisting of SEQ ID NO:6, SEQ ID NO:7, SEQ ID NO:19, and SEQ ID NO:20, wherein amino acid residue 277 of SEQ ID NO: 19 or SEQ ID NO: 20 is selected from the group consisting of alanine, valine, serine, and threonine, and
(b) the carboxylic acid ester is selected from the group consisting of diacetin, triacetin, and mixtures thereof.

15. The process of claim 14, wherein said at least one excipient is maltodextrin.

16. The process of claim 12, wherein:
(a) the at least one enzyme comprises an amino acid sequence selected from the group consisting of SEQ ID NO:6 and SEQ ID NO:7;
(b) the at least one excipient is maltodextrin;
(c) the at least one buffer is selected from the group consisting of sodium bicarbonate, potassium bicarbonate, and mixtures thereof; and
(d) said carboxylic acid ester is triacetin.

17. The process of claim 16, wherein the at least one buffer is sodium bicarbonate.

* * * * *